US009006415B2

(12) United States Patent
Ren et al.

(10) Patent No.: US 9,006,415 B2
(45) Date of Patent: Apr. 14, 2015

(54) TARGETED DELIVERY OF NUCLEIC ACIDS

(75) Inventors: Yin Ren, Westland, MI (US); Sangeeta N. Bhatia, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 102 days.

(21) Appl. No.: 13/081,432

(22) Filed: Apr. 6, 2011

(65) Prior Publication Data

US 2011/0256088 A1 Oct. 20, 2011

Related U.S. Application Data

(60) Provisional application No. 61/321,157, filed on Apr. 6, 2010.

(51) Int. Cl.
*C07H 21/04* (2006.01)
*A61K 47/48* (2006.01)
*A61K 49/00* (2006.01)

(52) U.S. Cl.
CPC ....... *A61K 47/48315* (2013.01); *A61K 49/0008* (2013.01); *A61K 47/48323* (2013.01); *C07K 2319/00* (2013.01); *C07K 2319/01* (2013.01); *C07K 2319/10* (2013.01); *C07K 2319/85* (2013.01)

(58) Field of Classification Search
None
See application file for complete search history.

(56) References Cited

U.S. PATENT DOCUMENTS

| 7,851,615 | B2 * | 12/2010 | Manoharan et al. | 536/24.5 |
|---|---|---|---|---|
| 2006/0222657 | A1 | 10/2006 | Dowdy et al. | |
| 2009/0093026 | A1 | 4/2009 | Dowdy et al. | |
| 2009/0098049 | A1 | 4/2009 | Dowdy et al. | |
| 2009/0099066 | A1 * | 4/2009 | Moulton et al. | 514/7 |
| 2009/0226372 | A1 | 9/2009 | Ruoslahti et al. | |
| 2009/0317906 | A1 | 12/2009 | Weber et al. | |

FOREIGN PATENT DOCUMENTS

| WO | WO 2005/084158 A2 | 9/2005 |
|---|---|---|
| WO | WO 2006/029078 A2 | 3/2006 |
| WO | WO 2007/095152 A2 | 8/2007 |
| WO | WO 2008/054544 A2 | 5/2008 |

OTHER PUBLICATIONS

Ezzat et al. (Current Pharmaceutical Design Mar. 2010, Vo. 16: 1167-1178).*
Deshayes et al. (Advanced Drug Delivery Reviews 20, 2008: 537-547).*
Wang et al. (Journal of Chinese Pharm Sci 18, 2009: 99-105).*
Agaisse et al., Genome-wide RNAi screen for host factors required for intracellular bacterial infection. Science. Aug. 19, 2005;309(5738):1248-51. Epub Jul. 14, 2005.
Akerman et al., Nanocrystal targeting in vivo. Proc Natl Acad Sci U S A. Oct. 1, 2002;99(20):12617-21. Epub Sep. 16, 2002.
Akinc et al., A combinatorial library of lipid-like materials for delivery of RNAi therapeutics. Nat Biotechnol. May 2008;26(5):561-9. Epub Apr. 27, 2008.
Bartlett et al., Impact of tumor-specific targeting on the biodistribution and efficacy of siRNA nanoparticles measured by multimodality in vivo imaging. Proc Natl Acad Sci U S A. Sep. 25, 2007;104(39):15549-54. Epub Sep. 17, 2007.
Chandran et al., Animal cell invasion by a large nonenveloped virus: reovirus delivers the goods. Trends Microbiol. Aug. 2003;11(8):374-82.
Chiu et al., Visualizing a correlation between siRNA localization, cellular uptake, and RNAi in living cells. Chem Biol. Aug. 2004;11(8):1165-75.
Dassie et al., Systemic administration of optimized aptamer-siRNA chimeras promotes regression of PSMA-expressing tumors. Nat Biotechnol. Sep. 2009;27(9):839-49. Epub Aug. 23, 2009.
Davis et al., Evidence of RNAi in humans from systemically administered siRNA via targeted nanoparticles. Nature. Apr. 15, 2010;464(7291):1067-70. Epub Mar. 21, 2010.
Eguchi et al., Efficient siRNA delivery into primary cells by a peptide transduction domain-dsRNA binding domain fusion protein. Nat Biotechnol. Jun. 2009;27(6):567-71. Epub May 17, 2009.
Eguchi et al., siRNA delivery using peptide transduction domains. Trends Pharmacol Sci. Jul. 2009;30(7):341-5. Epub Jun. 21, 2009.
Eiden, Fusion polypeptides that inhibit exocytosis: fusing aptamer and cell-penetrating peptide technologies and pharmacologies. Mol Pharmacol. Apr. 2005;67(4):980-2. Epub Jan. 26, 2005.
Elbashir et al., Duplexes of 21-nucleotide RNAs mediate RNA interference in cultured mammalian cells. Nature. May 24, 2001;411(6836):494-8.
Fire et al., Potent and specific genetic interference by double-stranded RNA in *Caenorhabditis elegans*. Nature. Feb. 19, 1998;391(6669):806-11.
Fogal et al., Mitochondrial p32 protein is a critical regulator of tumor metabolism via maintenance of oxidative phosphorylation. Mol Cell Biol. Mar. 2010;30(6):1303-18. Epub Jan. 25, 2010.
Fogal et al., Mitochondrial/cell-surface protein p32/gC1qR as a molecular target in tumor cells and tumor stroma. Cancer Res. Sep. 1, 2008;68(17):7210-8.
Henke et al., Peptide-conjugated antisense oligonucleotides for targeted inhibition of a transcriptional regulator in vivo. Nat Biotechnol. Jan. 2008;26(1):91-100. Epub Jan. 6, 2008.
Hiwasa et al., Increase in the synthesis of a Mr 32,000 protein in BALB/c 3T3 cells after treatment with tumor promoters, chemical carcinogens, metal salts, and heat shock. Cancer Res. May 1986;46(5):2474-81.
Hogle, Poliovirus cell entry: common structural themes in viral cell entry pathways. Annu Rev Microbiol. 2002;56:677-702. Epub Jan. 30, 2002.

(Continued)

*Primary Examiner* — Kimberly Chong
(74) *Attorney, Agent, or Firm* — Wolf, Greenfield & Sacks, P.C.

(57) ABSTRACT

Aspects of the invention provide compositions and methods for delivering nucleic acids to target cells.

31 Claims, 43 Drawing Sheets

(56) References Cited

OTHER PUBLICATIONS

Hooper et al., Monoclonal antibodies to reovirus sigma 1 and mu 1 proteins inhibit chromium release from mouse L cells. J Virol. Jan. 1996;70(1):672-7.
Hopkins et al., The druggable genome. Nat Rev Drug Discov. Sep. 2002;1(9):727-30.
Hornung et al., Sequence-specific potent induction of IFN-alpha by short interfering RNA in plasmacytoid dendritic cells through TLR7. Nat Med. Mar. 2005;11(3):263-70. Epub Feb. 20, 2005.
Huang et al., Claudin-3 gene silencing with siRNA suppresses ovarian tumor growth and metastasis. Proc Natl Acad Sci U S A. Mar. 3, 2009;106(9):3426-30. Epub Feb. 10, 2009.
Ishihara et al., Intracellular delivery of siRNA by cell-penetrating peptides modified with cationic oligopeptides. Drug Deliv. Apr. 2009;16(3):153-9.
Jain, Delivery of molecular and cellular medicine to solid tumors. Control Release. Apr. 30, 1998;53(1-3):49-67.
Jain, Delivery of molecular and cellular medicine to solid tumors. Adv Drug Deliv Rev. Mar. 1, 2001;46(1-3):149-68.
Jemal et al., Cancer statistics, 2009. CA Cancer J Clin. Jul.-Aug. 2009;59(4):225-49. Epub May 27, 2009.
Jiang et al., Crystal structure of human p32, a doughnut-shaped acidic mitochondrial matrix protein. Proc Natl Acad Sci U S A. Mar. 30, 1999;96(7):3572-7.
Judge et al., Sequence-dependent stimulation of the mammalian innate immune response by synthetic siRNA. Nat Biotechnol. Apr. 2005;23(4):457-62. Epub Mar. 20, 2005.
Karmali et al., Targeting of albumin-embedded paclitaxel nanoparticles to tumors. Nanomedicine: Mar. 2009;5(1):73-82. Epub Oct. 1, 2008.
Kumar et al. T cell-specific siRNA delivery suppresses HIV-1 infection in humanized mice. Cell. Aug. 22, 2088;134(4):577-86. Epub Aug. 7, 2008.
Kumar et al., Transvascular delivery of small interfering RNA to the central nervous system. Nature. Jul. 5, 2007;448(7149):39-43. Epub Jun. 17, 2007. Supplementary data included.
Laakkonen et al., A tumor-homing peptide with a targeting specificity related to lymphatic vessels. Nat Med. Jul. 2002;8(7):751-5. Epub Jun. 10, 2002.
Laakkonen et al., Antitumor activity of a homing peptide that targets tumor lymphatics and tumor cells. Proc Natl Acad Sci U S A. Jun. 22, 2004;101(25):9381-6. Epub Jun. 14, 2004.
Lin et al., Skp2 targeting suppresses tumorigenesis by Arf-p53-independent cellular senescence. Nature. Mar. 18, 2010;464(7287):374-9.
Macdiarmid et al., Sequential treatment of drug-resistant tumors with targeted minicells containing siRNA or a cytotoxic drug. Nat Biotechnol. Jul. 2009;27(7):643-51. Epub Jun. 28, 2009.
Marques et al., Activation of the mammalian immune system by siRNAs. Nat Biotechnol. Nov. 2005;23(11):1399-405.
Maurer-Stroh et al., Myristoylation of viral and bacterial proteins. Trends Microbiol. Apr. 2004;12(4):178-85.
Meade et al., Enhancing the cellular uptake of siRNA duplexes following noncovalent packaging with protein transduction domain peptides. Adv Drug Deliv Rev. Mar. 1, 2008;60(4-5):530-6. Epub Oct. 22, 2007.
Meade et al., Exogenous siRNA delivery using peptide transduction domains/cell penetrating peptides. Adv Drug Deliv Rev. Mar. 30, 2007;59(2-3):134-40. Epub Mar. 15, 2007.
Memarzadeh et al., Advances in the management of epithelial ovarian cancer. J Reprod Med. Jul. 2001;46(7):621-9; discussion 629-30.
Montet et al., Multivalent effects of RGD peptides obtained by nanoparticle display. J Med Chem. Oct. 5, 2006;49(20):6087-93.
Muratovska et al., Conjugate for efficient delivery of short interfering RNA (siRNA) into mammalian cells. FEBS Lett. Jan. 30, 2004;558(1-3):63-8.
Myrberg et al., Design of a tumor-homing cell-penetrating peptide. Bioconjug Chem. Jan. 2008;19(1):70-5. Epub Nov. 15, 2007.

Park et al., Cooperative nanomaterial system to sensitize, target, and treat tumors. Proc Natl Acad Sci U S A. Jan. 19, 2010;107(3):981-6. Epub Dec. 28, 2009.
Pasqualini et al., Organ targeting in vivo using phage display peptide libraries. Nature. Mar. 28, 1996;380(6572):364-6.
Polverino et al., Survival and prognostic factors of women with advanced ovarian cancer and complete response after a carboplatin-paclitaxel chemotherapy. Gynecol Oncol. Nov. 2005;99(2):343-7. Epub Jul. 26, 2005.
Ren et al., Targeted Tumor-Penetrating siRNA Nanocomplexes for Credentialing the Ovarian Cancer Oncogene ID4. Sci Transl Med. Aug. 15, 2012;4(147):147ra112.
Rubinstein et al., Receptor for the globular heads of C1q (gC1q-R, p33, hyaluronan-binding protein) is preferentially expressed in adenocarcinoma cells. Int J Cancer. Jul. 10, 2004;110(5):741-50.
Ruoslahti et al., Targeting of drugs and nanoparticles to tumors. J Cell Biol. Mar. 22, 2010;188(6):759-68. Epub Mar. 15, 2010.
Ruoslahti, Drug targeting to specific vascular sites. Drug Discov Today. Nov. 15, 2002;7(22):1138-43.
Ruoslahti, Specialization of tumour vasculature. Nat Rev Cancer. Feb. 2002;2(2):83-90.
Satchi-Fainaro et al., Targeting angiogenesis with a conjugate of HPMA copolymer and TNP-470. Nat Med. Mar. 2010;10(3):255-61. Epub Feb. 22, 2004.
Skehel et al., Receptor binding and membrane fusion in virus entry: the influenza hemagglutinin. Annu Rev Biochem. 2000;69:531-69.
Song et al., Antibody mediated in vivo delivery of small interfering RNAs via cell-surface receptors. Nat Biotechnol. Jun. 2005;23(6):709-17. Epub May 22, 2005.
Soutschek et al., Therapeutic silencing of an endogenous gene by systemic administration of modified siRNAs. Nature. Nov. 11, 2004;432(7014):173-8.
Sugahara et al., Coadministration of a tumor-penetrating peptide enhances the efficacy of cancer drugs. Science. May 21, 2010;328(5981):1031-5. Epub Apr. 8, 2010.
Sugahara et al., Tissue-penetrating delivery of compounds and nanoparticles into tumors. Cancer Cell. Dec. 8, 2009;16(6):510-20.
TCGA Research Network, Comprehensive genomic characterization defines human glioblastoma genes and core pathways. Nature. Oct. 23, 2008;455(7216):1061-8. Epub Sep. 4, 2008.
Teesalu et al., C-end rule peptides mediate neuropilin-1-dependent cell, vascular, and tissue penetration. Proc Natl Acad Sci U S A. Sep. 22, 2009;106(38):16157-62. Epub Sep. 2, 2009.
Turner et al., RNA targeting with peptide conjugates of oligonucleotides, siRNA and PNA. Blood Cells Mol Dis. Jan.-Feb. 2007;38(1):1-7. Epub Nov. 17, 2006.
Veldhoen et al., Cellular delivery of small interfering RNA by a non-covalently attached cell-penetrating peptide: quantitative analysis of uptake and biological effect. Nucleic Acids Res. 2006;34(22):6561-73. Epub Nov. 28, 2006.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Whitehead et al., Knocking down barriers: advances in siRNA delivery. Nat Rev Drug Discov. Feb. 2009;8(2):129-38.
Wolfrum et al., Mechanisms and optimization of in vivo delivery of lipophilic siRNAs. Nat Biotechnol. Oct. 2007;25(10):1149-57. Epub Sep. 16, 2007.
Zimmermann et al., RNAi-mediated gene silencing in non-human primates. Nature. May 4, 2006;441(7089):111-4. Epub Mar. 26, 2006.
International Preliminary Report on Patentability mailed Oct. 18, 2012 for PCT/US2011/031469.
Nijhawan et al., Cancer vulnerabilities unveiled by genomic loss. Cell. Aug. 17, 2012;150(4):842-54.
Ren et al., Identification and characterization of receptor-specific peptides for siRNA delivery. ACS Nano. Oct. 23, 2012;6(10):8620-31. Epub Aug. 27, 2012.

* cited by examiner

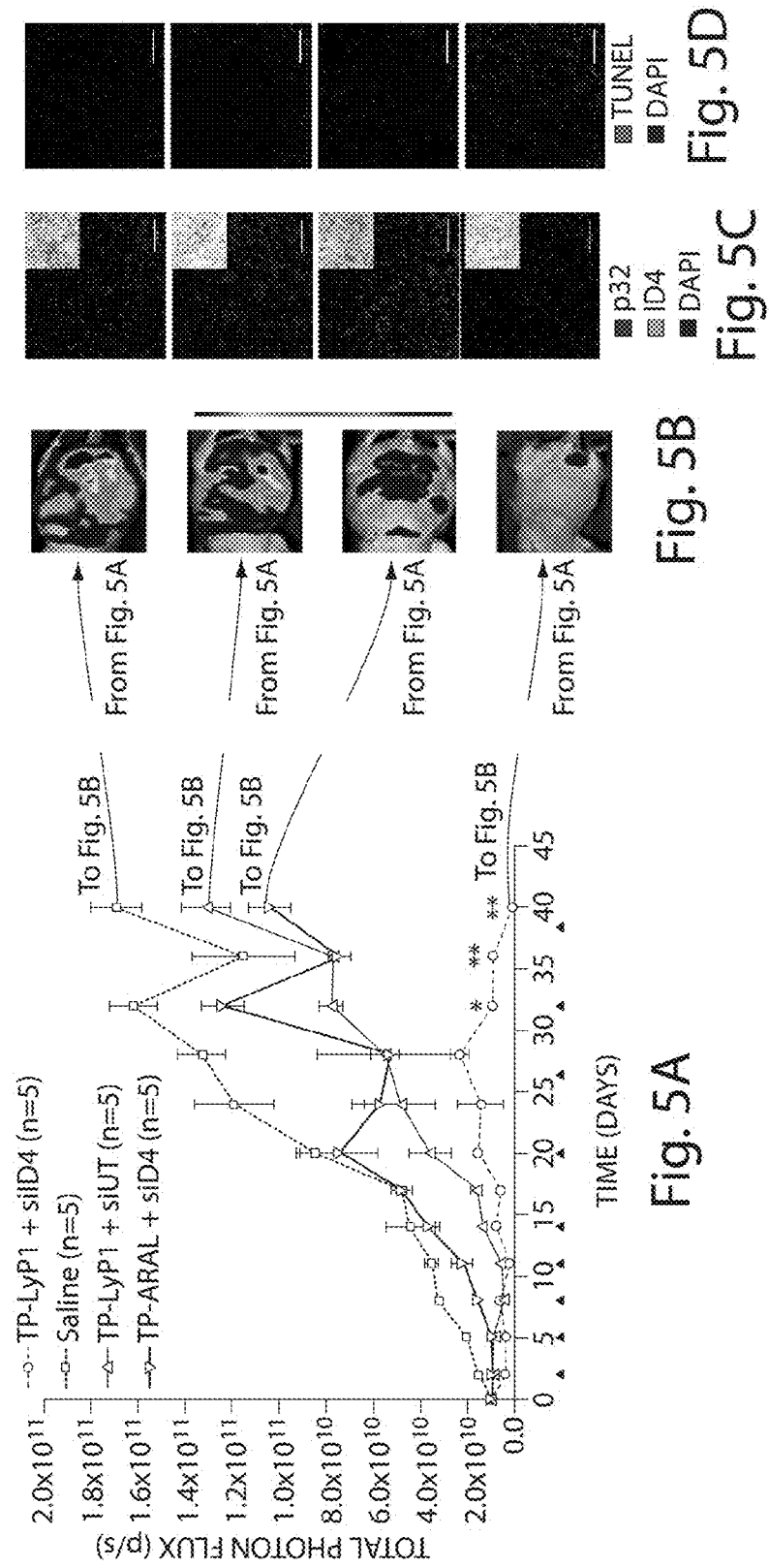

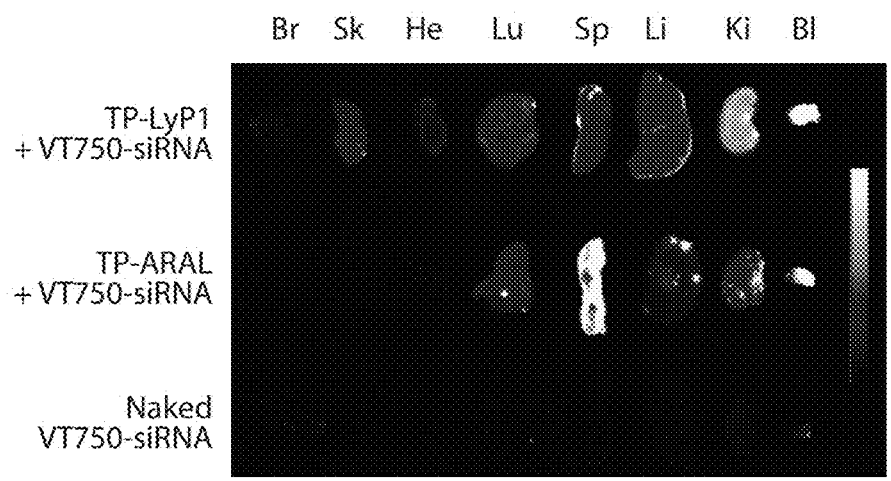
Fig. 11A1
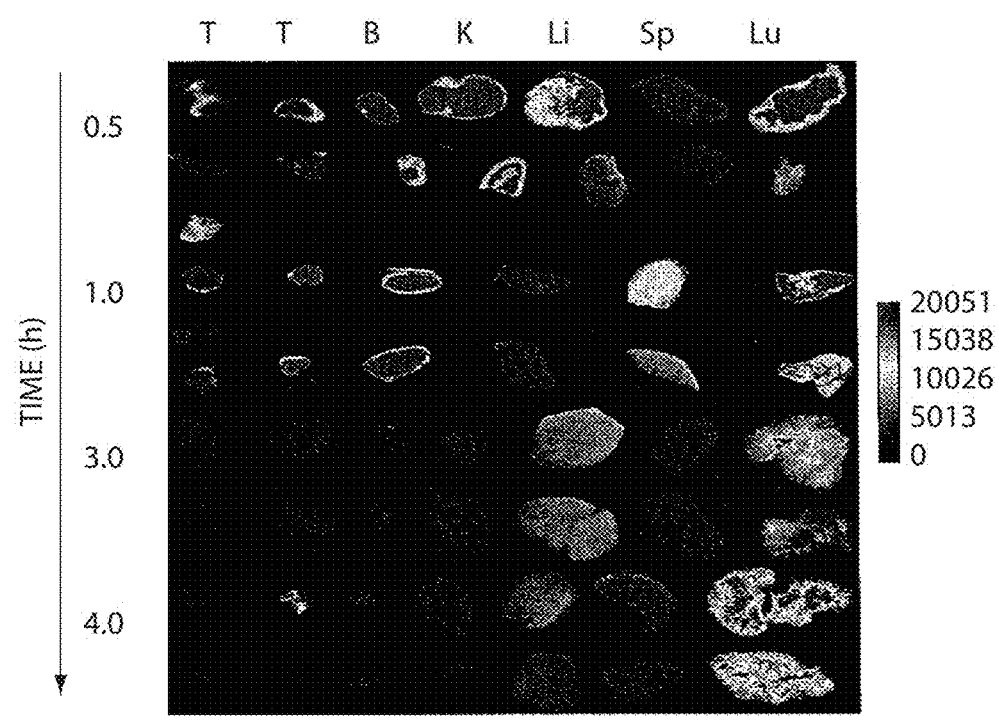
Fig. 11A2

TARGETED DELIVERY OF NUCLEIC ACIDS

RELATED APPLICATIONS

The present application claims the benefit under 35 U.S.C. 119(e) of the filing date of U.S. Provisional Patent Application 61/321,157, filed on Apr. 6, 2010, the disclosure of which is incorporated herein in its entirety.

FEDERALLY SPONSORED RESEARCH

This invention was made with Government support under Grant No. U54 CA119349, awarded by the National Institute of Health. The Government has certain rights in this invention.

BACKGROUND OF INVENTION

Targeted delivery of therapeutics such as siRNA may improve tumor treatment by increasing efficacy and minimizing side effects [see for example, Jain, R. K. Delivery of molecular and cellular medicine to solid tumors. *J Control Release* 53, 49-67, (1998); Jain, R. K. Delivery of molecular and cellular medicine to solid tumors. *Adv Drug Deliv Rev* 46, 149-168, (2001); Ruoslahti, E. Drug targeting to specific vascular sites. *Drug Discov Today* 7, 1138-1143, (2002); Ruoslahti, E. Specialization of tumour vasculature. *Nat Rev Cancer* 2, 83-90, (2002); and, Jain, R. K. Delivery of molecular and cellular medicine to solid tumors. *J Control Release* 53, 49-67, (1998); Satchi-Fainaro, R. et al. Targeting angiogenesis with a conjugate of HPMA copolymer and TNP-470. *Nat Med* 10, 255-261, (2004)].

Approaches to target siRNA in vivo have been challenging due to their rapid clearance, susceptibility to serum nucleases, endosomal entrapment, and stimulation of innate immunity [Whitehead, K. A., Langer, R. & Anderson, D. G. Knocking down barriers: advances in siRNA delivery. *Nat Rev Drug Discov* 8, 129-138, (2009)].

High-throughput technologies such as in vivo phage display have selected targeting peptides for a diversity of molecular targets [Akerman, M. E., Chan, W. C., Laakkonen, P., Bhatia, S. N. & Ruoslahti, E. Nanocrystal targeting in vivo. *Proc Natl Acad Sci USA* 99, 12617-12621, (2002); and Pasqualini, R. & Ruoslahti, E. Organ targeting in vivo using phage display peptide libraries. *Nature* 380, 364-366, (1996)], while whole-genome sequencing has provided an integrated dataset of genetic alterations in human cancer [Comprehensive genomic characterization defines human glioblastoma genes and core pathways. *Nature* 455, 1061-1068, (2008)]. However, a unifying technology that is equally high-throughput and efficient is required to validate these hits in vivo and translate them into clinically meaningful therapies.

SUMMARY OF INVENTION

Aspects of the invention relate to novel approaches for targeting nucleic acids (e.g., siRNA molecules) for in vivo delivery. In some embodiments, polypeptides having to certain functional and structural properties are used as carrier molecules that are effective to i) target nucleic acids to one or more particular cell types and ii) deliver the targeted nucleic acids to the appropriate intracellular location. In some embodiments, a tandem polypeptide that comprises a cell-specific targeting domain fused to a protein transduction domain is useful to deliver nucleic acid in vivo or in vitro. The tandem polypeptide can be complexed with one or more nucleic acids to be delivered. The complex can be administered to an organism for in vivo delivery, or contacted to cells or cell-free systems for ex vivo analysis. Compositions and methods of the invention can be used for diagnostic, therapeutic, and/or research and development applications as described herein. It was surprising that effective extravascular cell-specific delivery can be obtained using a tandem peptide having both a tumor penetrating homing domain and a non-cell specific transduction domain.

Aspects of the invention relate to the surprising finding that non-cell-specific protein transduction properties of certain protein transduction domains (PTDs) can be masked effectively in the context of a peptide/nucleic acid complex that also contains a cell-specific targeting domain. This provides for effective cellular penetration (and nucleic acid delivery) that is limited to one or more target cell types of interest. In some embodiments, a homing domain (e.g., a cyclic peptide based homing domain) can be used in conjunction with a positively charged protein transduction domain that both binds to nucleic acid and provides cell transduction properties to help deliver the nucleic acid to the cytosol of a target cell. In some embodiments, this process involves protecting the nucleic acid from degradation and/or effectively releasing the nucleic acid from within the endosome of the target cell. In some embodiments, cell-targeting specificity is improved by using PTDs or portions thereof that are characterized by having a positive charge that is below a threshold level, wherein the threshold level corresponds to a level above which the non-cell-specific transduction properties of the PTD dominate relative to the cell-specific targeting properties of the targeting domain. In some embodiments, the ratio of negative charge (e.g., from the nucleic acid) to positive charge (e.g., in the PTD domain) of a peptide/nucleic acid complex can impact the strength of the non-cell-specific transduction properties of the complex.

Accordingly, aspects of the invention relate to compositions and methods for delivering one or more nucleic acids to cellular targets. In some embodiments, a nucleic acid is delivered in a complex that includes a targeting polypeptide and a nucleic acid to binding polypeptide, wherein the targeting polypeptide comprises a motif that binds to a cellular target, and wherein the nucleic acid binding polypeptide comprises a motif that binds to the nucleic acid. In some embodiments, the nucleic acid binding motif binds to the nucleic acid with sufficient affinity to protect the nucleic acid from degradation during delivery, but with binding characteristics that allow the nucleic acid to be effectively released at the site of delivery (e.g., within a target cell). In some embodiments, a delivery complex includes a protein transduction domain having a motif that promotes fusion with a membrane (e.g., a cell membrane and/or an intracellular membrane) and enhances delivery of the nucleic acid (e.g., to an intracellular location within a target cell).

Accordingly, aspects of the invention provide a delivery platform that is modular and can be adapted to deliver any nucleic acid to any cell of interest. In some embodiments, the targeting domain, nucleic acid binding domain, and/or protein transduction domain are all part of a single polypeptide (e.g., a chimeric or fusion polypeptide). A polypeptide (e.g., a single polypeptide) may be combined with a single nucleic acid (e.g., a single nucleic acid molecule) and the combination can be targeted to a desired delivery site. However, it should be appreciated that in some embodiments, the different polypeptides may be associated with a particle (e.g., a nanoparticle) that may contain one or more nucleic acids. Accordingly, in some embodiments, the polypeptides assemble into light-scattering complexes or particles upon complexation with nucleic acid molecules. A complex/particle may be protein-based, lipid-based, polymer-based, or any combination thereof, or any other type of particle, as aspects of the invention are not limited in this respect.

In some embodiments, a multimeric (e.g., multivalent) complex may be formed by mixing a nucleic acid (e.g., an siRNA) with a polypeptide of the invention. The multimeric complex may be used to deliver the nucleic acid to a target cell for diagnostic and/or therapeutic applications. In some embodiments, the polypeptide may include a tumor-specific binding motif (e.g., a tumor-specific cyclic homing domain) and a cell penetrating motif to promote efficient delivery of a nucleic acid to a specific tumor cell. Accordingly, in some embodiments the invention provides a tumor-specific and highly efficient siRNA delivery platform that includes a cyclic homing domain-cell penetrating domain fusion tandem peptide. Upon complexation with siRNA, the resulting to nanocomplex is stable, non-immunostimulatory, displays homing peptides in a multivalent fashion that increases their binding avidity and delivers siRNA to the cytosol of tumor cells through receptor-specific interactions. Upon administration to a subject (e.g., a human subject), this nanocomplex can home to tumor cells of interest and silence target genes in the tumor cells. Any tumor cells may be targeted using appropriate targeting domains. For example, metastatic peritoneal tumors cells may be targeted. However, other tumor cells may be targeted as aspects of the invention are not limited in this respect.

Accordingly, the technology platform of the invention is useful to target the delivery of nucleic acid therapeutics to any subsets of cells in vivo. It is also modular, thus broadly applicable to different types of tissues and diseases, simply by varying the targeting domain (e.g., using different homing peptide domains). In comparison, existing methods of siRNA delivery are not readily generalized, lack tissue specificity, and/or are large, difficult to manufacture, and/or immunotoxic.

Approaches to delivering of siRNA in vivo have focused on development of carriers such as antibodies, lipids, and peptides which passively escape blood vessels in order to reach target cells, yet have shown limited capacities to efficiently deliver therapeutics to specific sites of interest (e.g., to extravascular cancer cells located throughout a tumor parenchyma).

In some embodiments, aspects of the invention relate to siRNA delivery (e.g., cell-specific siRNA delivery). In some embodiments, a targeted tumor-penetrating nanocomplex is capable of precisely delivering nucleic acid (e.g., siRNA) deep into the tumor parenchyma. In some embodiments, non-limiting examples of nanocomplexes that include TP-LyP1 tandem peptides and ID4 siRNA are able to potently impede the growth of aggressive, metastatic ovarian tumors. Other tissue or tumor-penetrating domains (e.g., iRGD or others) may be used to deliver nucleic acid to tissue cites (e.g., tumor sites). Also, other nucleic acids (e.g., other siRNAs or a combination of siRNAs) may be used to silence different genes. The role of tumor homing in this system stands in stark contrast to other in vivo siRNA delivery methods that lack tumor penetration domains, systems that require direct conjugation and custom synthesis, and carriers where target cells cannot be molecularly specified.

Aspects of the invention provide a modular platform that can be adapted to provide different peptide targeting and/or nucleic acid (e.g., siRNA) delivery functions. Further, by leveraging new discoveries relating to the amplification of transvascular transport and the diversity of tumor-penetrating ligands, the tumor and membrane penetrating domains of this tandem peptide platform can be varied independently from each other, enabling broad access of cellular targets (e.g., parenchymal tumor cells) to RNA-based therapeutics.

In some embodiments, peptide technology of the invention allows for rapid in vivo validation of novel oncogene targets in tumor cells that are identified from large-scale genomic screens. Therefore, tandem peptide-directed delivery of siRNA as described herein provides a new avenue of therapeutic treatment of human cancers.

In some embodiments, compositions of the invention may be delivered to a subject in an amount sufficient to promote a desired change (e.g., gene silencing, expression, etc., depending on the application of interest). In some embodiments, a composition may be provided to a subject at a dose of from about 0.1 mg/kg to 100 mg/kg body weight (e.g., about 1 mg/kg, about 2.5 mg/kg, about 5 mg/kg, about 10 mg/kg, about 25 mg/kg, about 50 mg/kg, or any suitable lower, higher, or intermediate dose). In some embodiments, a subject may receive chronic administrations of a therapeutic composition. A subject shall mean a human or vertebrate animal or mammal including but not limited to a dog, cat, horse, cow, pig, sheep, goat, turkey, chicken, and primate, e.g., monkey. In some embodiments, a subject may have a disease or disorder that can be treated (e.g., using a cell-targeted delivery of a therapeutic nucleic acid).

Accordingly, aspects of the invention relate to a composition comprising a polypeptide comprising a first cell-targeting domain and a second cell-penetrating domain, and a nucleic acid, wherein the nucleic acid is reversibly associated with the second cell-penetrating domain due to the presence of two or more basic amino acids within the second cell penetrating domain, and wherein the number of basic amino acids within the second cell penetrating domain is below a threshold level of amino acids above which the polypeptide targets cells non-specifically. It should be appreciated that the compositions described herein as comprising or including one or more different domains and/or nucleic acids also can consist of only those domains and/or nucleic acids.

These and other aspects of the invention are described in more detail herein.

Figure 1A:
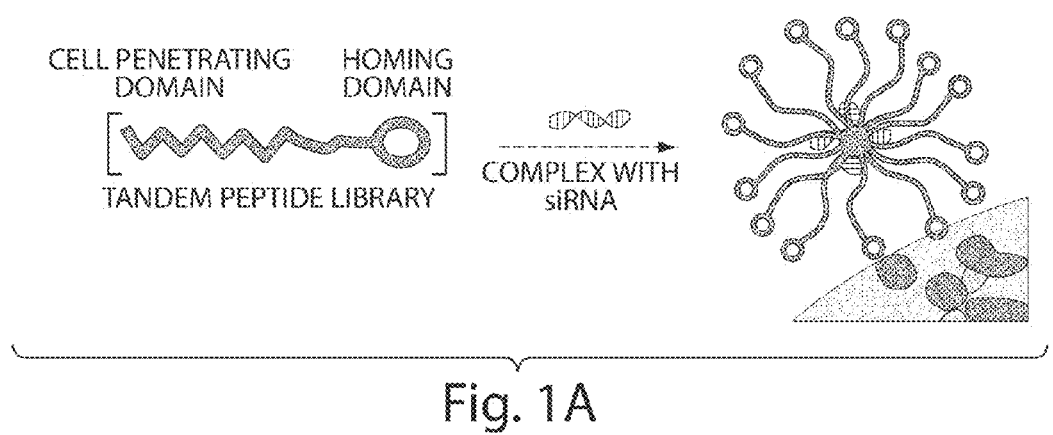
FIG. 1A illustrates a non-limiting embodiment of a polypeptide comprising a first and second domain.
Figure 1B:
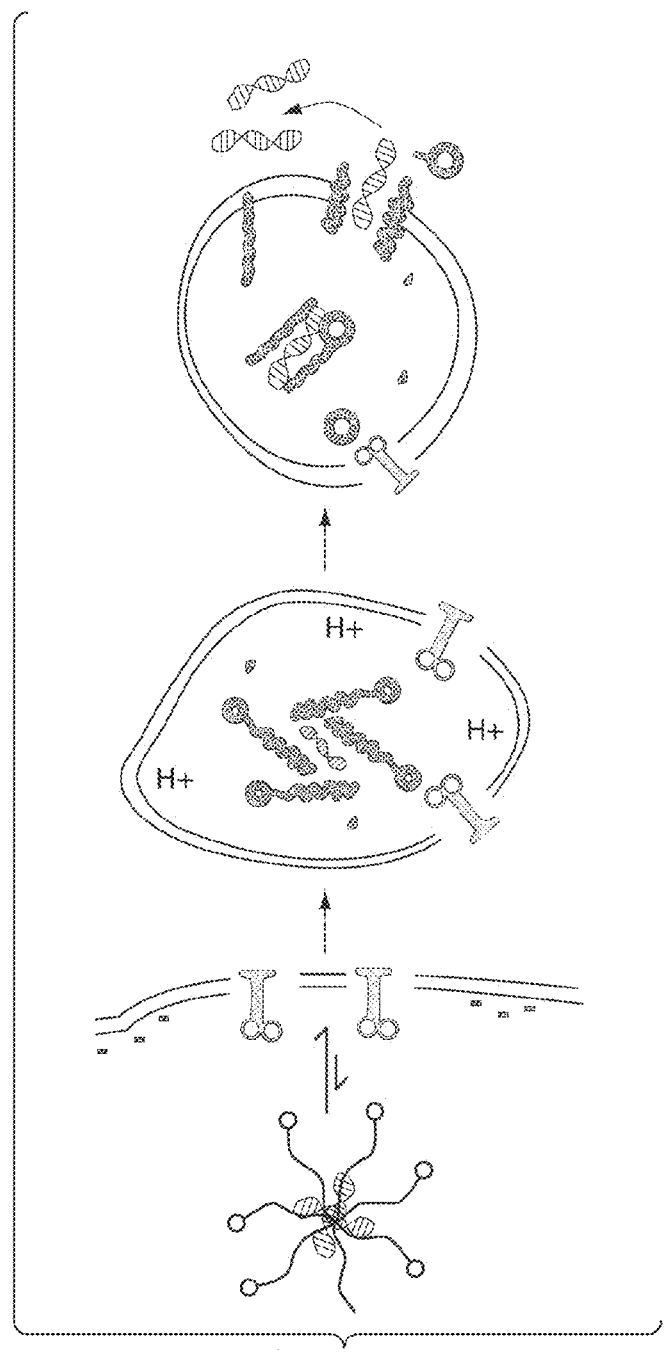
FIG. 1B illustrates a non-limiting embodiment of a nucleic acid delivery mediated by a polypeptide of FIG. 1A.
Figure 1C:
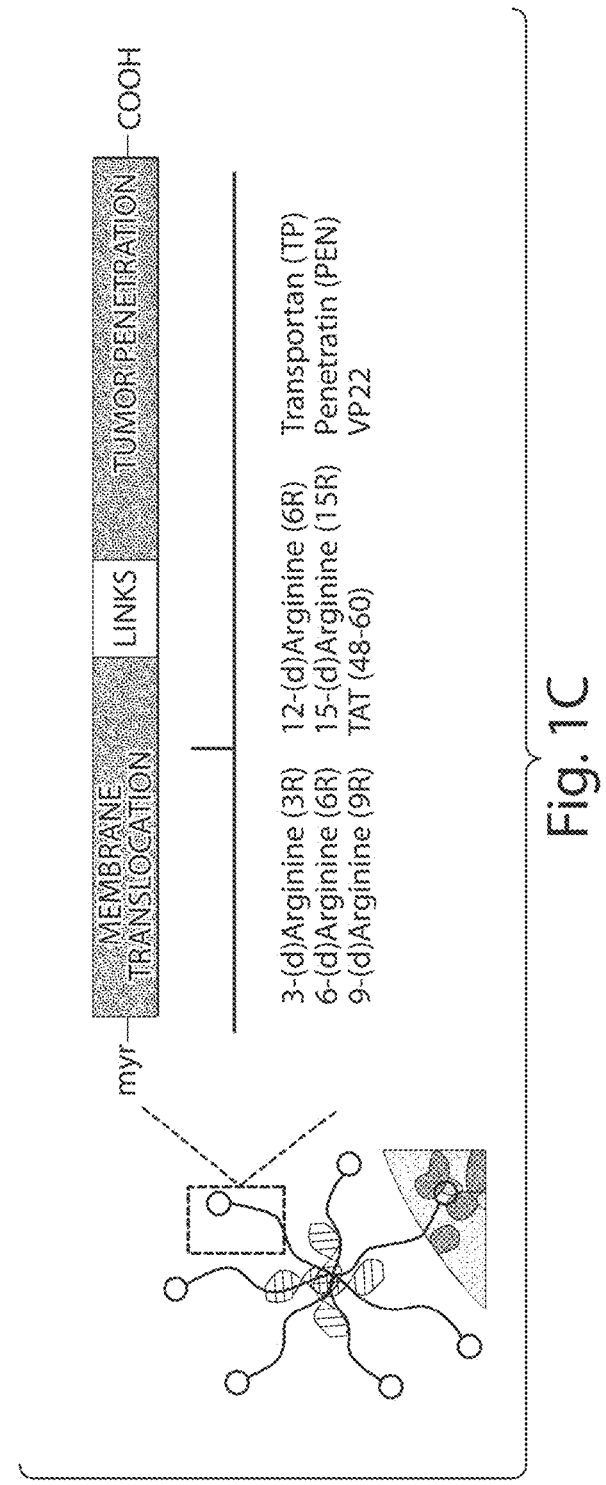
FIG. 1C shows a schematic representation of tandem peptides bearing a membrane translocation domain, a tumor penetrating domain, and a linker.
Figure 5E:
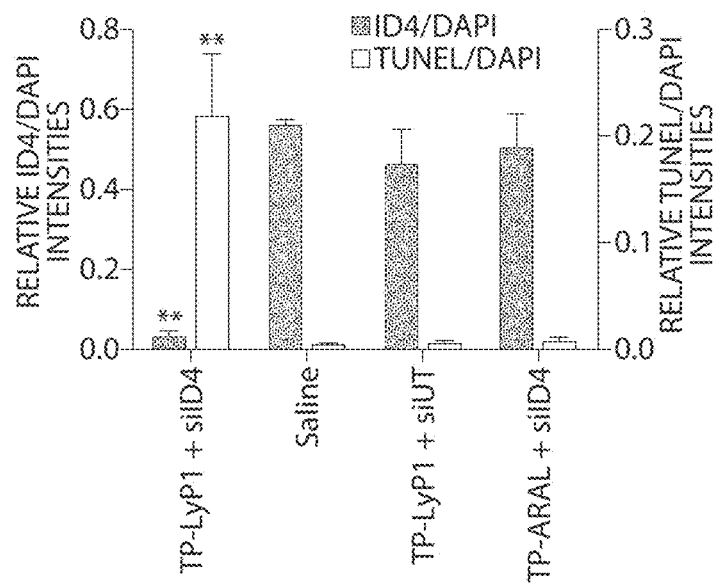
FIG. 5E is a quantitative analysis of ID4 (white bars) and TUNEL (black bars) staining intensities per cell relative to number of cells counterstained with DAPI using data from 5 separate sections from a mouse from each cohort. Statistical analyses were performed using ANOVA; Error bars, mean±SEM. ** p<0.01.
Figure 5F:
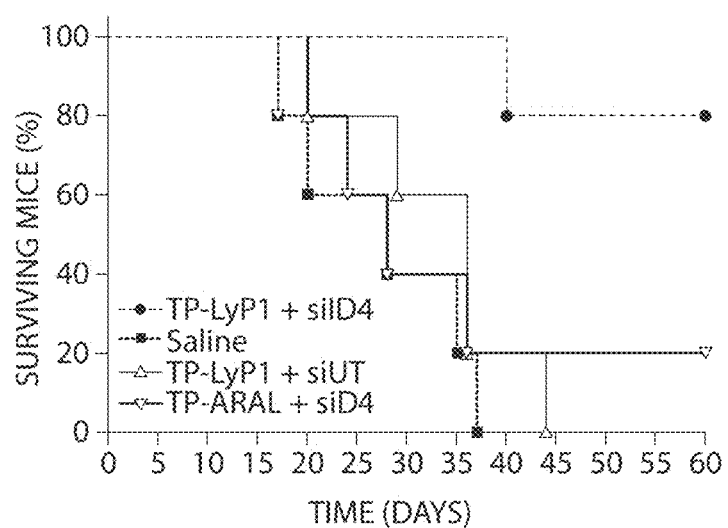
FIG. 5F is a Kaplan-Meier plot of overall survival of different treatment groups after initiation of TP-LyP1/ID4 siRNA treatment (n=5 for each group). All scale bars, 50 μm.
Figure 5G:
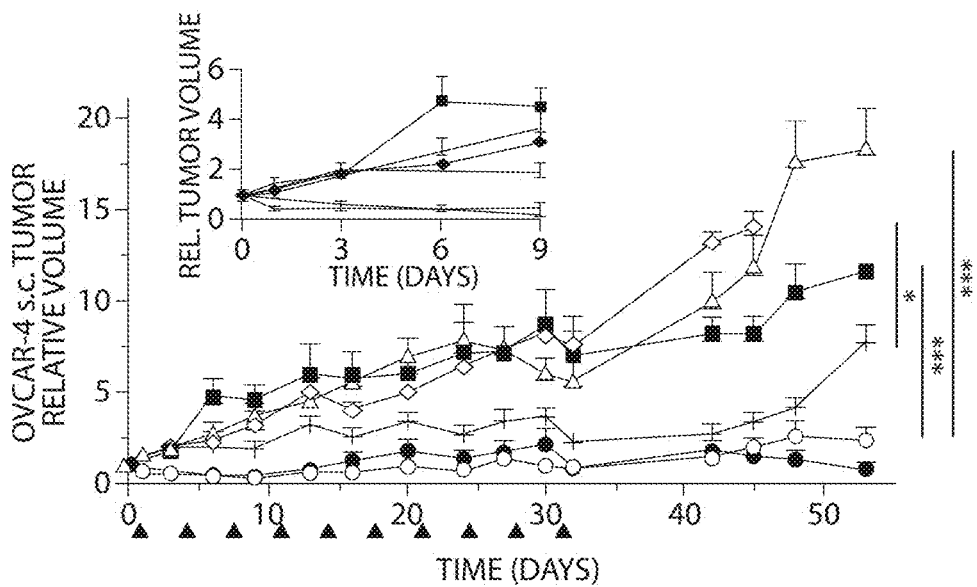
FIG. 5G shows treatment of cohorts of mice bearing subcutaneous OVCAR-4 ovarian tumor xenografts with TP-LyP1/siID4 nanocomplexes. Treatment occurred every 3 d for 30 d at 1 mg/kg siRNA/injection. Tumor growth was quantified by digital caliper measurements of tumor size for 60 d. One cohort received TP-LyP1/siClaudin-3 nanocomoplexes as a comparison. Control cohorts received TP-LyP1 peptide alone, saline, or nanocomplex carrying an irrelevant siRNA (siUT). RNAi treatment period is shaded in gray. The relative tumor volumes from the first 9 days are enlarged for ease of comparison (inset)
Figure 5H:
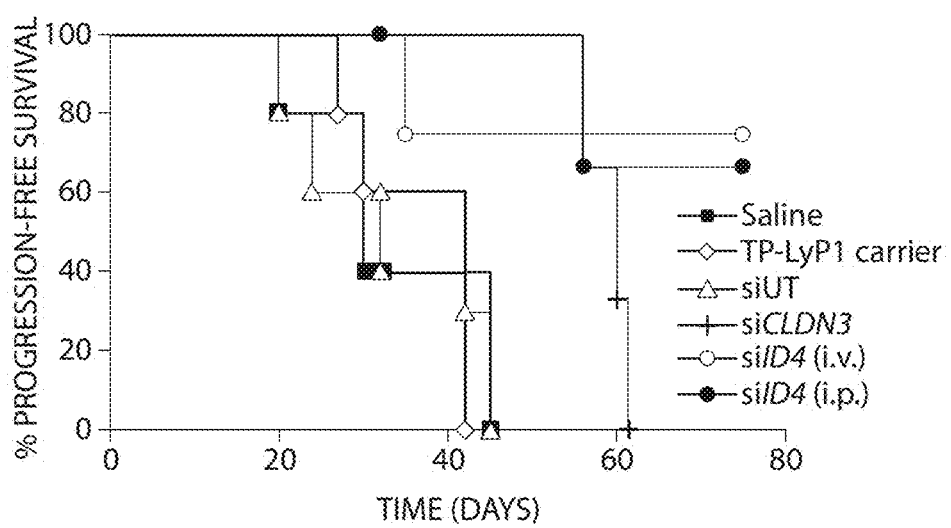
FIG. 5A demonstrates total tumor growth followed for 40 d post establishment of orthotopic metastatic human ovarian tumor in the intraperitoneal space. Intraperitoneal treatment of peptide/ID4 siRNA formulations was started on day 3 and was repeated twice weekly for 2 weeks, then once weekly for 3 weeks (5 mg/kg siRNA per injection per mouse). Control cohorts received phosphate-buffered saline (PBS), peptide/siRNA against GFP, or untargeted peptide/ID4 siRNA at the same dose. Error bars indicate±SEM. (n=5); *p<0.05; **p<0.01.
FIG. 5B shows representative whole-animal bioluminescence images from the 4 cohorts.
FIG. 5C shows tumor sections harvested on day 40 stained for p32 and ID4 by immunofluorescence and IHC (inset). Treatment with TP-LyP1/siID4 decreased ID4 expression in remaining tumor cells.
FIG. 5D shows that TP-LyP1/siID4 treated tumor stain highly positive for TUNEL indicating tumor cells undergoing apoptosis. Control tumors did not show significant staining.
Figure 5I:
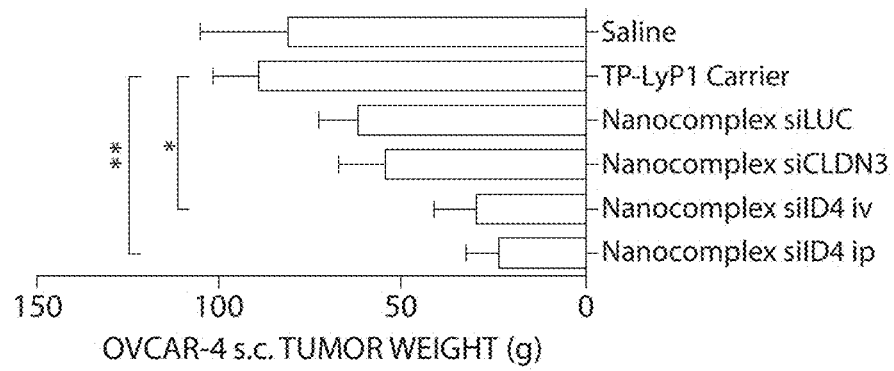
Figure 5J:
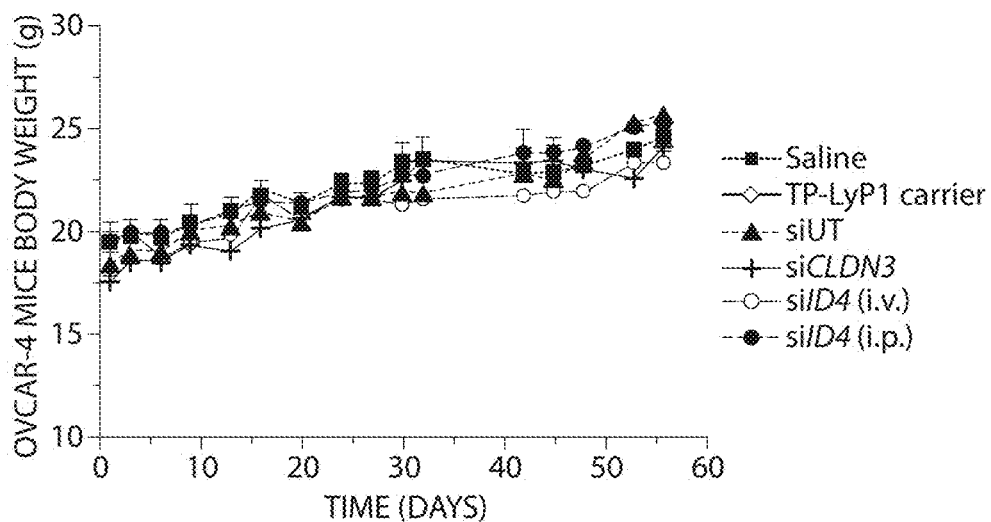
Figure 5K:
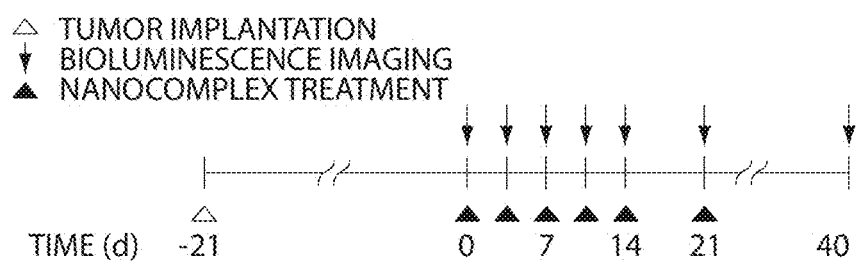
Figure 6A:
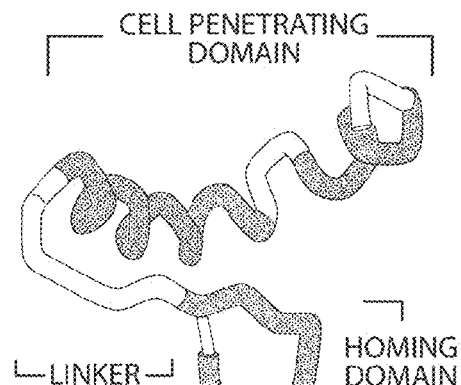
Figure 6B:
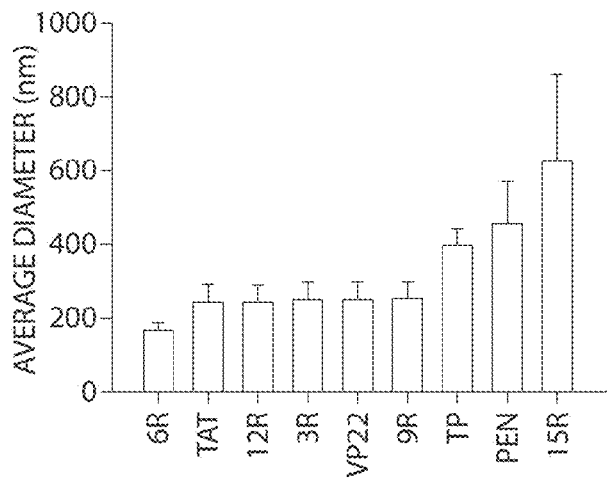
Figure 6C:
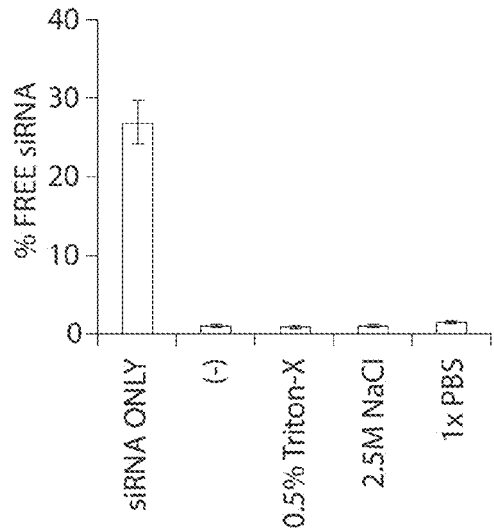
Figure 7:
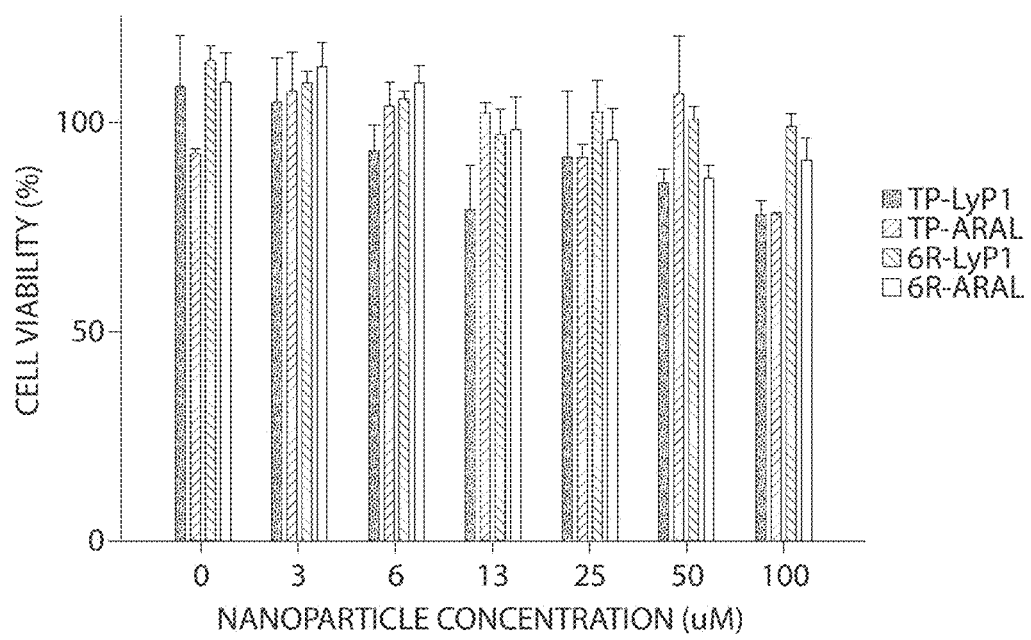
Figure 8A:
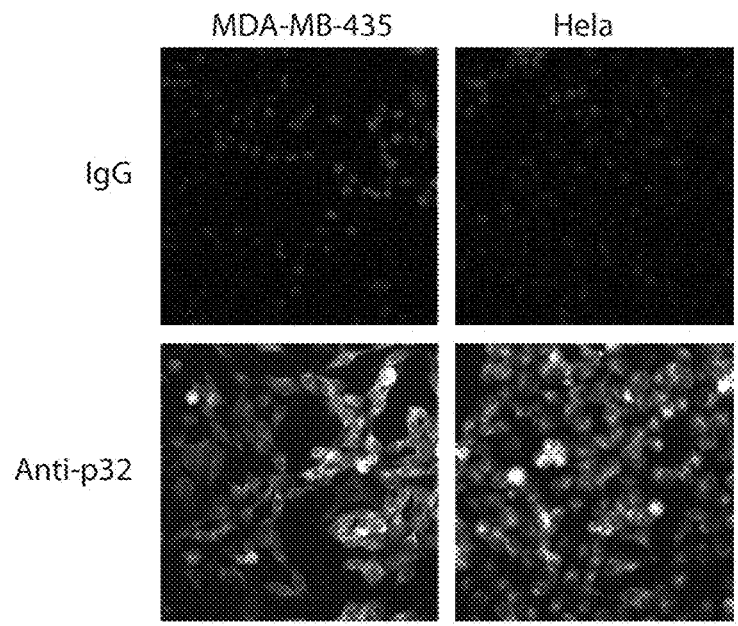
Figure 8B:
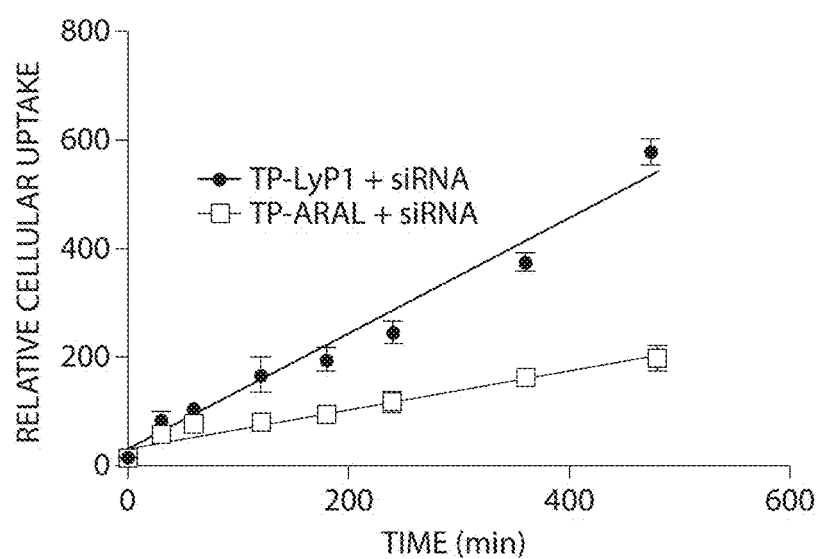
Figure 9A:
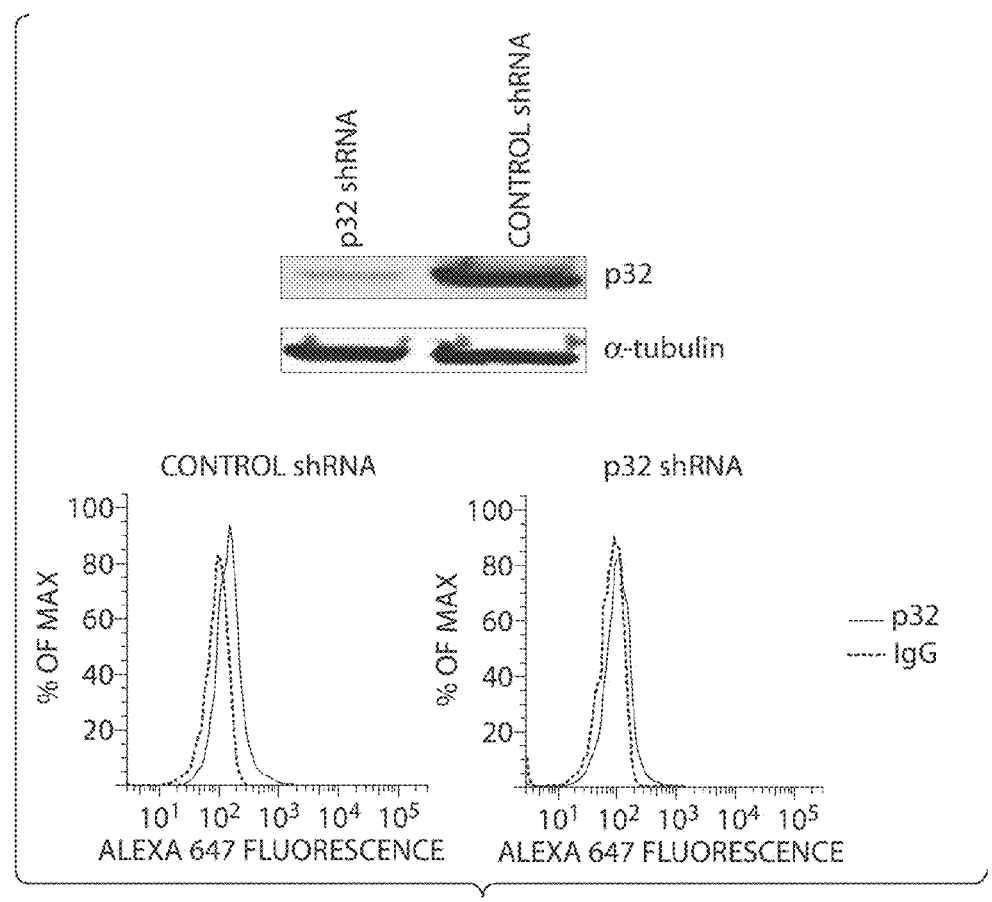
Figure 9B:
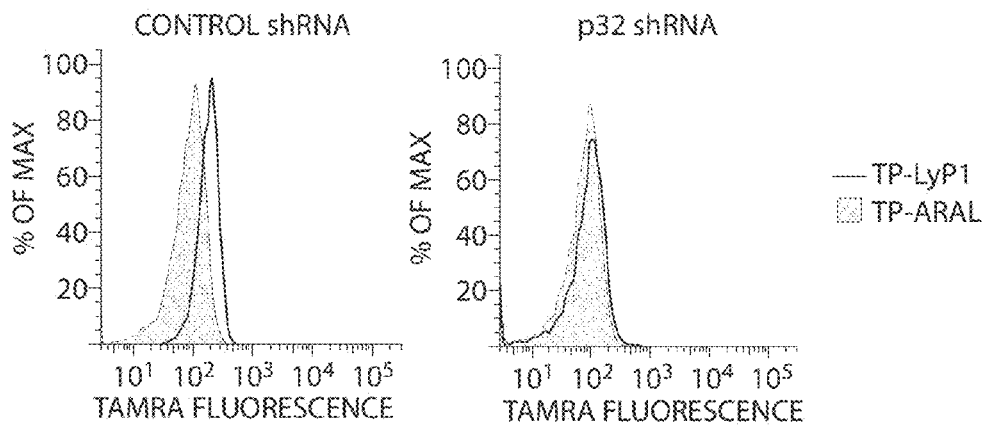
Figure 10A:
Figure 10B:
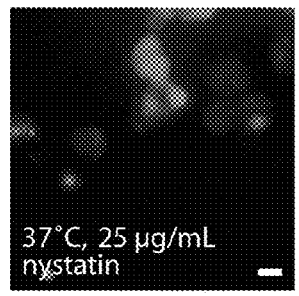
Figure 10C:
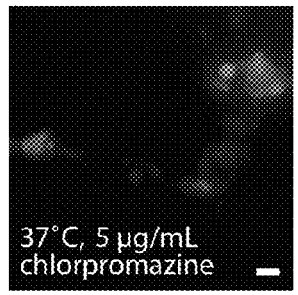
Figure 10D:
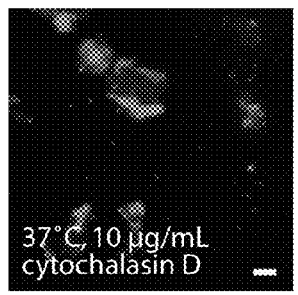
Figure 10E:
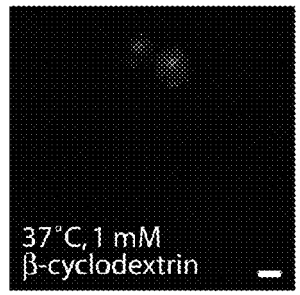
Figure 10F:
Figure 10G:
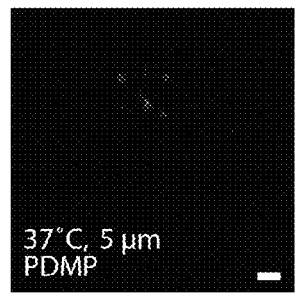
Figure 10H:
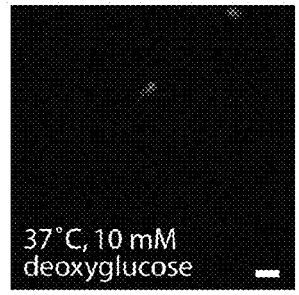
Figure 10I:
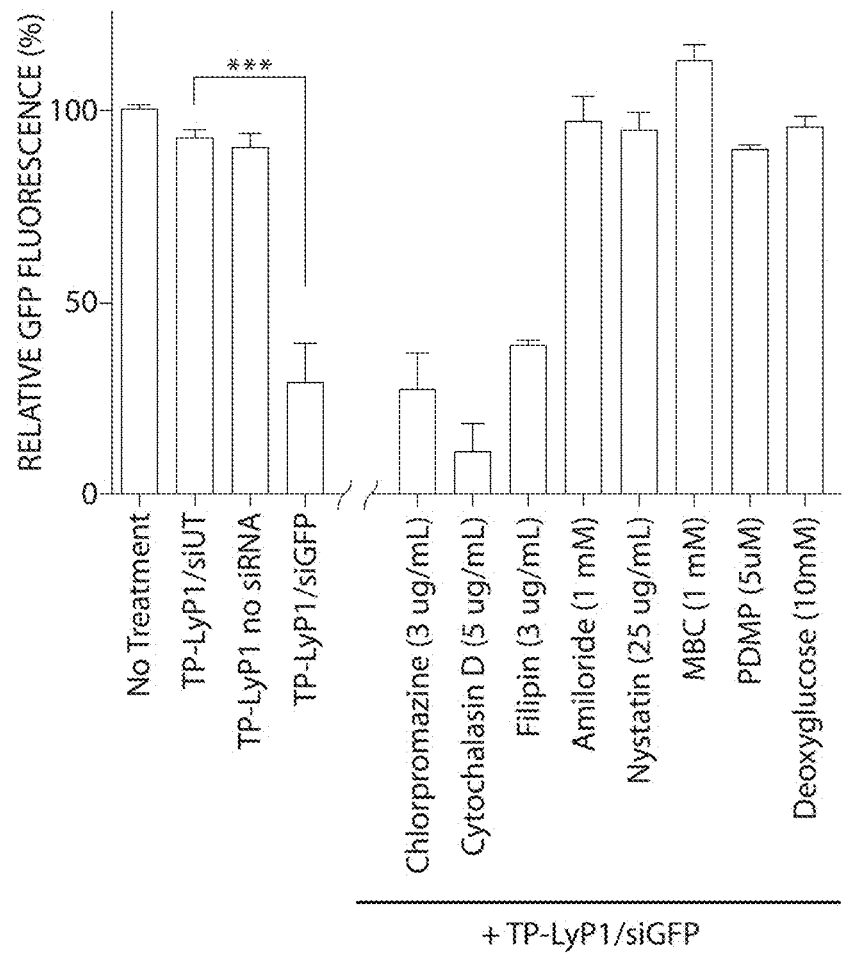
Figure 11B:
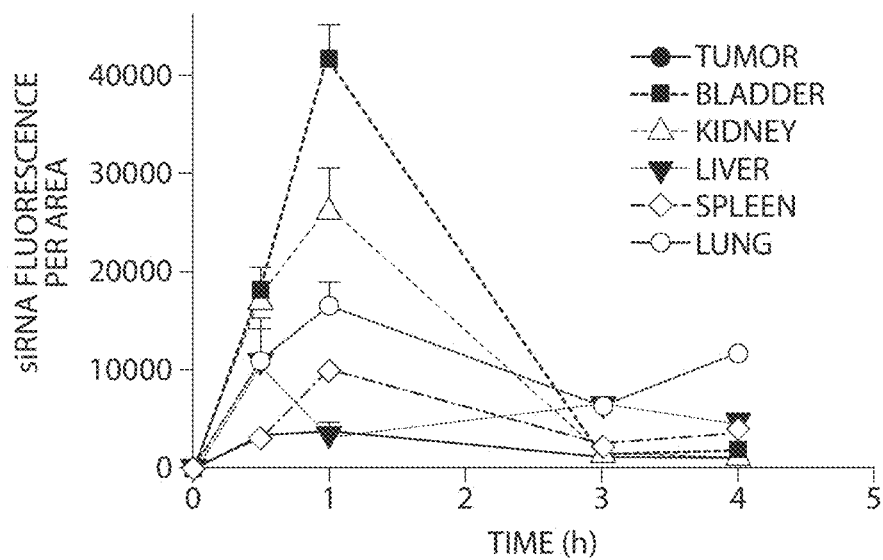
Figure 11C:
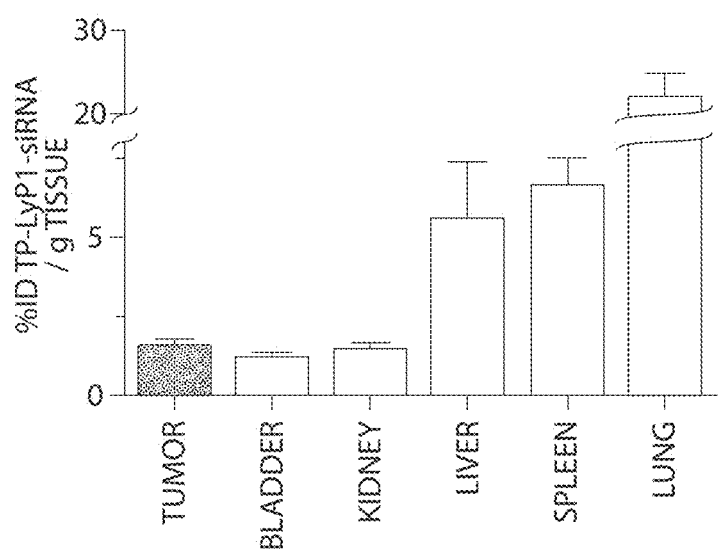
Figure 11D:
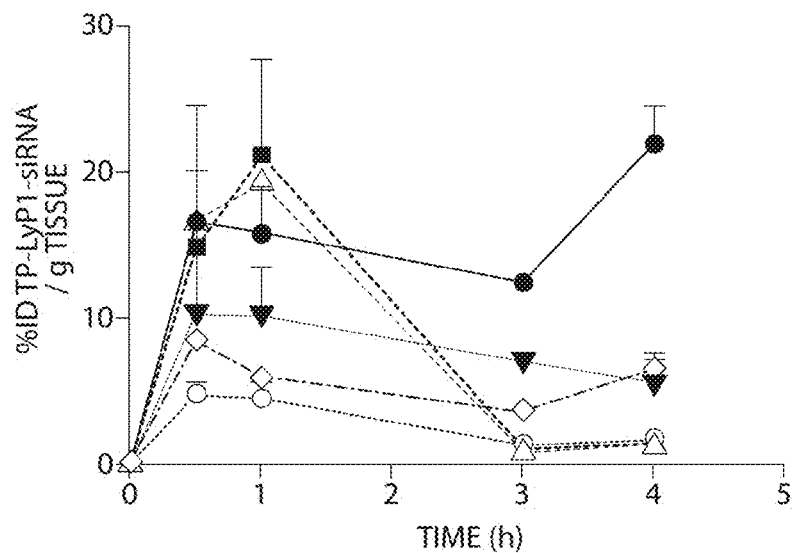
Figure 11E:
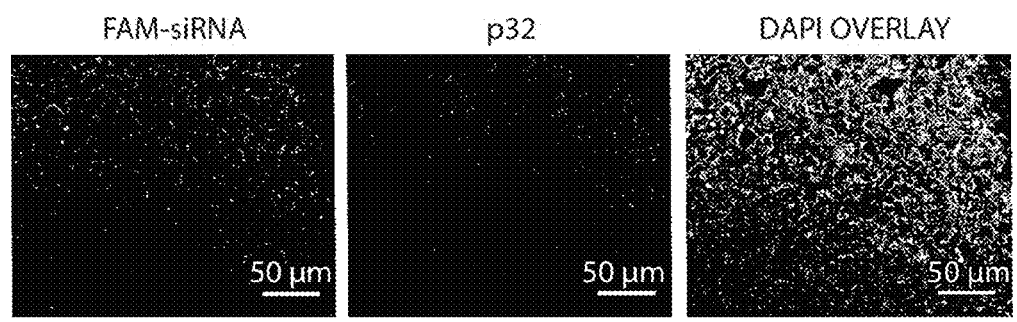
Figure 12A:
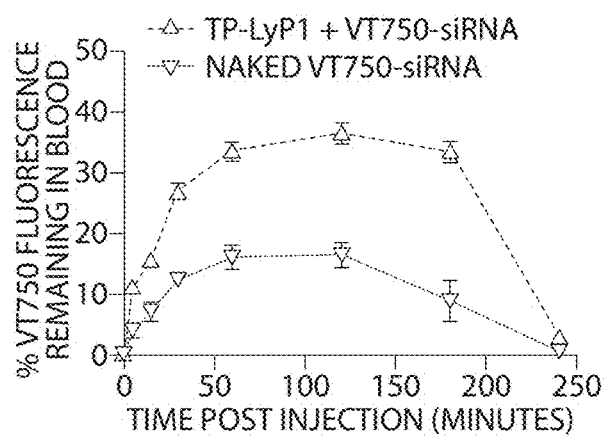
Figure 12B:
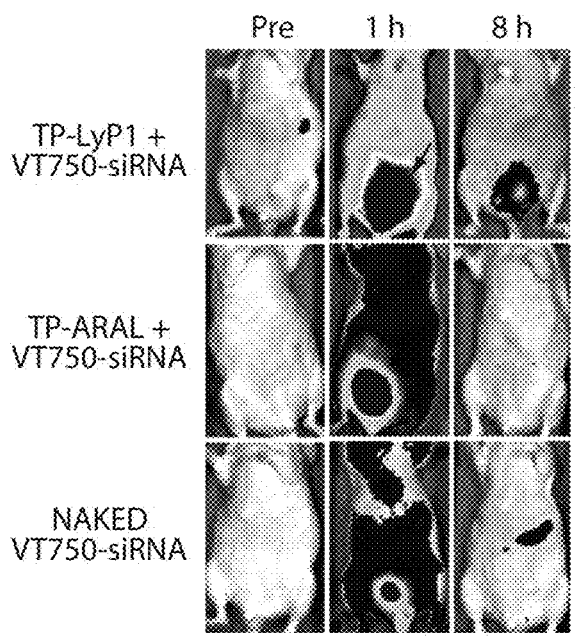
Figure 12C:
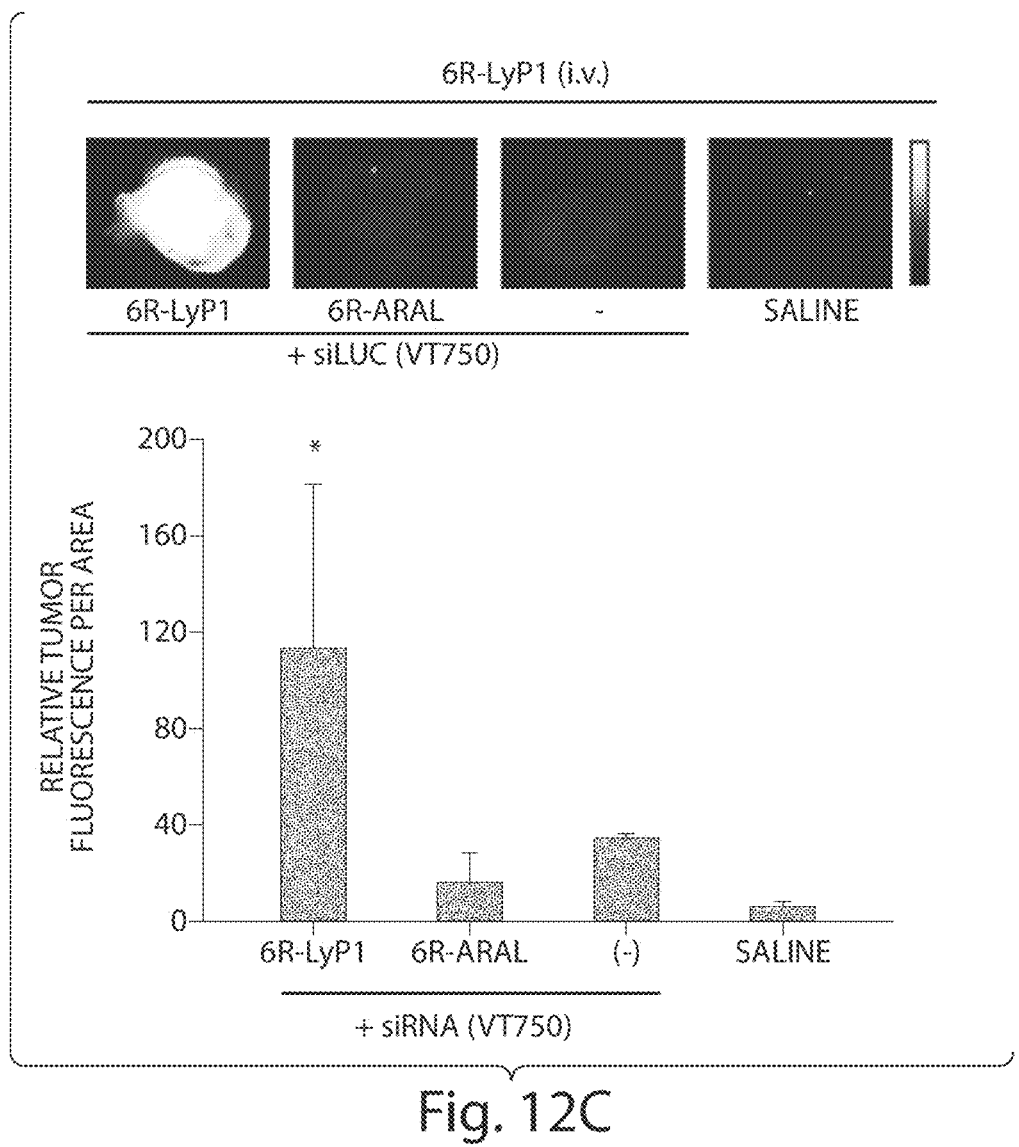
Figure 12D:
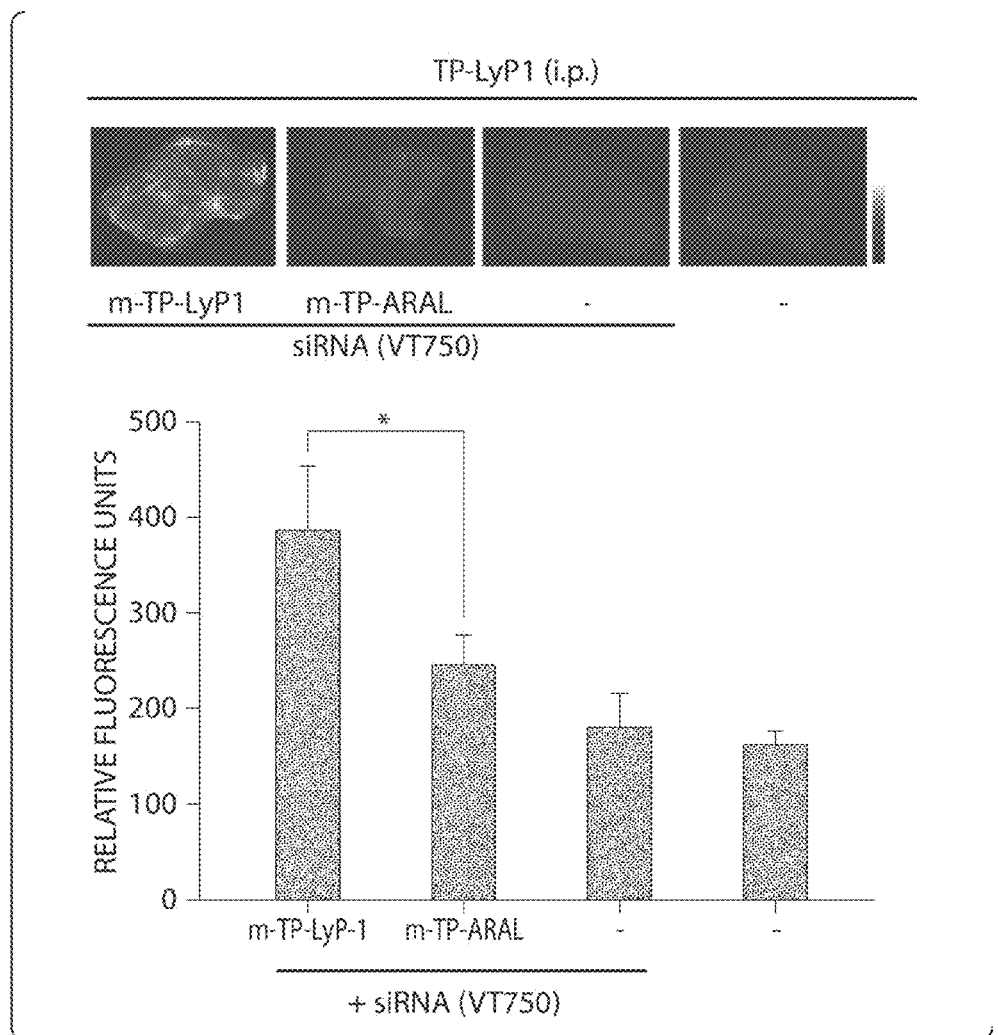
Figure 12E:
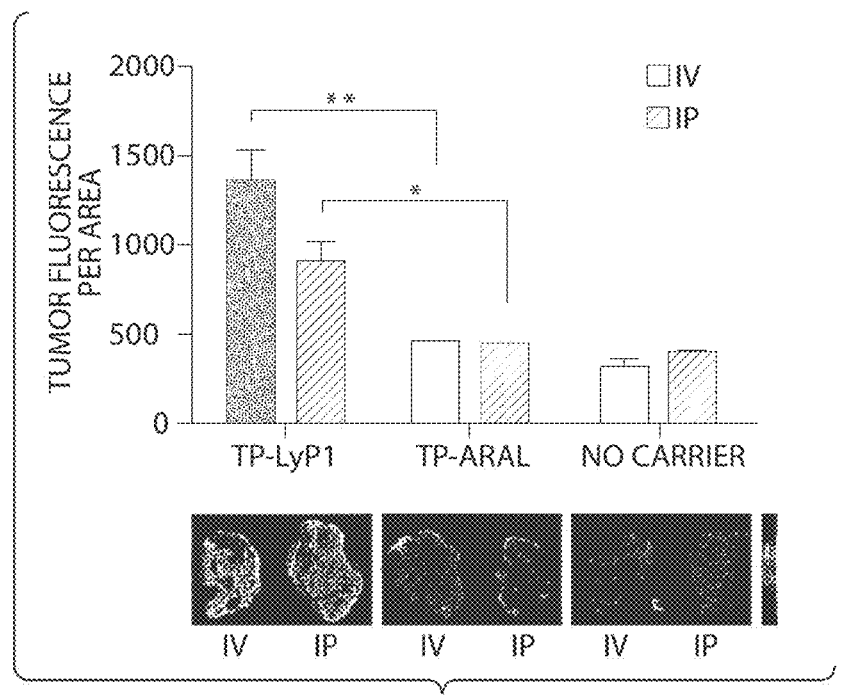
Figure 12F:
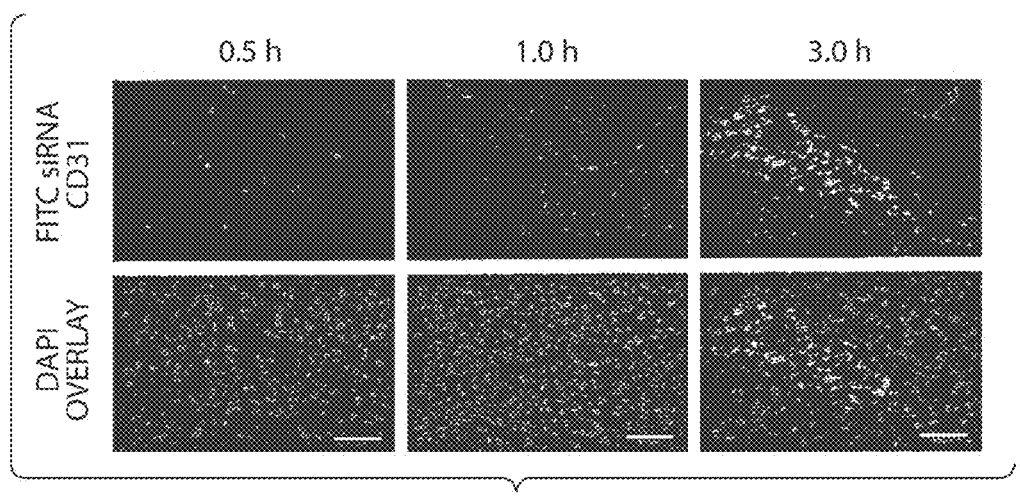
Figure 12G:
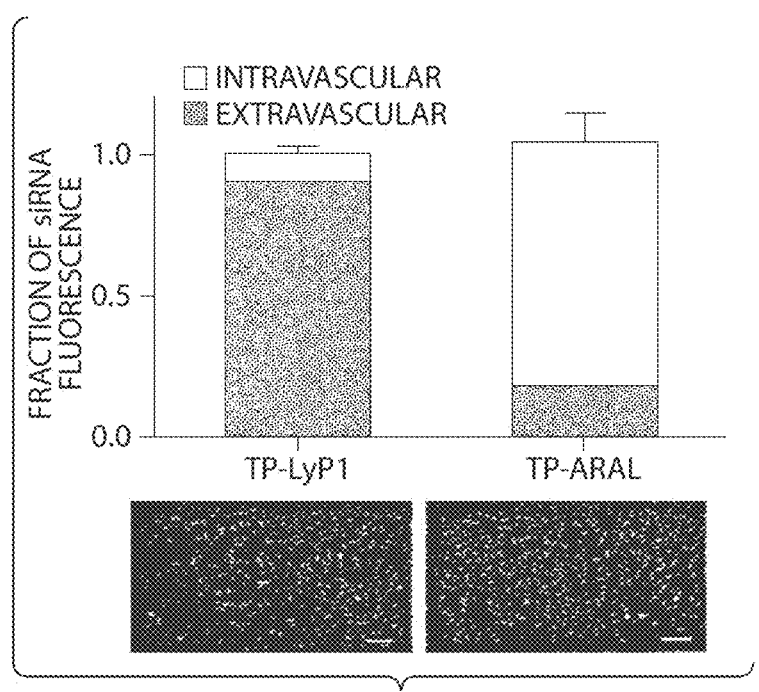
Figure 13A:
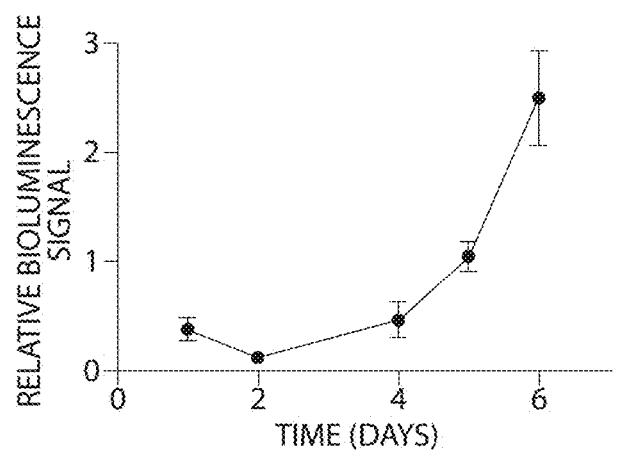
Figure 13B:
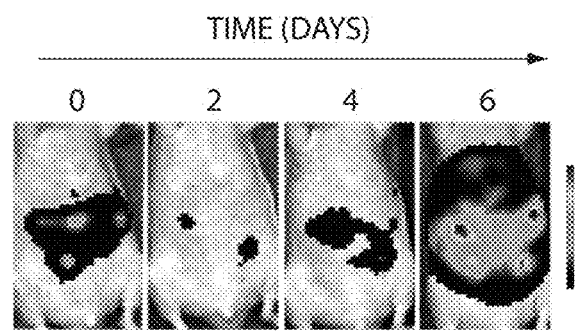
Figure 14:
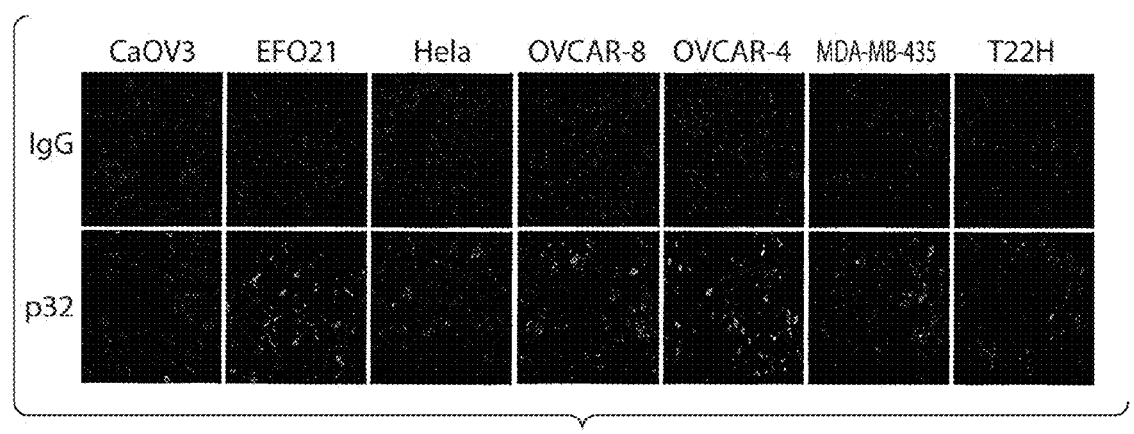
Figure 15A:
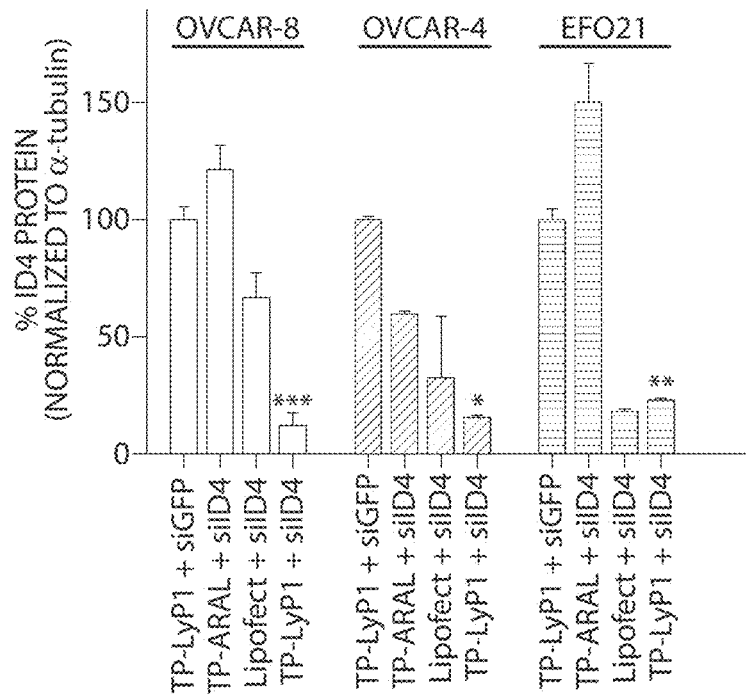
Figure 15B:
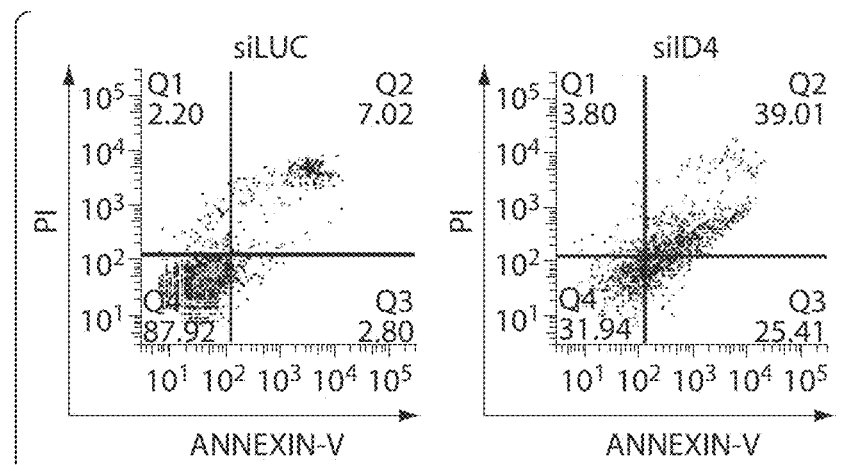
Figure 15C:
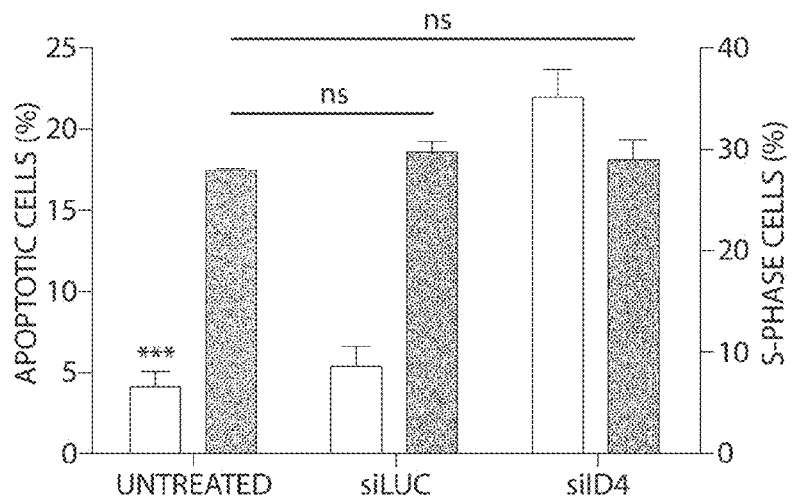
Figure 15D:
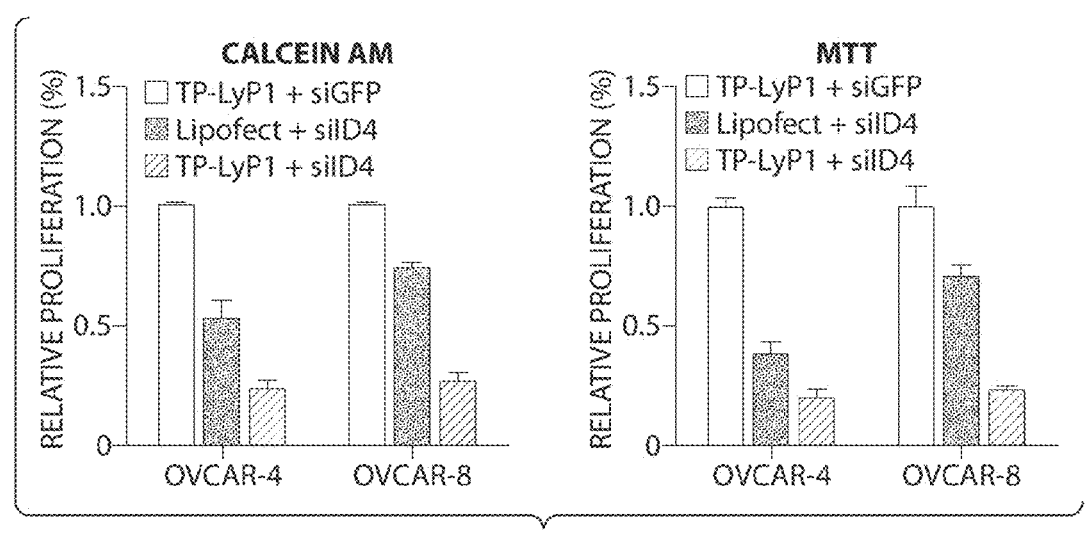
Figure 15E:
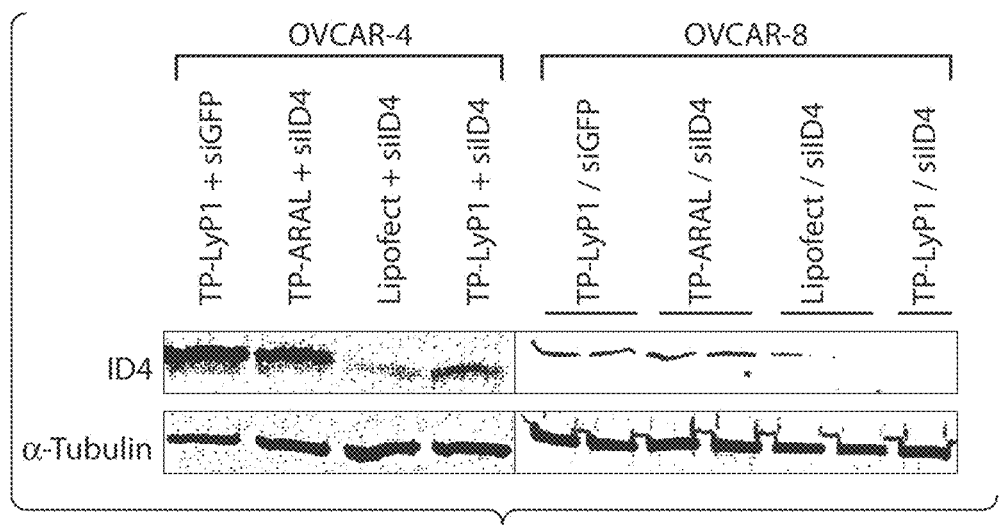
Figure 15F:
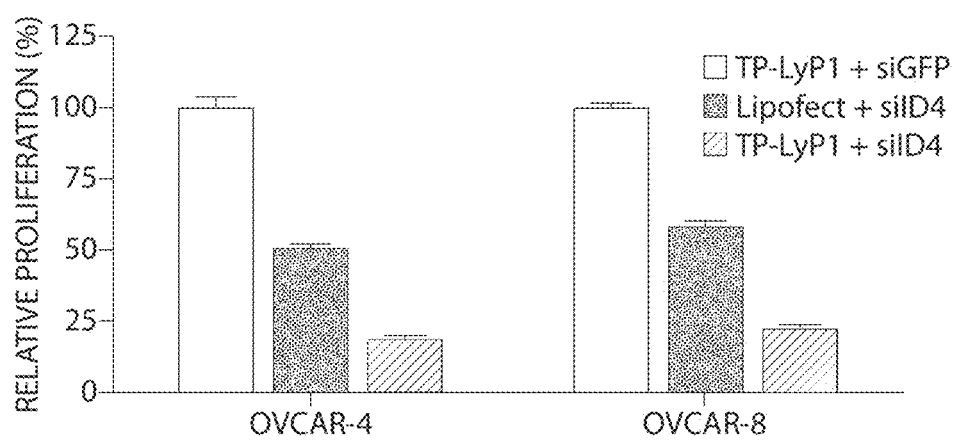
Figure 16A:
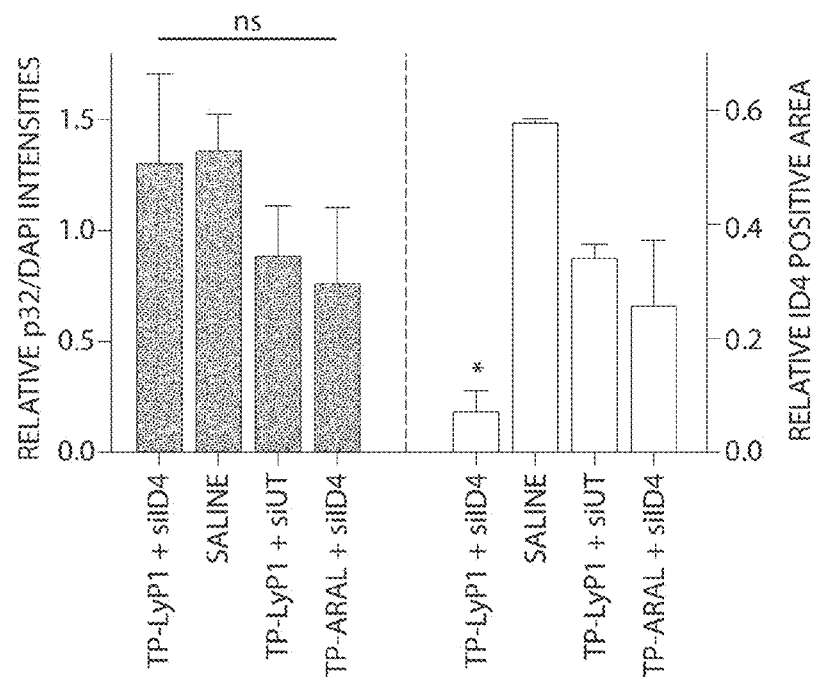
Figure 16B:
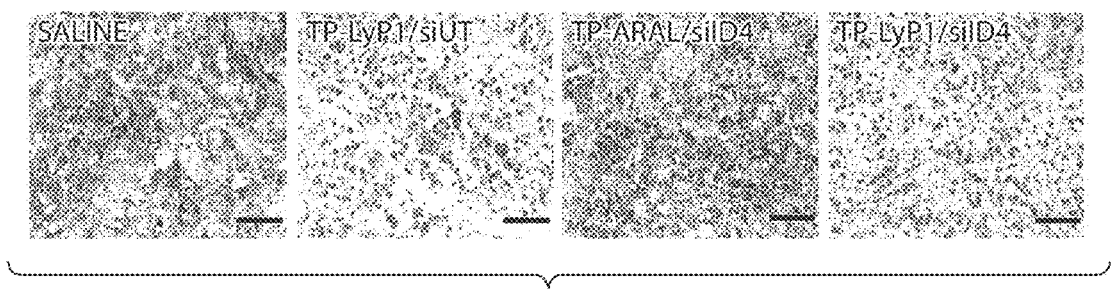
Figure 17A:
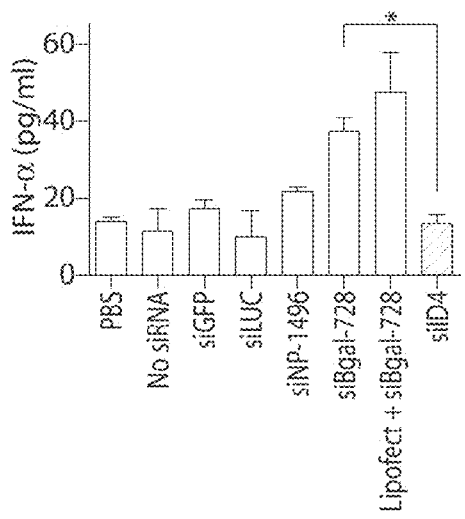
Figure 17B:
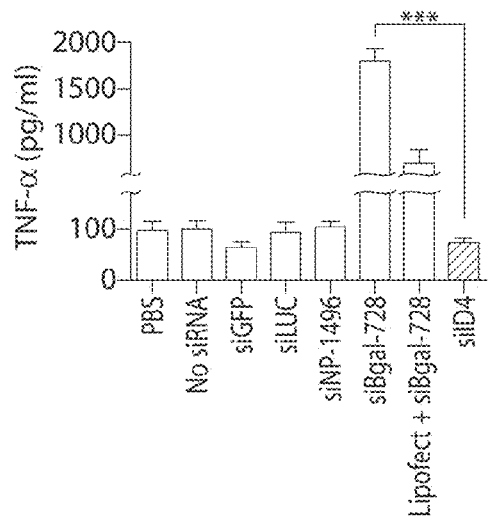
Figure 17C:
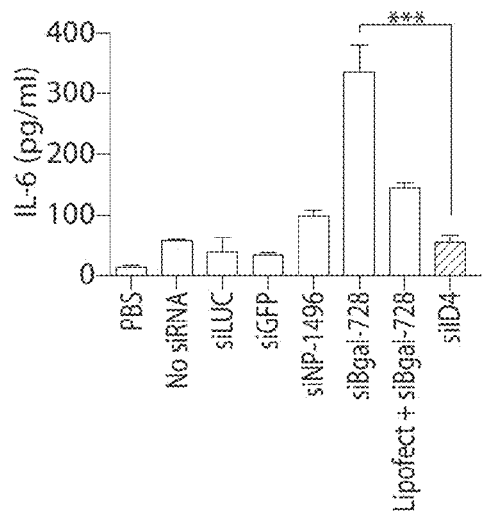
Figure 18A:
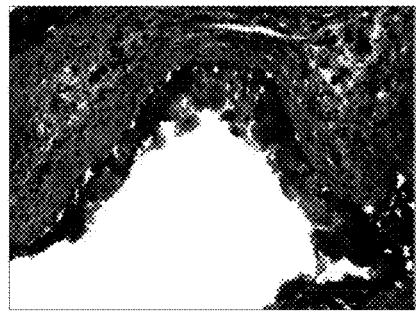
Figure 18B:
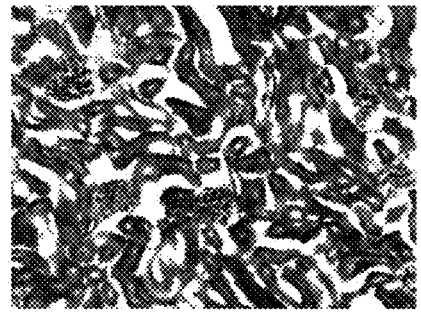
Figure 18C:
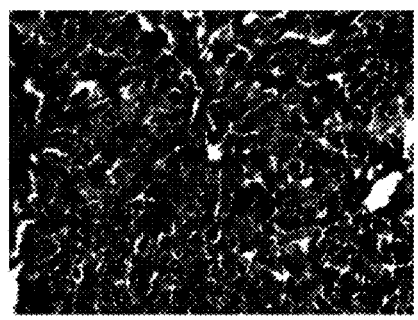
Figure 18D:
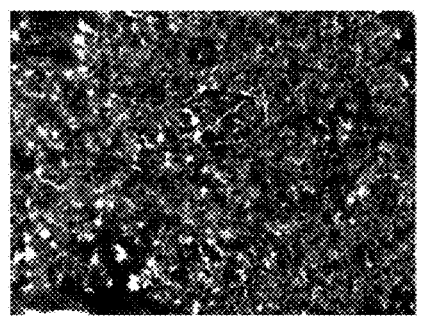
Figure 18E:
Figure 18F:
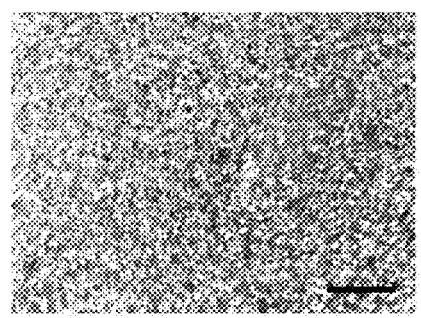
Figure 18G:
Figure 18H:
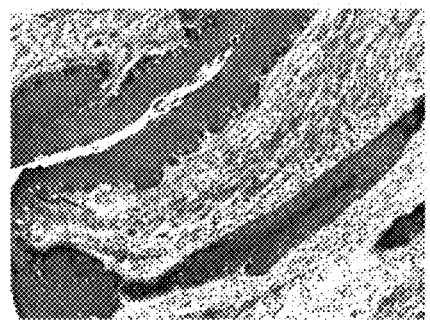
Figure 18I:
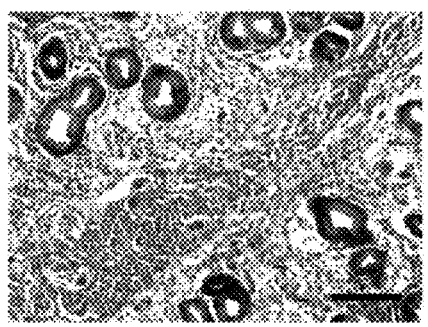

FIG. 5H shows overall survival of all cohorts from a. n=5 for each group. RNAi treatment period is shaded in gray;

FIG. 5I shows that injections of TP-LyP1 nanocomplexes carrying ID4 siRNA into the tail vein inhibited subcutaneous OVCAR-4 tumor growth. At the end of 30 d, tumors were harvested from each cohort and weighed (n=5-10 tumors per each cohort);

FIG. 5J shows the overall body weight of OVCAR-4 tumor-bearing mice over the course of siRNA treatment. Treatment did not negatively affect animal weight in any of the cohorts;

FIG. 5K is a timeline of the OVCAR-8 tumor therapy experiment. Female NCr/nude mice were engrafted orthotopically with OVCAR-8 ovarian carcinoma cells expressing firefly luciferase. After tumor establishment and confirmation of metastatic spread (21 d), TP-LyP1/siID4 nanocomplexes were administered intraperitoneally every 3 d for 2 weeks, then tapered to every 7 d for 3 weeks (5 mg/kg siRNA/injection);

FIG. 6A is a hypothetical cartoon of a candidate tandem peptide. The cyclic homing domain is separated from the cell penetrating domain by a linker (gray);

FIG. 6B shows dynamic light scattering to probe the hydrodynamic size of each nanocomplex in buffered saline over time. Error bars indicate s.d. from 5 separate formulations;

FIG. 6C shows the stability of nanocomplexes in various buffer conditions as indicated by the amount of un-encapsulated, free siRNA measured by the Ribo-Green assay;

FIG. 7 shows cytotoxicity assesssments of tandem peptide/siRNA nanocomplexes obtained using HeLa cells cultured in 96 well plates at ~80% confluency. Cells were treated with various concentrations of either TP-LyP1 (first black bar), TP-ARAL (first gray bar), 6R-LyP1 (second black bar), and 6R-ARAL (Second gray bar) peptides complexed to siRNA for 24 h. Cell viability was measured using Calcein-AM. Error bars indicate s.d. from 4 replicates for each condition. Total viability was normalized to untreated cells;

FIG. 8A demonstrates immunofluorescence staining showing that MDA-MB-435 and HeLa cell lines both express p32 on the cell surface. Rabbit IgG or a polyclonal antibody against full-length p32 was applied to live cells and detected with an Alexa 488-labeled secondary antibody;

FIG. 8B is a flow cytometry analysis of cellular uptake of either TP-LyP1 or TP-ARAL peptide labeled with a TAMRA fluorophore over time;

FIG. 9A is a western blot on whole-cell lysates from MDA-MB-435 tumor cells stably expressing shRNA for p32 or a base mismatch control shRNA (top). Flow cytometry analysis of the same cell lines for surface levels of p32 using polyclonal anti-full-length/$NH_2$-terminal p32 or IgG isotype control (bottom);

FIG. 9B shows that TAMRA-labeled tandem peptides bearing the LyP-1 homing domain or a control domain (ARALPSQRSR, (SEQ ID NO: 1) ARAL) were incubated over p32 shRNA cells; TP-LyP1 binding was only observed in the control cells but not in p32 knockdown cells. TP-ARAL did not bind to either cell line;

FIGS. 10A-B show tandem peptide internalization in the presence of inhibitors that block caveolae-mediated endocytosis (filipin and nystatin);

FIG. 10C shows clathrin-dependent endocytosis (chlorpromazine);

FIG. 10D shows actin polymerization (cytochalasin D);

FIGS. 10E-F shows macropinocytosis (β-cyclodextrin and amiloride);

FIG. 10G shows lipid-raft mediated endocytosis (PDMP);

FIG. 10H shows synthesis of new ATP (deoxyglucose);

FIG. 10I shows nanocomplex internalization in the presence of the same panel of inhibitors as above—error bars indicate s.d; *** $p<0.001$;

In FIG. 11A1 athymic (nu/nu) mice were injected i.p. with naked near-infrared fluorophore (Vivotag 750) labeled siRNA and siRNA complexed to either TP-LyP1 or TP-ARAL; In FIG. 11A2 tumor-bearing mice were injected via the tail vein with near-infrared fluorophore (Vivotag-750) labeled siRNA complexed to TP-LyP1. At various time points, organs and tumors were harvested and imaged on the Li-COR Odyssey scanner;

FIG. 11B shows the quantitation of total fluorescence for explanted organs and tumors over time;

FIG. 11C shows the quantification of total % injected dose accumulated per gram of tissue. Numerical values were computed based on a standard curve using uninjected organs spiked with known amounts of fluorescent siRNA;

FIG. 11D shows the % ID/g for explanted organs at various time points;

In FIG. 11E, after the nanocomplexes were cleared (6 h), tumors were harvested and histological sections showed co-localization of p32-expressing OVCAR-8 tumor cells with injected siRNA. Scale bar, 50 μm;

FIG. 12A shows circulation time of intraperitoneally injected, fluorescently-labeled siRNA (5 nmols) either in its naked form or complexed to a targeted tandem peptide. Error bars indicate s.d. (n=3)—arrows indicate bladder accumulation;

FIG. 12B shows in vivo whole-animal fluorescence imaging at multiple time points after intraperitoneal injection in mice;

FIG. 12C shows homing of 6R-LyP1 nanocomplexes injected intravenously into mice bearing subcutaneous tumor xenografts. After clearance from circulation (6 h after injection), tumors were explanted and fluorescently imaged. Error bars indicate s.d. (n=3);

FIG. 12D shows homing of TP-LyP1 nanocomplexes injected intraperitoneally into mice bearing subcutaneous tumor xenografts. After clearance from circulation (6 h after injection), tumors were explanted and fluorescently imaged. Error bars indicate s.d. (n=3);

FIG. 12E shows the quantification of siRNA fluorescence (top) and representative images of tumor explants harvested after injection of TPNs, untargeted nanocomplexes, or naked siRNA either intravenously or intraperitoneally. Error bars indicate s.d. (n=3);

FIG. 12F is a histological analysis of the time-dependent homing of nanocomplex/FAM-labeled siRNA in relation to blood vessels (CD31) in OVCAR-8 tumors. Representative images from 4 independently analyzed tumors at each time point are shown. Scale bar is 50 μm;

FIG. 12G is a quantification of the extravascular and intravascular fractions of TP-LyP1 versus TP-ARAL nanocomplexes carrying FAM-siRNA. Representative histological sections from 6 independent tumors are shown. Scale bar is 50 μm;

In FIG. 13 mice were injected intraperitoneally with tandem peptide/siRNA nanocomplexes, and the duration of gene silencing was determined by whole-animal bioluminescence imaging of luciferase expression on the indicated days;

FIG. 14 shows six (6) different human cancer cell lines derived from: ovarian cancer (CaOV3, EFO21, OVCAR-8, and OVCAR-4), cervical cancer (HeLa), breast cancer (MDA-MB-435), and a mouse ovarian cancer cell line (T22H) surveyed for surface expression of p32 by immunostaining using a polyclonal p32 antibody;

FIG. 15A is a Western blot analysis of p32-targeted knockdown of ID4 in 3 ovarian cancer cell lines: OVCAR-8, OVCAR-4, and EFO-21. ID4 band intensities are normalized to a-tubulin; 100% ID4 protein is defined as the protein level in cells treated with negative control siRNA;

FIG. 15B ID4 shows that knockdown by nanocomplexes induced apoptosis as shown in the representative example of Annexin-V staining by flow cytometry (left panel), siRNA against luciferase did not induce apoptosis (right panel);

FIG. 15C is a summary of Annexin-V assays (white bars) and cells entering S-phase by the Click-iT-EDU assay (black bars). The percentages of apoptotic and s-phase cells were calculated. Three independent experiments were pooled and analyzed as a combined data set. Error bars indicate s.d.; n.s., not significant; *p<0.05; p<0.01; *p<0.001;

FIG. 15D shows Calcein-AM and MTT cytotoxicity assays of OVCAR-4 and OVCAR-8 cells after transfection with siID4. Lipofectamine was used as a positive control transfection reagent;

FIG. 15E is an Immunoblot of ID4 in 6p22-amplified cell lines treated with nanocomplexes. Lipofectamine was used as a positive control. Untargeted peptide or irrelevant siRNA were used as negative controls;

FIG. 15F shows the proliferation of ovarian cancer cell lines treated with nanocomplex containing ID4 siRNA compared to TP-LyP1/GFP siRNA (white bars), TP-ARAL/ID4 siRNA (gray bars) or lipofectamine bound ID4 siRNA (black bars). Error bars indicate s.d. for 4 separate experiments;

FIG. 16A shows that treatment with p32-targeted nanocomplexes resulted in a slight increase in p32 levels (Left, black bars), and significant suppression of ID4 expression (Right, white bars). Tumor sections from a representative mouse in each cohort were stained for p32 and ID4 via immunohistochemistry. The values represent means from p32 fluorescence intensities normalized to DAPI from 5 separate sections (left) and averaged area percentage positive for ID4 (right). Statistical analyses were performed using ANOVA; Error bars, mean±SEM; n.s., not significant; * p<0.05;

FIG. 16B is an immunohistochemical staining for ID4 in sections harvested from OVCAR-8 tumor-bearing mice. Scale bar, 50 µm;

In FIGS. 17A-C immunocompetent Balb/c mice were injected intraperitoneally with nanocomplexes comprising the TP-LyP1 tandem peptide and siRNA against ID4, and 6 h later serum samples were tested for levels of interferon-alpha (IFN-α, a), TNF-α (b), and IL-6 (c) by ELISA (the immunostimulatory siRNA sequence, siBgal-728, was complexed to either lipofectamine or TP-LyP1 and were used as positive controls. n=4-6 per group. Error bars, mean±SEM; *p<0.05; ***p<0.001); and In FIGS. 18A-I mice bearing orthotopic OVCAR-8 tumors were treated bi-weekly for 14 days and then weekly for 26 days with TP-LyP1/siID4 nanocomplexes (5 mg/kg of body weight). The following organs were harvested and stained with H&E: bladder (a), kidney (b), liver (c), spleen (d), heart (e), brain (f), ovary (g), cervix (h), and uterus (i). No relevant histological or morphological evidence of toxicity in these organs were observed. Scale bar is 100 µm.

DETAILED DESCRIPTION OF INVENTION

Aspects of the invention relate to compositions and methods for delivering nucleic acids to target cells of interest. In some embodiments, aspects of the invention relate to a polypeptide that includes a cellular targeting domain and a nucleic acid binding domain. In some embodiments, the cellular targeting domain provides a cell-specific targeting function, and the nucleic acid binding domain provides a non-cell-specific protein transduction function (e.g., to cross cellular membranes non-specifically) in addition to a nucleic acid binding function. In some embodiments, the cellular targeting domain also provides a tissue penetrating function. In some embodiments, the protein transduction domain is selected so that the cell-specific targeting properties of the targeting domain dominate relative to the non-cell-specific properties of the protein transduction domain. This favors or promotes cell-specific delivery relative to non-cell-specific delivery. In some embodiments, the charge of the protein transduction domain is selected to be below a first threshold level of positive charges to reduce the strength of the non-cell-specific protein transduction properties relative to the cell-specific targeting properties of the targeting domain. However, in some embodiments, the charge of the protein transduction domain is above a second threshold level of positive charges to provide sufficient binding affinity and/or protection for the nucleic acid of interest.

In some embodiments, cell-specific targeting relative to non-cell-specific delivery can be evaluated by determining the extent to which a free targeting peptide (e.g., a free Lyp1, iRGD, or other targeting peptide) competes with a nucleic acid/protein complex containing the same targeting peptide for delivery to a cell of interest. If the free peptide competes effectively, then the complex delivery is cell-specific (it involve the cell-specific targeting peptide). If the free peptide does not compete, then delivery is non-cell-specific. In some embodiments, competition can be evaluated in a specific cell-based assay to determine whether the amount of delivery (e.g., of the peptide, nucleic acid, or both) is reduced by incubating the complex along with free peptide. The amount of delivery can be assayed by determining the amount of label that is delivered (e.g., if the peptide and/or nucleic acid is labeled, for example with a fluorescent tag), or the level of nucleic acid function (e.g., based on expression knockdown of a target gene). In some embodiments, an assay involves incubating a complex with a 10 fold molar excess of free targeting peptide relative to complexed peptide. According to aspects of the invention, a 50%-100% decrease in the amount of complex delivered to the cell (in the to presence of a 10-fold excess of free peptide) corresponds to specific targeting of that cell type. In some embodiments, specific targeting is associated with a decrease of 60% or more, 70% or more, 80% or more, 90% or more, 80%-90%, 90%-95%, or 95%-100%.

In some embodiments, the polypeptide is complexed with a nucleic acid to form a composition (e.g., a multivalent composition) for delivering the nucleic acid to a target cell. In some embodiments, the charge ratio of the nucleic acid relative to the protein transduction domain is selected to reduce non-specific protein transduction.

Accordingly, in some embodiments a polypeptide includes a cellular targeting domain having a motif that binds a molecule on a target cell, and a nucleic acid binding domain having a motif that binds to a nucleic acid of interest for delivery to the target cell. In some embodiments, delivery may be targeted to specific cells by using a cellular targeting motif that binds to specific cells (e.g., diseased cells, cell of a specific tissue, etc.). In some embodiments, a polypeptide may include a cell-penetrating motif (e.g., a non-specific cell-penetrating motif) in addition to the targeting motif in order to promote transduction across the membrane of the target cell. In some embodiments, the cell-penetrating motif may be separate from either the targeting motif and/or the nucleic acid binding motif. However, in some embodiments, a non-specific cell-penetrating motif (also referred to as a protein transduction motif) may overlap with the nucleic acid binding motif.

In some embodiments, compositions include tumor-penetrating nanocomplexes (TPN) composed of tandem tumor-penetration and membrane-translocation peptides that efficiently deliver siRNA into the tumor parenchyma.

FIG. 1 illustrates a non-limiting embodiment of a polypeptide of the invention and its use to deliver a nucleic acid to a cell. FIG. 1A shows a polypeptide having two domains. A first domain (illustrated as a homing domain) that includes a motif that binds to a cell-surface molecule and a second domain (illustrated as a cell penetrating domain) that promotes cell penetration and also binds to nucleic acid (illustrated as siRNA). This protein forms a multivalent complex when mixed with the nucleic acid. FIG. 1B illustrates a non-limiting cellular delivery mechanism of the protein/nucleic acid complex of FIG. 1A.

In some embodiments, a tandem peptide that is useful for effectively targeting nucleic acids to a particular cell type includes a cell-type-specific targeting domain that is joined to a nucleic acid binding domain, wherein the nucleic acid binding domain also to has cellular penetrating properties. Surprisingly, it was found that effective cell-specific targeting and delivery of nucleic acids can be achieved using the cellular penetrating properties of a non-cell-specific protein transduction domain (PTD) that is fused to a targeting domain (e.g., a tumor penetrating targeting domain, for example, a cyclic peptide homing domain). It was surprising that the non-cell-specific cellular penetrating properties of a PTD can be masked relative to the specific targeting properties of a targeting domain (e.g., a tumor penetrating targeting domain, for example, a cyclic peptide homing domain) in the context of a complex with a nucleic acid (e.g., an siRNA molecule).

In some embodiments, the targeting domain itself can provide sufficient cell penetrating properties to allow for efficient initial cellular penetration even if the PTD domain is masked. In some embodiments, the PTD domain helps the complex penetrate the membrane of the target cell. In some embodiments, the PTD domain is useful to release nucleic acid into the cytoplasm from the endosome after the initial cell penetration. Accordingly, the binding of the nucleic acid to the PTD should not be so tight as to prevent efficient release within the cell (e.g., within the endosome).

In some embodiments, the non-cell-specific penetrating properties of a PTD can be reduced by reducing the number of positively charged (e.g., basic) amino acids in the PTD and/or by masking the positively charged amino acids of the PTD with the negative charges of the nucleic acid (siRNA) that is being delivered.

In some embodiments, a PTD having between 4 and 8 (e.g., 5-7, or about 6) positively basic amino acids (e.g., Arg, Lys, and/or His) is used. In some embodiments, a PTD having a basic amino acid content of less than 50%, less than 40%, less than 30%, less than 25%, less than 20%, or less than 15% is used. According to aspects of the invention, a higher number of positive charges (e.g., basic amino acids) on a PTD can promote non-cell specific delivery and/or tight PTD/nucleic acid binding that does not allow for efficient release of the nucleic acid within the cell.

In some embodiments, a molar ratio of siRNA molecules to PTD domains of between about 1:20 to about 1:30 is used for forming complexes that provide functional delivery of nucleic acid. In some embodiments, a ratio of lower than about 1:20 results in not all siRNA nucleic acids being encapsulated. Without wishing to be bound by theory, it is thought that having excess peptide can lead to over-complexation of an siRNA nucleic acid and that this leads to less efficient cytosolic release of the nucleic to acid. However, it should be appreciated that ratios of between 1:15 and 1:35 or slightly higher or lower ratios may be used in some circumstances where lower delivery efficiency is nonetheless useful.

Similar factors should be considered for other nucleic acids. In some embodiments, the charge ratio may be a more useful consideration. A siRNA nucleic acid typically is a duplex of about 21 nucleotides, thus having a net 42 negative charges (phosphate backbone in a duplex). In some embodiments, depending on the PTD that is used, the ratio of net positive-to-negative charges (positive amino acid residues per tandem peptide times the number of tandem peptides divided by the product of the number of negative charges per siRNA molecule by the number of siRNA molecules) is between about 2:1 to about 3:1. This ratio provides for efficient nucleic acid release into the cytosol of a targeted cell while not producing high levels of non-cell-specific delivery. It should be appreciated that slightly higher or lower ratios may be used. However, according to some aspects of the invention, a ratio that is significantly higher than 3:1 (for example 3.5:1; 4:1, or higher) can result in a loss of specificity and increased non-cell-specific delivery due to increased general protein transduction strength. In some embodiments, without wishing to be bound by theory, even higher ratios (for example about 6:1 or higher) can cause tight binding between the nucleic acid and peptide resulting in reduced release into the cytosol.

It should also be appreciated that for any given charge-ratio, the molar ratio will vary depending on the length and the number of charges on the nucleic acid.

In some embodiments, certain structural features, for example the formation of a helical secondary structure can be important for efficient delivery. An example of the helical structure of a peptide related to TP, can be found at: http://www.ncbi.nlm.nih.gov/pmc/articles/PMC1864827/figure/fig1/.

In some embodiments, a peptide/nucleic acid complex having a binding avidity 10× higher than that of free peptide to cells expressing a target antigen (e.g., the p32 receptor) promotes efficient nucleic acid delivery. In some embodiments, a Kd of about 5-25 nM (e.g., about 18 nM) of nano-complex versus about 50-250 nM (e.g., about 180 nM) of free peptide is useful.

Accordingly, aspects of the invention provide for a modular nucleic acid delivery platform that includes a targeting component, a nucleic acid binding component, and to optionally a cell penetrating component. In some embodiments, aspects of the invention relate to the design of polypeptides having particular targeting and/or delivery profiles. It should be appreciated that several factors may be considered when designing a polypeptide for nucleic acid delivery, including, but not limited to, the cellular target, the nucleic acid being delivered, the delivery kinetics, and other factors. In some embodiments, the nucleic acid binding properties are selected so that they are sufficiently strong to promote the formation of a stable complex for delivery, but not too strong to prevent release of the nucleic acid at the site of delivery (e.g., once the complex is internalized in a target cell). In some embodiments, a cell penetration motif is selected with cell penetrating properties that are sufficient to promote cell penetration at the target cell of interest, but that do not promote non-specific cell penetration. It should be appreciated that this may be accomplished by selecting a motif with an appropriate level of cell penetration so that it does not dominate the specific targeting properties of the targeting domain. In some embodiments, the selection of a linker or other surrounding sequences also may be used to mask some of the cell penetrating properties of a cell penetration motif in order to retain sufficient activity for assisting in cell penetration without rendering the complex non-cell specific. In some embodiments, the linker peptide is non-charged, more preferably non-polar. Preferably, a linker is made up of a majority of amino acids that are sterically unhindered, such as glycine and alanine. Thus, preferred linkers include polyglycines, poly(Gly-Ala)s, and polyalanines. The length of the linker is between 1 and 100 amino acids, or between 1 and about 25 amino acids, or between 1 and about 15 amino acids, for example 2, 3, 4, 5, 6, 7, 8, 9, 10, 11, or 12 amino acids long. In some embodiments, the linker has no basic amino acids and/or charged amino acids. It should be appreciated that in some embodiments a synthetic (e.g., a non-peptide, for example a non-peptide carbon based linker) may be used.

In some embodiments, aspects of the invention may be useful for delivering one or more nucleic acids for therapeutic applications. For example, a therapeutic nucleic acid may be a regulatory nucleic acid (e.g., a regulatory RNA, DNA, or synthetic nucleic acid), a nucleic acid that encodes a therapeutic molecule (e.g., that encodes a therapeutic RNA, and/or a therapeutic peptide), or other nucleic acid that has therapeutic applications. Accordingly, in some embodiments, aspects of the invention relate to compositions and methods for treating subjects having a disease or disorder.

In some embodiments, aspects of the invention may be useful to deliver nucleic acid for diagnostic and/or research applications. However, it should be appreciated that compositions and methods of the invention may be used to deliver any nucleic acid of interest to a target cell as aspects of the invention are not limited by the type of application.

In some embodiments, aspects of the invention relate to compositions and methods for assembling a protein nucleic acid complex suitable for delivering the nucleic acid to a target cell.

According to aspects of the invention, RNA interference offers an attractive means to silence gene expression with extraordinary specificity, particularly for the subset of "undruggable" gene targets [Elbashir, S. M. et al. Duplexes of 21-nucleotide RNAs mediate RNA interference in cultured mammalian cells. *Nature* 411, 494-498, (2001); Fire, A. et al. Potent and specific genetic interference by double-stranded RNA in *Caenorhabditis elegans. Nature* 391, 806-811, (1998); and Hopkins, A. L. & Groom, C. R. The druggable genome. *Nat Rev Drug Discov* 1, 727-730, (2002)]. To date, approaches to target the delivery of siRNA in vivo have focused on chemical modifications [Soutschek, J. et al. Therapeutic silencing of an endogenous gene by systemic administration of modified siRNAs. *Nature* 432, 173-178, (2004); Wolfrum, C. et al. Mechanisms and optimization of in vivo delivery of lipophilic siRNAs. *Nat Biotechnol* 25, 1149-1157, (2007)] and carrier development [Akinc, A. et al. A combinatorial library of lipid-like materials for delivery of RNAi therapeutics. *Nat Biotechnol* 26, 561-569, (2008); Davis, M. E. et al. Evidence of RNAi in humans from systemically administered siRNA via targeted nanoparticles. *Nature*, (2010); Eguchi, A. et al. Efficient siRNA delivery into primary cells by a peptide transduction domain-dsRNA dsRNA binding domain fusion protein. *Nat Biotechnol* 27, 567-571, (2009); Kumar, P. et al. T cell-specific siRNA delivery suppresses HIV-1 infection in humanized mice. *Cell* 134, 577-586, (2008); and Kumar, P. et al. Transvascular delivery of small interfering RNA to the central nervous system. *Nature* 448, 39-43, (2007)]. Nevertheless, tumor-targeted RNAi remains challenging. Unlike small molecule or antibody therapeutics, siRNAs must home to specific intracellular compartments such as the cytosol to act. Cell-penetrating peptides (CPPs) such as TAT and poly-Arg emerged as efficient cytosolic delivery vehicles [Kumar, P. et al. Transvascular delivery of small interfering RNA to the central nervous system. Nature 448, 39-43, (2007); and Karnoub, A. E. et al. Mesenchymal stem cells within tumour stroma promote breast cancer metastasis. *Nature* 449, 557-563, (2007)]. Since they often contain positively-charged residues, they can also electrostatically bind siRNA. However, CPPs are ubiquitous internalizers that are non-specific to any cell type. In contrast, aspects of the invention provide modular polypeptides that can be designed and/or adapted to deliver nucleic acids such as siRNA molecules to specific cells of interest by combining specific cellular targeting domains with less specific cell-penetrating domains that also bind to the siRNA.

However, aspects of the invention may be used to deliver any nucleic acid to any cellular target using an appropriate combination of a cellular targeting domain, a nucleic acid binding domain, and/or a cell-penetrating domain. It should be appreciated that the different domains may be configured in any suitable relative order. In some embodiments, the targeting domain may be at the N-terminus of the polypeptide (or N-terminal relative to one or more of the other domains). In some embodiments, the targeting domain may be at the C-terminus of the polypeptide (or C-terminal relative to one or more of the other domains). Similarly the nucleic acid binding and/or cell penetrating domain may be at the N-terminus or C-terminus of the polypeptide. In some embodiments, a polypeptide may include one or more linkers between different domains. The linkers may be selected or designed to optimize the targeting and/or delivery properties of interest. It also should be appreciated that a polypeptide may include one or more additional peptide domains or motifs (e.g., for purification, stabilization, modification, binding to one or more additional receptors, for example for Fc receptor binding, etc., or any combination thereof) as aspects of the invention are not limited in this respect. In some embodiments, the additional domains or motifs may be at N-terminus, C-terminus, and/or within the polypeptide. In some embodiments, the polypeptides of the invention are renally excreted.

In some embodiments, a PTD providing both nucleic acid binding and cellular penetration properties is at the N-terminus of a tandem peptide, and a targeting domain having a circular peptide component (e.g., a circular homing peptide) is at the C-terminus. Without wishing to be bound by theory, the presence of a circular peptide at the C-terminus provides protection from proteases and or nucleases, thereby stabilizing the complex.

In some embodiments, polypeptides of the invention are modified with a lipid (e.g., myristic acid) to further promote efficient cellular transduction and delivery of the nucleic acid to the intracellular space. The lipid modification may be at the N-terminus, C-terminus, and/or other location (e.g., one or more side chains) of the polypeptide. In some embodiments, the protein transduction domain may be lipid-modified (e.g., myristoylated). In some embodiments, lipid modification at the N-terminus of an N-terminal PTD sequence increases the efficiency of cellular delivery, without reducing the cell-specificity provided by a C-terminal targeting domain.

In some embodiments, other lipophilic modifications (e.g., with cholesterol, saturated fatty acids having C12-C18 carbon atoms, or other appropriate moieties) may be made instead of myristoylation (e.g., at the N-terminus, C-terminus, or both).

Cellular Targeting Domain:

A cell-surface binding motif may be designed, selected, and/or isolated from a known molecule capable of reacting with or otherwise recognizing or binding to a cell surface molecule on a target cell of interest. A cell-surface binding motif for use in the invention may include, but is not limited to a natural binding partner (or a binding fragment thereof) of a cell surface molecule (e.g., protein or other cell surface molecule). An example of a cell surface binding motif includes a ligand or an antibody that specifically binds to its corresponding target, for example, a receptor or an epitope on a cell surface. However, it should be appreciated that in some embodiments the cell-surface binding motif may be a synthetic molecule (e.g., a synthetic peptide, nucleic acid, or other synthetic molecule) that binds to a cell surface molecule. It should be appreciated that the cell-surface binding motif may be a naturally occurring motif. In some embodiments, the cell-surface binding motif may be cell or tissue specific (e.g., preferentially or uniquely present on specific cells or tissue). In certain embodiments, a cell surface molecule may be naturally present on two or more cell or tissue types (e.g., not cell or tissue specific). In some embodiments, a cell surface molecule may be specific for a particular condition (e.g., a disease state, for example a variant molecule associated with a disease such as cancer).

Any known cell-surface binding motif or targeting peptide can be used as the first domain of the fusion polypeptide of the invention. Examples of targeting peptides that can be manipulated and cloned or linked to produce a fusion polypeptide are ample in the literature. For example, a targeting peptide may include the sequence of a protein or to peptide that is recognized by a binding partner on the surface of a target cell, which for the sake of convenience is termed a receptor. However, it should be understood that for purposes of the invention, the term "receptor" encompasses signal-transducing receptors (e.g., receptors for hormones, steroids, cytokines, insulin, and other growth factors), recognition molecules (e.g., MHC molecules, B- or T-cell receptors), nutrient uptake receptors (such as transferrin receptor), lectins, ion channels, adhesion molecules, extracellular matrix binding proteins, and the like that are located and accessible at the surface of the target cell.

The size of the cell-surface binding motif can vary within certain parameters. Examples of cell-surface binding motifs include, but are not limited to, antibodies, lymphokines, cytokines, receptor proteins such as CD4 and CD8, hormones, growth factors, and the like which specifically bind desired target cells. For example, several human malignancies over-express specific receptors, including HER2, LHRH and CXCR4. Accordingly, ligands to these receptors can be used in the fusion polypeptides, methods and compositions of the invention. Receptor ligand domains are known in the art.

In some embodiments, the cell-surface binding motif comprises a homing peptide that selectively homes to a target cell of interest (e.g., binds to a cell specific surface antigen). In some embodiments, it promotes extravasation into surrounding tissues. In some embodiments, the homing domain also promotes penetration into the cells (e.g., via endocytosis). In some embodiments, the homing peptide is cyclic or otherwise conformationally constrained. Cyclic peptides (or cyclic proteins) are polypeptide chains whose amino and carboxyl termini are themselves linked together with a peptide bond, forming a circular chain. Cyclic peptides tend to be extremely resistant to digestion, allowing them to survive intact in the human digestive tract. In some embodiments, the cyclic homing peptide is Lyp1 which binds the cell surface receptor p32 that is aberrantly expressed in the lymphatics of many tumors.

In some embodiments, one or more of a class of tumor-penetrating peptides may be used as a targeting domain. Examples of tumor-penetrating peptides include LyP1 (CGNKRTRGC; SEQ ID NO: 2) and iRGD (CRGDKGPDC; SEQ ID NO: 3). However, one or more other members of a class of tumor-penetrating peptides having a R/KXXR/K (SEQ ID NO: 4) C-terminal peptide motifs may be used as a targeting domain to stimulate vascular permeability in addition to cell-specific targeting. In some to embodiments, such a targeting domain promotes rapid delivery of macromolecules and nanoparticles deep into the tumor parenchyma.

In some embodiments, one or more of the following non-limiting homing domains may be used:

| Peptide | Target |
|---|---|
| CDCRGDCFC (SEQ ID NO: 5) | RGD4C; $\alpha_v\beta_3$ integrins |
| CNGRC (SEQ ID NO: 6) | Angiogenic tumor vessels |
| CTTHWGFTLC (SEQ ID NO: 7) | Gelatinase homer; angiogenic vessels |
| F3 (34 aa) | Tumor neovasculature |
| CGKRK (SEQ ID NO: 8) | Squamous cell carcinoma |
| CDLTR (SEQ ID NO: 9) | Squamous cell carcinoma |
| CREAGRKAC (SEQ ID NO: 10) | Tramp Lymphatics |
| CAGRRSAY (SEQ ID NO: 11) | Tramp premalignant lymphatics |
| CRGDKGPDC (SEQ ID NO: 3) | iRGD; neuropilin-1 |
| CGNKRTRGC (SEQ ID NO: 2) | LyP-1; p32 on tumor cells and tumor lymphatics |

However, it should be appreciated that other homing domains (e.g., other cyclic peptide homing domains) may be used. In some embodiments, the targeting domain is less than 100, less than 50, less than 25, or less than 15 amino acids in length.

Nucleic Acid Binding Domain:

In some embodiments, a nucleic acid binding domain may include amino acid motifs that interact with or bind to specific nucleic acid sequences if sequence specificity is desired or tolerated. However, in many embodiments a nucleic acid binding domain is selected to promote non-specific interaction or binding with a nucleic acid (e.g., based on non-sequence-specific charge interactions with negatively charged nucleic acid backbone). Accordingly, a nucleic acid domain may include one or more basic amino acids (e.g., one or more Lysine or Arginine residues)

In some embodiments, an siRNA binding motif binds to siRNA in a sequence-independent manner. The siRNA binding motif serves to loosely associate with siRNA molecules that are to be delivered using a fusion polypeptide of the invention. The siRNA binding motif promotes the uptake and release of siRNA molecules based on a to loose charge interaction with the siRNA molecules. In some embodiments, the nucleic acid is reversibly associated with the polypeptide with a dissociation constant in the range of 1-100 nM, 1-50 nM, or 1-10 nM.

In some embodiments, the second domain of a polypeptide of the invention also has cell-penetrating properties (also referred to as protein transduction properties). Protein transduction is the process by which a peptide or protein crosses the cell plasma membrane. The recent discovery of several proteins which could efficiently pass through the plasma membrane of eukaryotic cells has led to the identification of a novel class of proteins from which peptide transduction domains have been derived. Protein transduction domains are typically cationic in nature. These cationic protein transduction domains track into lipid raft endosomes carrying with them their linked cargo and release their cargo into the cytoplasm by disruption of the endosomal vesicle. Examples of protein transduction domains include transportan (GWTLN-SAGYLLGKINLKALAALAKKIL; SEQ ID NO: 29), AntHD, TAT, VP22, cationic prion protein domains and functional fragments thereof. The disclosure provides methods and compositions that combine the use of siRNA binding domains with protein transduction functions such as transportan, with a cell-surface binding motif and a siRNA. In some embodiments, the structure of PTD such as TAT or penetratin may need to be modified by removing or replacing one or more basic amino acid residues to ensure optimal delivery to the target cells as described herein.

The siRNA binding domains with protein transduction functions will be capable of transducing at least about 20%, 25%, 50%, 75%, 80% or 90% of the cells of interest, more preferably at least about 95%, 98% and up to, and including, about 100% of the cells. Transduction efficiency, typically expressed as the percentage of transduced cells, can be determined by several conventional methods.

In some embodiments, a protein transduction function will be selected to manifest cell entry and exit rates that favor the delivery of at least picomolar amounts of the fusion molecule into the cell. The entry and exit rates of the protein transduction domain (PTD) and any cargo can be readily determined or at least approximated by standard kinetic analysis using detectably-labeled fusion molecules. Typically, the ratio of the entry rate to the exit rate will be in the range of between about 5 to about 100 up to about 1000.

In some embodiments, the nucleic acid binding/protein transduction motif of the second domain includes less than 9 basic amino acids (e.g., Arginines, Lysines, Histidines, or any combination thereof). In some embodiments, the motif has less than 8, less than 7, less than 6, less than 5, less than 4, less than 3, or less than 2 basic amino acids. In some embodiments, the motif has at least 2, at least 3, at least 4, at least 5, at least 6, at least 7, or at least 8, basic amino acids. Accordingly, in some embodiments, the motif has between 3 and 8, between 3 and 7, between 3 and 6, between 3 and 5, or 3-4 basic amino acids. In some embodiments, the motif has 4-8, 4-7, 4-6, or 4-5 basic amino acids. It should be appreciated that different amino acid configurations may be used. In some embodiments, a configuration may be designed or selected to promote the appropriate level of binding of the motif to a nucleic acid and/or to promote the appropriate level of protein transduction (also referred to as cell penetration) without promoting excessive non-cell-specific protein transduction and/or excessively tight nucleic acid binding. In some embodiments, at least two or three positively charged (e.g., basic) amino acids are provided for nucleic acid binding. In some embodiments, about six positively charged (e.g., basic) amino acids are used in conjunction with a tumor penetrating homing domain. In some embodiments, the basic amino acids may be provided as an uninterrupted series of basic amino acids. However, in some embodiments, an array (e.g., a regular array) of basic amino acids may be provided each separated by 1 or more (e.g., 2, 3, 4, 5, etc., or more) non-basic amino acids. In some embodiments, groups of 2 or more basic amino acids may be provided, each group separated from other groups by 1 or more (e.g., 2, 3, 4, 5, etc., or more) non-basic amino acids. In some embodiments, basic amino acids may be positioned to provide a particular 3-dimensional pattern of amino acids (e.g., a linear pattern or "stripe," a patch, or other 3-dimensional pattern). However, it should be appreciated that more or less basic amino acids may be used provided the motif has suitable binding and/or cell penetrating properties for delivering the nucleic acid of interest.

In some embodiments, the nucleic acid binding/protein transduction motif of the second domain is at least 10, 20, 30, 40, or 50 amino acids long, and includes less than 25% basic amino acids (e.g., Arginines, Lysines, histidines or any combination thereof). In some embodiments, the motif has less than 20%, less than 15%, or less than 10% basic amino acids. In some embodiments, the nucleic acid binding/protein transduction motif of the second domain includes about 5-25% basic amino acids. In some embodiments the motif can be more than 50 amino acids long.

In some embodiments, the second domain does not contain any additional amino acids (i.e., the nucleic acid binding/protein transduction motif represents the entire second domain). Accordingly, the second domain may be a PTD, and the PTD provides sufficient positive charges for nucleic acid binding.

An appropriate charge ratio of PTD to nucleic acid (e.g., the number of positive (e.g., basic) PTD amino acids relative to the number of negatively charged nucleotides (each negative charge corresponding to a nucleotide due to the presence of a negative phosphate backbone charge on each nucleotide), taking into account the relative molar amount of PTD to nucleic acid) may be used to reduce undesired non-specific cell targeting of a protein transduction domain A ratio of between about 2:1 to 3:1 may be used in some embodiments. Examples where this ratio was effective include TP (charge ratio of approximately 1.9:1), and 6R (charge ratio of approximately 2.8:1). Examples that did not work or worked less effectively or had reduced specificity include 9R-LyP1 (charge ratio of approximately 4.3:1), 12R-LyP1 (charge ratio of approximately 5.7:1), 15R-LyP1 (charge ratio of approximately 7.1:1), and TAT (charge ratio of approximately 4.3:1), Penetratin (charge ratio of approximately 3.3:1), and VP22 (charge ratio of approximately 4.3:1). This charge ratio suggests that in some embodiments an approximately 2-3:1 charge ratio between peptide and siRNA may be used to i) mask non-specific cellular entry by PTDs, and ii) enable efficient release once inside the cell.

In some embodiments, a domain (e.g., a PTD domain) having both nucleic acid binding and cell penetrating properties may be modified to further enhance cell penetration. In some embodiments, modification at the N-terminus of an N-terminal PTD domain allows for the free C-terminus of the targeting domain to be appropriately processed (e.g., proteolytically within the target cell) in order to release the nucleic acid being delivered In some embodiments, the modification may be a myristoylation (e.g., to further facilitate interactions with membrane lipids). In some embodiments, myristoylation of the PTD is helpful to promote endosomal membrane penetration. In some embodiments, other groups may used (for example, but not limited to, cholesterol, lipids, and fatty acids).

It should be appreciated that any of the polypeptides and/or nucleic acids can be to made by chemical synthesis or recombinant expression using techniques that are well known in the art. Complexation of polypeptides with nucleic acids can be achieved by mixing the nucleic acid with the polypeptide in an appropriate buffer such phosphate-buffered saline (PBS) with a pH of about 7.4, at an appropriate ratio Applications:

Aspects of the invention may be used to deliver any suitable nucleic acid including DNA, RNA, PNA, and/or other natural or synthetic nucleic acids. Non-limiting examples of nucleic acids that may be delivered include, dsRNA, snRNA, hnRNA, siRNA, antisense RNA, antisense DNA, aptamers, antagomirs, etc., or any combination thereof.

The ability to confer tissue-specific targeting also impacts the choice of mRNA targets. For example, cell-essential genes may become excellent cytotoxic tumor targets if their delivery can be made specific. As miRNA targets are emerging and clearly part of complex regulatory pathways, specific delivery will become even more important.

Aspects of the invention are useful in a variety of applications for either expressing an RNA or protein of interest (e.g., gene therapy or DNA vaccines) or for silencing an RNA or protein of interest (e.g., ribozymes, RNAi, or antisense).

In one such aspect, the invention features a method for expressing an RNA or protein molecule of interest in a cell. The method includes contacting a cell with a composition of the invention under conditions that desirably allow introduction of a nucleic acid into the cell and expression of an RNA or protein of interest encoded by a nucleic acid in the composition. In some embodiments, the cell has a mutation associated with a disease or disorder in an endogenous form of the RNA or protein of interest, and the nucleic acid encodes a form of the RNA or protein that is not associated with the disease or disorder. In certain embodiments, the RNA or protein of interest is from a pathogen, and the method causes an immune response against the RNA or protein of interest.

In another aspect, the invention features a method for inhibiting the expression of a target nucleic acid in a cell. The method includes contacting a cell with a composition of the invention under conditions that desirably allow introduction of a nucleic acid into the cell and expression of a ribozyme encoded by a nucleic acid in the composition. The ribozyme cleaves a target nucleic acid in the cell that is associated with a disease, disorder, or infection.

In a related aspect, the invention features another method for inhibiting the expression of a target nucleic acid in a cell. The method includes contacting a cell with a composition of the invention under conditions that desirably allow introduction of a nucleic acid into the cell. In some embodiments, a composition includes an siRNA, a first double stranded RNA (dsRNA) or a nucleic acid encoding a first double stranded dsRNA that has substantial sequence identity to a region of the target nucleic acid and specifically inhibits expression of the target nucleic acid. The method may further include introducing a short, second dsRNA or a nucleic acid encoding a short, second dsRNA that inhibits dsRNA-mediated toxicity into the cell.

In another aspect, the invention provides a method for treating, stabilizing, or preventing a disease, disorder, or infection in an animal. The method includes contacting an animal with a composition of the invention under conditions that desirably allow introduction of a nucleic acid into the animal. The composition includes an siRNA, a first dsRNA or a nucleic acid encoding a first double stranded dsRNA that has substantial sequence identity to a region of the target nucleic acid associated with the disease, disorder, or infection and specifically inhibits expression of the target nucleic acid. In some embodiments, the method further includes introducing a short, second dsRNA or a nucleic acid encoding a short, second dsRNA that inhibits dsRNA-mediated toxicity into the cell.

In another aspect, the invention features another method for inhibiting the expression of a target nucleic acid in a cell. The method that includes contacting a cell with a composition of the invention under conditions that desirably allow introduction of a nucleic acid into the cell. The composition includes an antisense nucleic acid that has substantial sequence identity to a region of the target nucleic acid and specifically inhibits expression of the target nucleic acid.

In yet another aspect, the invention features a method for treating, stabilizing, or preventing a disease, disorder, or infection in an animal. The method includes contacting an animal with a composition of the invention under conditions that desirably allow introduction of a nucleic acid into the animal. The composition includes an antisense nucleic acid that has substantial sequence identity to a region of the target nucleic acid associated with the disease, disorder, or infection and specifically inhibits expression of the target nucleic acid. In some embodiments, the target nucleic acid is associated with a to pathogen, such as a virus, bacterium, yeast, or infectious agent.

In some embodiments, genes that are difficult to drug may be targeted by delivering a gene-specific siRNA or other nucleic acid that can reduce the expression of one or more of the following genes or gene families: MYC, KRAS, ID family, CLDN3, ERBB3, BCL-2 family, or transcription factors. However, it should be appreciated that other genes (e.g., other oncogenes, or other disease-associated genes for which reduced expression can have therapeutic or other beneficial effects).

Accordingly, exemplary target nucleic acids to be silenced include nucleic acids associated with cancer or abnormal cell growth, such as oncogenes, and nucleic acids associated with an autosomal dominant or recessive disorder (see, for example, WO 00/63364, WO 00/44914, and WO 99/32619). Desirably, the dsRNA or antisense nucleic acid inhibits the expression of an allele of a nucleic acid that has a mutation associated with a dominant disorder and does not substantially inhibit the other allele of the nucleic acid (e.g., an allele without a mutation associated with the disorder). Other exemplary target nucleic acids to be silenced include host cellular nucleic acids or pathogen nucleic acids required for the infection or propagation of a pathogen, such as a virus, bacteria, yeast, protozoa, or parasite.

An "siRNA" molecule of the invention is a duplex consisting of a sense strand and complementary antisense strand, the antisense strand having sufficient complementary to a target mRNA sequence to direct a target-specific RNA silencing mechanism. In preferred embodiments, the antisense strand has sufficient complementary to the target mRNA to direct RNA interference (RNAi), as defined herein, i.e., the siRNA has a sequence sufficient to trigger the destruction of the target mRNA by the RNA silencing machinery or process. In alternative embodiments, the antisense strand of the siRNA has sufficient complementarity to a target mRNA sequence to direct translation repression of the target mRNA. In certain embodiments, the siRNA molecule has a length from 5-150 (e.g., about 10, 25, 50, 75, 100, 125) or more nucleotides, i.e., each strand comprises 5-150 (e.g., 10, 25, 50, 75, 100, 125) nucleotides (or nucleotide analogs).

One or both strands of the siRNA can also comprise a 3' overhang. As used herein, a "3' overhang" refers to at least one unpaired nucleotide extending from the 3'-end of a duplexed RNA strand. Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, or from about 1 to about 3 nucleotides in length and particularly 50 preferably from about 2 to about 4 nucleotides in length, and more preferably about 2 nucleotides in length.

By "dsRNA" is meant a nucleic acid containing a region of two or more nucleotides that are in a double stranded conformation. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000 or U.S. Ser. No. 60/130,377, filed Apr. 21, 1999. The dsRNA may be a single molecule with a region of self-complimentarity such that nucleotides in one segment of the molecule base pair with nucleotides in another segment of the molecule. In various embodiments, a dsRNA that consists of a single molecule consists entirely of ribonucleotides or includes a region of ribonucleotides that is complimentary to a region of deoxyribonucleotides. Alternatively, the dsRNA may include two different strands that have a region of complimentarity to each other. In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. Desirably, the regions of complimentarity are at least 70, 80, 90, 95, 98, or 100% complimentary. Desirable RNA/DNA hybrids include a DNA strand or region that is an antisense strand or region (e.g, has at least 70, 80, 90, 95, 98, or 100% complimentary to a target nucleic acid) and an RNA strand or region that is an sense strand or region (e.g, has at least 70, 80, 90, 95, 98, or 100% identity to a target nucleic acid). In various embodiments, the RNA/DNA hybrid is made in vitro using enzymatic or chemical synthetic methods such as those described herein or those described in WO 00/63364, filed Apr. 19, 2000 or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell.

By "antisense" is meant a nucleic acid, regardless of length, that is complementary to a coding strand or mRNA of interest. In some embodiments, the antisense molecule inhibits the expression of only one molecule of interest, and in other embodiments, the antisense molecule inhibits the expression of more than one molecule of interest. Desirably, the antisense nucleic acid decreases the expression or biological activity of an RNA or protein of interest by at least 20, 40, 50, 60, 70, 80, 90, 95, or 100%. An antisense molecule can be introduced, e.g., to an individual cell or to whole animals, for example, it may be introduced systemically via the bloodstream. Desirably, a region of the antisense nucleic acid or the entire antisense nucleic acid is at least 70, 80, 90, 95, 98, or 100% complimentary to a coding sequence, regulatory region (5' or 3' untranslated region), or an mRNA of interest. Desirably, the region of complementarity includes at least 5, 10, 20, 30, 50, 75, 100, 200, 500, 1000, 2000 or 5000 nucleotides or includes all of the nucleotides in the antisense nucleic acid.

In some embodiments, the antisense molecule is less than 200, 150, 100, 75, 50, or 25 nucleotides in length. In other embodiments, the antisense molecule is less than 50,000; 10,000; 5,000; or 2,000 nucleotides in length. In certain embodiments, the antisense molecule is at least 200, 300, 500, 1000, or 5000 nucleotides in length. In some embodiments, the number of nucleotides in the antisense molecule is contained in one of the following ranges: 5-15 nucleotides, 16-20 nucleotides, 21-25 nucleotides, 26-35 nucleotides, 3645 nucleotides, 46-60 nucleotides, 61-80 nucleotides, 81-100 nucleotides, 101-150 nucleotides, or 151-200 nucleotides, inclusive. In addition, the antisense molecule may contain a sequence that is less than a full length sequence or may contain a full-length sequence.

By "substantial sequence complementarity" is meant sufficient sequence complementarity between a dsRNA or antisense nucleic acid and a target nucleic acid for the dsRNA or antisense nucleic acid to inhibit the expression of the nucleic acid. Desirably, the sequence of the dsRNA or antisense nucleic acid is at least 40, 50, 60, 70, 80, 90, 95, or 100% complementary to the sequence of a region of the target nucleic acid.

Formulation and Delivery:

In some embodiments, compositions of the invention may be delivered using any suitable technique. For example, compositions may be provided for oral, intravenous, parenteral, subcutaneous, and/or other delivery route as aspects of the invention are not limited in this respect.

It should be appreciated that in some embodiments compositions of the invention may be formulated specifically for a particular delivery route. In some embodiments, a concentration or range of concentrations may be prepared for a particular delivery route.

Screening and Evaluation:

In some embodiments, aspects of the invention relate to methods of designing and/or screening for polypeptides that can be used for delivering nucleic acids (e.g., in a cell-specific form).

In some embodiments, libraries of polypeptides comprising two or more domains (e.g., libraries of fusion or tandem peptides comprising first and second domains derived from different molecules and/or designed for cell targeting and/or nucleic acid binding and/or protein transduction).

In some embodiments, polypeptides or libraries of polypeptides may be designed based on predicted properties of the motifs. In some embodiments, libraries may be synthesized to contain many different combinations of motifs. Regardless or the design and synthesis rationale, the library may be screened to identify polypeptides that confer desirable nucleic acid (e.g., siRNA) delivery to cell types of interest (e.g., diseased cells, for example cancerous cells).

In some embodiments, one or more of the following parameters may be evaluated: in vitro and/or in vivo delivery, nucleic acid binding, cell surface expression of a target molecule, receptor specific uptake, in vitro and/or in vivo gene silencing, targeted delivery of nucleic acid in vivo, pharmacokinetics and biodistribution of peptide/nucleic acid complexes, targeting of complex in tumor histological sections, tumor-specific nucleic acid delivery and knockdown in multiple tumor types, off-target silencing and immunostimulatory effects of delivered nucleic acids, or any combination thereof.

In some embodiments, aspects of the invention relate to siRNA delivery. According to aspects of the invention, general purpose RNA interference offers an attractive means to silence expression of genes, particularly for genes previously considered to be "undruggable" by small molecule or antibody means. However, systemic delivery of siRNA has been challenging due to pharmacokinetic properties resulting from their small size, the requirement for delivery of siRNA into the cytosol, and their susceptibility to serum nucleases.

Delivery vehicles for siRNA include complexation with cationic lipids, polymers, or proteins. Because these vehicles rely on the physical properties of RNA, the delivery is highly modular: one can alter the mRNA target by changing the siRNA sequence without interfering with the formulation. Recently, peptides with cell penetrating properties (also known as protein transduction domains) have emerged as an efficient delivery vehicle capable of transfecting many cell types (Eguchi, Meade et al. 2009). However, existing delivery technology does not provide predictive or modular platforms that can be used to deliver any nucleic acid of interest to any cell of interest.

In some embodiments, aspects of the invention provide a predictive method to restrict the delivery of siRNA to specific tissues based on known cell surface markers. In some embodiments, cell surface markers can be targeted using cyclic peptides that bind to specific cells of interest. Phage-display methods that provide libraries of cyclic peptides that bind to specific cells of interest have been developed (Pasqualini and Ruoslahti 1996; Laakkonen, Porkka et al. 2002; Laakkonen, Akerman et al. 2004). In some embodiments, aspects of the invention use one or more cyclic peptides in tandem configuration with appropriate cell penetrating peptides to confer specific knockdown of gene expression in selected cells.

These and other aspects of the invention are illustrated by the following non-limiting examples. Some of the following examples illustrate the use of a library of tandem peptides with protein transduction domains and homing peptides that bind to known cell surface receptors (e.g. the Lyp1 binds cell surface p32). Upon complexation with siRNA, nanoparticles that are formed display homing peptides in a multivalent fashion, thereby increasing their binding affinity. Not all protein transduction domains are able to confer delivery of siRNA to the cytosol in a receptor-specific fashion. Formulations that fail are either not specific (e.g., could not be inhibited by competition at the receptor) or cannot produce effective knockdown (e.g., because of inefficient entry or endosomal escape). In some embodiments, cyclic homing peptides such as Lyp1 in tandem with the PTD from transportan (TP) are effective for targeted delivery of siRNA to cells of interest (e.g., aberrantly expressed p32 on tumor cells and lymphatic cells). The resultant nanoparticles efficiently bind cells in a receptor-specific fashion in vitro, home to tumors in vivo, silence target mRNA in cells of interest, and are stable, non-stimulatory, and longer circulating in vivo than naked siRNA. Some of the following examples illustrate how TP-LyP1 tandem peptides enable targeted efficient delivery of siRNA to ovarian cancer in vivo. However, it should be appreciated that the delivery platform is modular in that both homing and cell penetrating domains can be varied to independently from each other to identify the best performing peptide, and be easily adaptable to other homing domains and cancer models. In addition, the tandem presentation of a cell penetrating domain along with a homing peptide domain rendered the peptide highly specific while still efficient at transducing siRNA, enabling targeted delivery to subsets of tumor cells that may be under stress [Fogal, V. et al. Mitochondrial p32 protein is a critical regulator of tumor metabolism via maintenance of oxidative phosphorylation. *Mol Cell Biol* 30, 1303-1318, (2010)] and highly susceptible to RNAi, while minimizing toxicity. However, it should be appreciated that the embodiments illustrated in the examples are non-limiting.

EXAMPLES

Example 1

Materials and Methods

Cell Lines:
HeLa-GFP and MDA-MB-435 cells were cultured in Dulbecco's modification of Eagle's medium (DMEM, purchased from Invitrogen) with 10% bovine serum (Invitrogen), 5 I.U. penicillin, and 5 µg/mL streptomycin. OVCAR-8, OVCAR-4, EFO-21 cells were cultured in RPMI 1640 medium (Invitrogen) with 10% fetal bovine serum (FBS, Invitrogen), 2 mM glutamine, 5 I.U. penicillin, and 5 µg/mL streptomycin. All cells were cultured at 37° C. with 5% $CO_2$. OVCAR-8 cell line stably expressing firefly luciferase was generously provided by Dr. Livingston. OVCAR-4 and EFO-21 cells were generously provided by Dr. William C. Hahn.

Peptides and siRNAs:
The tandem peptide library used in this work was synthesized via standard FMOC solid-phase peptide synthesis and purified by high-performance liquid chromatography at the MIT Biopolymers Core, Tufts University Core Facility or CPC Scientific, Inc. The tandem peptides were then cyclicized by bubbling air into 10 µM aqueous peptide solutions for 24 h, followed by lyophilisation and storage at −20° C. for later use.

All siRNAs were obtained from Dharmacon, Inc. The sequences of siRNAs (5'-3') are as follows: siGFP (GGCUACGUCCAGGAGCGCA; SEQ ID NO: 12), siLUC (CUUACGCUGAGUACUUCGA; SEQ ID NO: 13), siBgal-728 (CUACACAAAUCAGCGAUUU; SEQ ID NO: 14), siID4_568 (GAUAUGAACGACUGCUAUA; SEQ ID NO: 15), siID4_621 (CAACAAGAAAGUCAGCAAA; SEQ ID NO: 16), siID4_564 (GUGCGAUAUGAACGACUGCUA; SEQ ID NO: 17), and siID4_1195 (CCGACUUUAGAAGCCUACUUU; SEQ ID NO: 18).

Fluorescent labelling of siRNA. siRNAs bearing 3'-amine on the sense strand was reacted in PBS with twenty-fold molar excess of Vivotag S-750 amine-reactive dye (Visen Medical, Inc.) for 1 h at 37° C. The reaction mixture was then precipitated overnight at −20° C. in 0.5 M NaCl and 40% ethanol. Precipitated siRNA was pelleted through centrifugation at 8000×g for 20 minutes at 4° C., washed once with 70% ethanol, and centrifuged again before air-dried. This labelling process was repeated to yield approximately 3.5 fluorophores per siRNA duplex.

Gel-Shift and Stability Assays:
For the gel-shift assay, siRNA (e.g., 100 pmol) was mixed with specified quantity of tandem peptide in phosphate buffered saline (PBS) for 10-15 min at room temperature. The mixture was analyzed by non-denaturing gel electrophoresis using a 15% acrylamide gel for siRNA, stained with SYBR-Gold, and visualized under UV light.

For the siRNA stability assay, siRNA (100 pmol) was mixed with TP-LyP1 or 6R-LyP1 (2 nmol in PBS for 10-15 min at room temperature. Naked siRNA or peptide-complexed siRNA was then added to 100% murine serum (10:1 v/v) and incubated at 37° C. for the indicated times, after which the RNA is extracted and precipitated according to established protocols, separated on a 15% TBE gel, stained with SYBR-Gold, and visualized under UV light.

Peptide Uptake and Gene Silencing:
For the initial screen, HeLa cells stably expressing destabilized GFP were cultured in 96-well plates to ~70-80% confluence. siRNA (0-100 nM) was incubated with 20-fold molar excess of tetramethylrhodamine-labelled tandem peptides in PBS for 10-15 min at room temperature, then incubated over cells in DMEM for 4 h at 37° C., after which the medium was replaced. The complexes were then added to HeLa cell cultures and incubated for 4 h at 37° C., after which the medium was replaced with 100 µL of fresh medium with 10% serum. Transfection with Lipofectamine RNAiMAX was performed in accordance with the manufacturer's instructions. The cells were cultured for an additional 48 h-72 h before being examined by flow cytometry on a BD LSRII instrument using filters for GFP (FITC) and TAMRA. For competition experiments with free LyP-1 peptide, cells were pre-incubated with unlabeled LyP-1 peptide or ARAL control peptide at specified concentrations for 1 h at 37° C. before treatment with peptide/siRNA complexes.

For ID4 silencing, siRNAs targeting different sequences of the ID4 gene (100 pmol) were mixed with TP-LyP1 peptide at a molar ratio of 1:20 (siRNA to peptide) in PBS and added to OVCAR-8, OVCAR-4, or EFO-21 cell cultures (plated at $0.5 \times 10^6$ cells in 6-well plates 24 h prior) in DMEM for 4 h at 37° C. and was then replaced with fresh serum-containing media. Cell lysates were collected 48 h after transfection for western blotting analysis.

Western Blotting:

Cells were washed three times with 4° C. PBS 48 h after transfection. Cells were lysed in RIPA buffer (Millipore) containing a protease inhibitor cocktail (Roche) on ice for 10 minutes. The resulting cell lysate was subjected to electrophoresis on a 12% acrylamide gel (Bio-Rad) and transferred to a poly(vinylidene diluoride) membrane. The membrane was probed with anti-α-tubulin antibodies (Invitrogen), polyclonal anti-p32 or anti-ID4 antibodies (Abcam) and detected with secondary antibodies (IRDye 680 goat anti-mouse IgG or IRDye 800 goat anti-rabbit IgG (Li-COR)). The blots were scanned using the Odyssey infrared imaging system (Li_COR Biosciences) and the ratio of band intensities of ID4 normalized to tubulin was measured using Image J.

Cell Proliferation Assay:

To measure the cytotoxicities of nanocomplexes in vitro, HeLa cells grown in 96-well plates at ~70-80% confluency were incubated in triplicate with specified concentrations of nanocomplex formulations in serum-free DMEM for 24 h. Viability was measured using the fluorogenic intracellular esterase sensor Calcein acetoxymethylester (Invitrogen). To measure the cytotoxicity of ID4 suppression, OVCAR-8 and OVCAR-4 cells grown in 6-well plates at 70-80% confluence were transfected twice on two consecutive days with nanocomplexes containing siRNA against ID4 (100 pmol) or containing siRNA against GFP. Twenty-four (24) h after the second transfection, cells were trypsinized and plated in 96-well plates in quadruplicate. The plate was analyzed 24 h later using MTT (3-(4,5-Dimethylthiazol-2-yl)-2,5-diphenyltetrazolium bromide) (Invitrogen), Calcein acetoxymethylester (Invitrogen), or Celltiter-Glo assays (Promega) according to manufacturer's instructions.

Flow Cytometry:

Fluorescence-activated cell sorting (FACS) analysis of cell-surface p32 was done on live cells. Approximately $2.5 \times 10^5$ cells were stained with a polyclonal anti-full-length/NH2-terminal p32 or rabbit IgG isotype control (1 µg per $1 \times 10^6$ cells) and Alexa-647 goat anti-rabbit secondary antibody, each for 40 min at 4° C., analyzed by gating for propidium iodide-negative (live) cells.

For analysis of apoptosis and cells entering S-phase, cells were washed with PBS, adjusted to a cell density of $2.5 \times 10^5$ per ml, and resuspended in 100 µL of 1× Annexin-V binding Buffer (BD Biosciences, San Jose, Calif.). Cells were incubated with Annexin V—FITC for 15 minutes in the dark according to the manufacturer's recommendation (BD Biosciences, San Jose, Calif.). Binding buffer (e.g., 400 µl) was added and Annexin-V-positive cells were analyzed by flow cytometry.

For analysis of apoptosis and cells entering S-phase, cells were washed with PBS, adjusted to a cell density of $2.5 \times 10^5$ per ml, and resuspended in 1× Annexin-V binding Buffer (BD Biosciences, San Jose, Calif.).

Inhibition of Endocytosis and Imaging:

HeLa cells grown in 96-well plates at ~70% confluence were incubated with small molecule inhibitors for 1 h at 37° C., followed by incubation with tetramethylrhodamine-labeled TP-LyP1 (3 µM) or TPNs containing both labeled peptide (3 µM) and GFP siRNA (100 nM) for an additional hour at 37° C. The cells were washed three times with cold PBS and were subsequently either imaged with a CCD camera mounted on a Nikon TE200 inverted epifluorescence microscope (for peptide-only), or trypsinized for flow cytometry analysis by the BD-LSR II system to assess GFP expression (for incubations with nanocomplexes).

Cytotoxicity Assays:

Cytotoxicity assessments were conducted on HeLa cells in 96-well plates grown to ~70-80% confluency. Cells were incubated in triplicate with specified concentrations of tandem peptide/siRNA formulations in serum-free DMEM for 24 h. Cells were then washed three times in PBS and assessed for viability using the fluorogenic intracellular esterase sensor Calcein acetoxymethylester (Invitrogen).

For ID4 knockdown experiments, OVCAR-8, OVCAR-4, and EFO-21 cells grown in 6-well plates at 80% confluence were transfected twice on two consecutive days with TP-LyP1/siRNA against ID4 (100 pmol) or control siRNA against GFP. 24 h after the second transfection, the cells were trypsinized and plated in 96-well plates at 5000 cells/well in quadruplicate in RPMI-1640 containing 10% FBS. The plate was analyzed 24 h later using MTT (3-(4,5-Dimethylthiazol-2-yl)-2,5-diphenyltetrazolium bromide) (Invitrogen), Calcein acetoxymethylester (Invitrogen), or the Celltiter-Glo assay (Promega) according to manufacturer's instructions.

Animal Experiments and Delivery of Nanocomplexes In Vivo:

Female Balb/c and nude NCR mice (Charles River Laboratories) were obtained at 4-6 weeks of age. All animal experiments were approved by the MIT Committee on Animal Care under approved protocols.

For circulation and targeting experiments, 5 nmol near-infrared fluorophore (VivoTag 750; ViSen Medical) labelled siRNA was complexed to targeted tandem peptides (at a molar ratio of 1:20 siRNA to peptide) in 5% glucose and injected either intravenously or intraperitoneally into mice bearing bilateral subcutaneous MDA-MB-435 tumors on the flank. The mice were imaged under anesthesia at specified times using the IVIS 200 imaging system (Caliper Life Sciences). Blood was periodically drawn retroorbitally and near-infrared fluorescence from circulating siRNAs was measured using the Odyssey imaging system (Li-COR Biosciences). The organs (bladder, kidneys, liver, spleen, heart, brain, lung, and skin) were harvested 8 h after injection once the circulating nanocomplexes were cleared and were also imaged using IVIS. Tumor explants were examined using the Odyssey imager using an excitation wavelength of 785 nm To test knockdown of luciferase expression in vivo, mice bearing intraperitoneal MDA-MB-435 cells expressing luciferase were injected with TP-LyP1/siLUC at specified doses (2.5 mg/kg and 5 mg/kg). Control mice received saline, TP-LyP1 with no siRNA or with an irrelevant siRNA against GFP, or TP-ARAL peptide complexed to siLUC (all 5 mg/kg). Whole-animal imaging of luciferase activity was performed 48 h later. To measure the duration of luciferase silencing, bioluminescence imaging was performed at specified time points.

Immunoblotting:

Cell lysates were prepared by scraping cells in lysis buffer [50 mM Tris HCl (pH 8), 150 mM NaCl, 1% Nonidet P40, 0.5% sodium deoxycholate and 0.1% SDS] containing complete protease inhibitors (Roche) and phosphatase inhibitors (10 mM Sodium Floride and 5 mM Sodium Orthovanadate). Protein concentration was measured by using BCA Protein Assay kit (Pierce). An equal amount of protein (30 µg) was separated by NuPAGE Novex Bis-Tris 4-12% gradient gels (Invitrogen) and then transferred onto a polyvinylidene difluoride membrane (Amersham). The membrane was then incubated with primary antibody for 1 h at room temperature. Antibodies against ID1 (sc-488), ID2 (sc-489), ID3 (sc-490), ID4 (sc-13047), K-RAS (sc-30) and H-RAS (sc-29) were purchased from Santa Cruz Biotechnology. Antibodies specific Caspase-3 (#9665), MEK (#9122), PARP (#9532) and phospho-ERK1/2 (#9101) were from Cell Signaling Technology. Antibody specific for HOXA9 (#07-178) was from Millipore. Antibody specific for α-tubulin was from Invitrogen. After incubation with the appropriate horseradish peroxidase-linked secondary antibodies (Bio-Rad), signals were visualized by enhanced chemiluminescence plus Western blotting detection reagents (Amersham). Expression of β-actin was also assessed as an internal loading control by using a specific antibody (sc-8432-HRP, Santa Cruz) Immunoblots of cell lysates after TPN treatment were incubated with IRDye 680 goat anti-mouse IgG or IRDye 800 goat anti-rabbit IgG (Li-COR) and scanned using the Odyssey infrared imaging system (Li-COR). Intensities of bands were quantified by LabWorks image analysis software (UVP) or ImageJ (http://rsbweb.nih.gov/ij/).

Real-Time Quantitative Reverse-Transcription PCR.

Total RNA was extracted with Trizol reagent (Invitrogen). 4 µg of total RNA for each sample was used to synthesize the first-strand cDNA by using Oligo(dT)$_{20}$/random hexamer primer cocktails and SuperScript III reverse transcriptase (Invitrogen). Quantitative PCR reactions were performed using SYBR green PCR Master Mix (Applied Biosystems). The primer sequences used are as follows: ID4 (forward: 5'-CCGAGCCAGGAGCACTAGAG-3', (SEQ ID NO: 19); reverse: 5'-CTTGGAATGACGAATGAAAACG-3', (SEQ ID NO: 20)), HOXA3 (forward: 5'-TGCTTTGTGTTTTGTCGAGACTC-3', (SEQ ID NO: 21); reverse: 5'-CAACCCTACCCCTGCCAAC-3', (SEQ ID NO: 22)), HOXA7 (forward: 5'-TATGTGAACGCGCTTTTTAGCA-3', (SEQ ID NO: 23); reverse: 5'-TTGTATAAGCCCGGAACGGTC-3', (SEQ ID NO: 24)), HOXA9 (forward: 5'-GAGTGGAGCGCGCATGAAG-3', (SEQ ID NO: 25); reverse: 5'-GGTGACTGTCCCACGCTTGAC-3', (SEQ ID NO: 26)) and GAPDH (forward: 5'-CCTGTTCGACAGTCAGCCG-3', (SEQ ID NO: 27); reverse: 5'-CGACCAAATCCGTTGACTCC-3', (SEQ ID NO: 28)). Triplicate reactions for the gene of interest and the endogenous control, (GAPDH) were performed separately on the same cDNA samples by using the ABI 7900HT real time PCR instrument (Applied to Biosystems). The mean cycle threshold (Ct) was used for the ΔΔCt analysis method (ABI User Bulletin #2).

Systemic administration and in vivo characterization of TPNs. For circulation experiments, 5 nmols of near-infrared fluorophore (Vivotag-750) labeled siRNA was complexed to tandem peptides (at a molar ratio of 1:20 siRNA to peptide) in 5% glucose and injected either intravenously or intraperitoneally into mice bearing bilateral subcutaneous MDA-MB-435 tumors on the flanks. The mice were imaged at specified times using the IVIS 200 imaging system (Caliper Life Sciences). Blood was periodically drawn retroorbitally and near-infrared fluorescence from circulating siRNAs was measured using the Odyssey imaging system (Li-COR Biosciences). The organs were harvested 6 h after injection and were also imaged using IVIS. Tumor explants were examined at higher resolution (84 µm) using the Odyssey imager with an excitation wavelength of 785 nm. To study time-dependent homing and tumor penetration in OVCAR-8 tumors, TPNs carrying FAM labeled-siRNA were intravenously injected to tumor bearing mice (5 nmols siRNA/injection). Tumors and tissues were collected 6 h later for subsequent analyses by immunofluorescence or quantification of total injected dose.

To determine the % injected dose accumulated in the tissue, organs and tumors harvested from mice were pulverized under liquid nitrogen and homogenized in 10 mM Tris buffer with 1% SDS. The homogenate was heated at 95° C. for 10 minutes and centrifuged at 14,000×g. Fluorescence of the lysate was measured using the Odyssey imager. To generate a standard curve for each organ, organs and tumors from uninjected animals were processed and known amounts of fluorescent siRNAs were spiked into the lysates. The lysates were imaged under the same settings, and the integrated fluorescence intensities versus siRNA concentrations were fitted with a 3-parameter exponential equation (f=y0+a*(1−exp(−b*x)); SigmaPlot).

Animal Model of Metastatic Ovarian Cancer:

All xenograft animal studies were conducted in accordance with guidelines from the MIT Committee on Animal Care with approved protocols.

For the OVCAR-4 tumor model, 3×10$^6$ OVCAR-4 cells mixed with Matrigel were implanted in the subcutaneous space on the bilateral flanks of 4- to 6-week-old NCr/nude mice (Charles River Laboratories). Once tumors have established, animals were divided into cohorts of five mice each and were treated with saline, TPNs containing ID4-specific siRNA, Claudin-3-specific siRNA, GFP-specific siRNA (all at 1 mg siRNA/kg body weight/injection), or no siRNA every 3 days. For the OVCAR-8 tumor model, OVCAR-8 cells stably expressing firefly luciferase were injected intraperitoneally into 4- to 6-week-old NCr/nude mice (Charles River Laboratories) at 10$^6$ cells per mouse. Two to three weeks after injection, tumor establishment was confirmed by an increase in total bioluminescence signal. The animals were then randomly divided into cohorts of five mice each. The first cohort received nanocomplexes containing TP-LyP1 and siRNA against ID4 (siID4_568 and siID4_621, 5 mg siRNA/kg body weight/injection).

For all treatments, siRNA was mixed with peptide at a molar ratio of 1:20 (peptide to siRNA) in 500 µL of PBS with 5% glucose, and injected intraperitoneally. Treatments were repeated twice weekly for 14 days, after which the dose was reduced to once weekly for another 3 weeks. Animals were euthanized 24 h after the last injection, and tumors/organs were harvested for immunostaining analyses.

Whole-animal optical imaging to assess luciferase activity was performed by using an In Vivo Imaging System (IVIS, Caliper Life Sciences) every 3 days for the duration of the treatment. Mice were anesthetized using isofluorane, injected with 150 mg/kg D-luciferin (Promega), and imaged 10-15 min after injection once the signal has peaked.

Immunostaining and Analysis:

For histological analysis, frozen sections of tumours were prepared (harvested tumors were fixed in 4% paraformaldehyde at 4° C. overnight, soaked in 30% sucrose (w/v) for 24 h, then snap frozen). The sections were first fixed 4% paraformaldehyde. Rat anti-mouse CD-31 (1:50, BD PharMingen) and a polyclonal anti-full length p32 antibody were used for immunochemical staining. Rat or rabbit IgGs were used as isotype controls. Sections were washed and detected with AlexaFluor-488 goat anti-rat or anti-rabbit IgG (1:1000; Invitrogen). The slides were counterstained with DAPI and mounted on glass slides for microscopic analysis. At least three images from representative microscopic fields were analyzed for each tumour sample using the ImageJ software.

Immunogenicity Studies in Mice:

Balb/c mice were injected intravenously or intraperitoneally with TP-LyP1 complexed to specified siRNAs against ID4, GFP, firefly luciferase, and siBgal-728. siBgal-728 encapsulated in Lipofectamine RNAiMAX was used as a positive control. Serum samples obtained 6 h after injection were processed for measurements of INF-α, TNF-α, and IL-6 by the enzyme-linked immunosorbent assay (PBL Biomedical Laboratories and BD Biosciences), in accordance with manufacturer's instructions.

Statistical Analysis:

Statistical analyses were performed using built-in statistical functions in GraphPad Prism (GraphPad Software). Tumor burden between different cohorts and averaged fluorescence intensities from immunofluorescence staining, IHC, and western blots were analyzed using one-way ANOVA and appropriate post-hoc tests.

Example 2

Figure 2A:
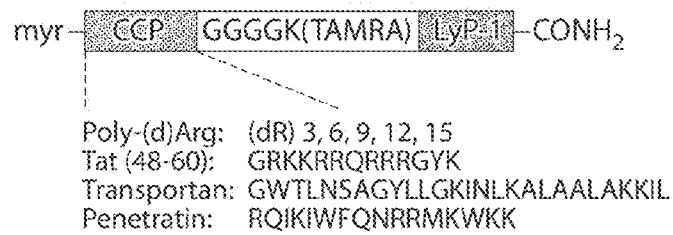
FIG. 2A is a schematic representation of siRNA-bound tandem peptides bearing a cyclic homing domain, a cell penetrating domain, and a linker.
Figure 2B:
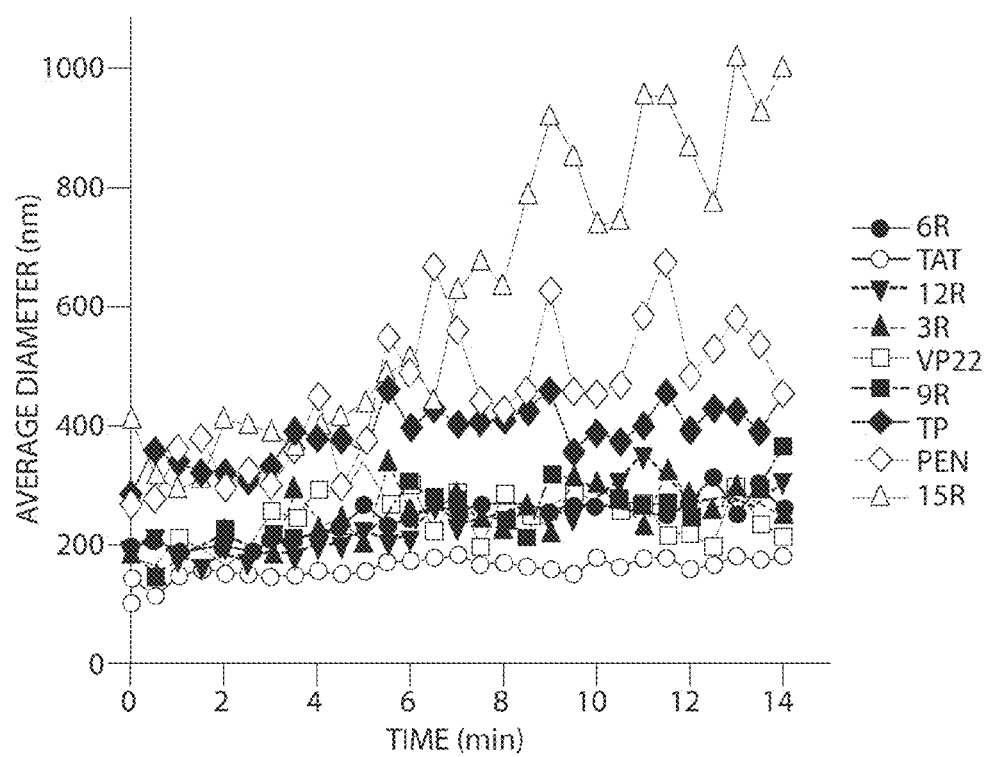
FIG. 2B shows the changes in size over time as measured by dynamic light scattering of peptide-siRNA complexes in buffered saline over time.
Figure 2C:
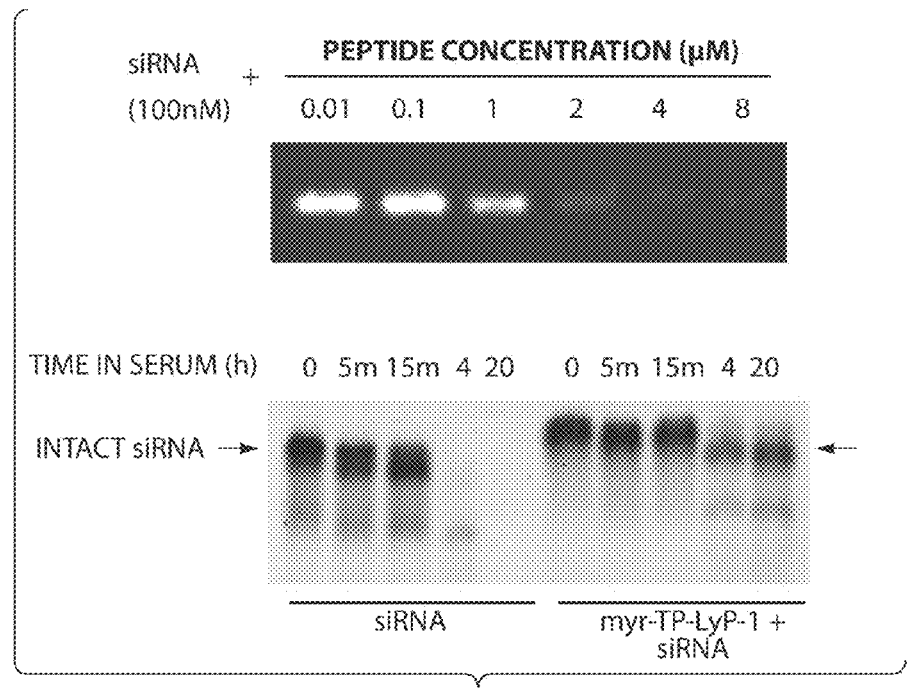
FIG. 2C, top panel, is an agarose gel analysis of free siRNA complexed to tandem peptide at various molar ratios; bottom panel is an agarose gel analysis of free or peptide-complexed siRNA in mouse serum at 37° C. for up to 20 h. Naked, unmodified siRNA is completely degraded by 4 h.

A peptide-siRNA nanocomplex containing siRNA non-covalently bound to a tandem peptide was designed to include a cyclic homing domain and a membrane-translocating domain, which targets tumors and delivers siRNA with high specificity and efficiency in vivo. A tandem peptide library was synthesized with variable cell penetrating domains reported in the literature and a fixed cyclic homing domain (LyP-1) that targets tumor-associated lymphatics and tumor cells in certain tumors [Laakkonen, P., Porkka, K., Hoffman, J. A. & Ruoslahti, E. A tumor-homing peptide with a targeting specificity related to lymphatic vessels. *Nat Med* 8, 751-755, (2002)]. See FIGS. 2A and 6A. This nine-amino acid homing domain (Cys-Gly-Asn-Lys-Arg-Thr-Arg-Gly-Cys) (SEQ ID NO: 2) binds to p32 or gC1q receptor, a mitochondrial protein aberrantly expressed at the tumor cell surface [Fogal, V., Zhang, L., Krajewski, S. & Ruoslahti, E. Mitochondrial/cell-surface protein p32/gC1qR as a molecular target in tumor cells and tumor stroma. *Cancer Res* 68, 7210-7218, (2008)]. The N-terminus of the tandem peptide is myristoylated to facilitate interactions with membrane lipids. Furthermore, the homing and cell penetrating domains are separated by a four-glycine spacer to ensure that complexation with siRNA does not interfere with tumor targeting. All peptides from the library were able to electrostatically bind siRNA and form stable nanocomplexes as assessed by dynamic light scattering (FIGS. 2B and 6B). The binding affinity of peptide to siRNA was determined in a gel-shift assay. At a molar ratio of 1:20 siRNA to peptide, nearly all of the free siRNA was bound to peptide (FIG. 2C, top) and siRNA is protected against degradation from serum nucleases. At an optimal complexation ratio of 1:20 siRNA to peptide, TPNs extended the half-life of siRNA to >12 h in serum. After incubation in murine serum for 24 h at 37° C., complete degradation of naked siRNA was observed, whereas 70% of the peptide-bound siRNA remained intact (FIG. 2C, bottom, and FIGS. 2I and J), suggesting suitability for in vivo experiments. The nanocomplexes were also found to be non-cytotoxic, as over 85% of the cells were viable 24 h after treatment with 3-50 µM peptide and 100 nM siRNA (FIG. 7).

The library of TPNs was screened for both cellular uptake in HeLa cells expressing p32 and suppression of green fluorescent protein (GFP). Uptake of TPNs was found to be dependent on the homing domain as quantified by monitoring tetramethylrhodamine labeled peptides by flow cytometry. To determine the ability of the tandem peptide library to deliver siRNA into cells, tetramethylrhodamine labelled peptides were pre-mixed with siRNA and incubated over Hela cells, which express p32 on the cell surface.

Figure 2D:
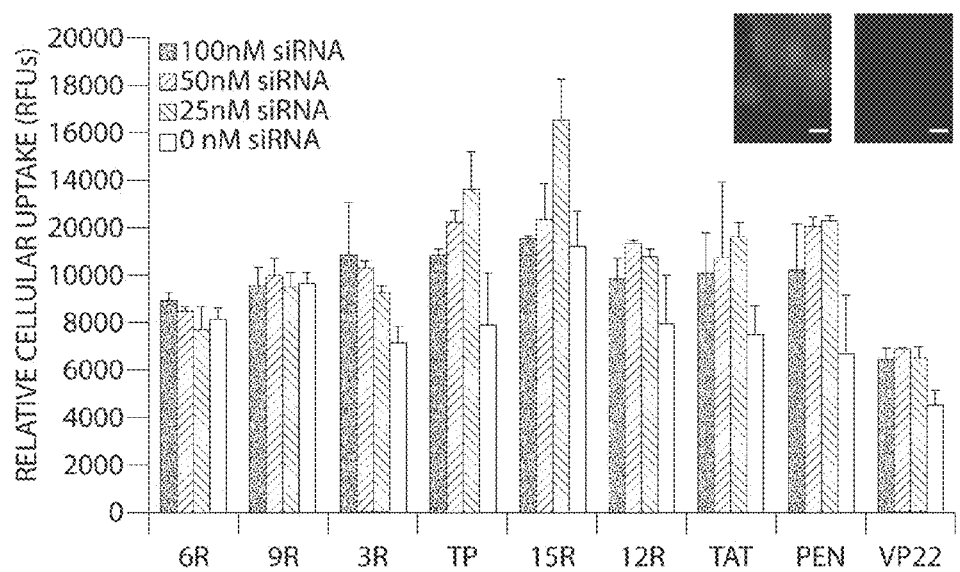
In FIG. 2D HeLa cells were treated with 0-100 nM siRNA bound to tetra-methyl-rhodamine (TAMRA) labeled tandem peptides at a molar ratio of 1:20 and cellular uptake assessed by flow cytometry. For 0 nM siRNA, 2 uM of the tandem peptide was used. Microscopy analyses showed binding of LyP-1 targeted nanocomplex but not controls to MDA-MB-435 cells (inset).

Flow cytometry analysis indicated that internalization of nanocomplexes occurred after 1 h of incubation (FIG. 8B). After 4 h, all targeted nanocomplexes were efficiently taken up, whereas no uptake was seen with untargeted peptide/siRNA complexes (FIG. 2D).

Figure 2E:
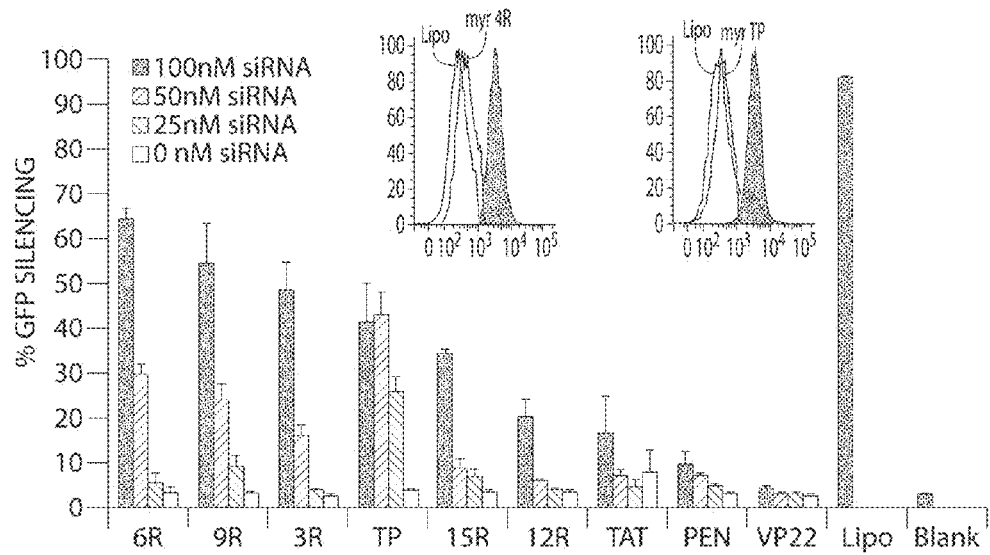
In FIG. 2E HeLa cells stably expressing a destabilized GFP were transduced with GFP siRNA complexed to peptides from the library. The amount of GFP silencing was determined by flow cytometry 48 h later. Lipofectamine was used as a positive control. % knockdown was normalized to GFP signal of untreated cells. Representative data for 6R-, 9R-, and TP-LyP1 peptides (inset) and cumulative data from three independent experiments are shown.

Although the above results showed tandem peptides could form stable complexes with siRNA and efficiently transduce them into cells, they do not establish functional delivery for gene silencing. The gene suppression activity of tandem peptide mediated siRNA delivery was evaluated. HeLa cells stably expressing a destabilized green fluorescence protein (dGFP) were treated with GFP-targeting siRNA bound to either tandem peptides or lipofectamine, and GFP expression was analyzed 48 h later. Four tandem peptides (6R, 9R, and TP-LyP1) were found to efficiently deliver siRNA that silenced GFP expression by ≈40-60%. In contrast, other members of the library showed cellular uptake but failed to induce gene silencing, possibly due to insufficient decomplexation of siRNA or endosomal entrapment (FIG. 2E).

After the delivery efficiency of tandem peptides was probed, the specificity of siRNA delivery due to LyP-1 homing to the p32 receptor was evaluated. MDA-MB-435 cells expressing p32-directed shRNA cells showed minimal levels of total and surface levels of p32 compared to cells with a control shRNA (FIG. 9A). When treated with targeted tandem peptides bearing LyP-1 (TP-LyP1) or a control peptide (TP-ARAL), cells with down-regulated p32 expression showed reduced TP-LyP1 binding relative to control shRNA cells, whereas binding of TP-ARAL was unaffected (FIG. 9B). Similar results were obtained with 6R-LyP1.

Collectively, these results illustrated that 6R-LyP1 and TP-LyP1 nanocomplexes enabled efficient and p32-dependent delivery of siRNA in vitro.

Example 3

To identify the mechanism by which tandem peptides enter cells, these experiments were repeated in the presence of a variety of endocytosis inhibitors [Veldhoen, S., Laufer, S. D., Trampe, A. & Restle, T. Cellular delivery of small interfering RNA by a non-covalently attached cell-penetrating peptide: quantitative analysis of uptake and biological effect. *Nucleic Acids Res* 34, 6561-6573, (2006)]. Cell binding and GFP knockdown were significantly decreased when cells were treated with amiloride, β-cyclodextrin, or PDMP, known inhibitors of macropinocytosis and lipid-raft. Deoxyglucose, an inhibitor of ATP biosynthesis, also inhibited GFP knockdown (FIG. 10). Thus, tandem peptides are taken up by cells mainly via macropinocytosis and lipid-raft.

Example 4

To further confirm the uptake specificity of those tandem peptide candidates (6R, 9R, and TP) that showed efficient GFP knockdown, free LyP-1 peptide was added to HeLa cells along with nanocomplexes. Dose-dependent inhibition of GFP silencing was observed for two tandem peptides (TP-LyP1 and 6R-LyP1) as the concentration of free LyP-1 increased from 5 to 20 µM, suggesting LyP-1 and the nanocomplexes compete for binding to the common p32 receptor (FIGS. 2F-H), whereas competition with a control peptide (ARAL) had no effect (data not shown).

Figure 2F:
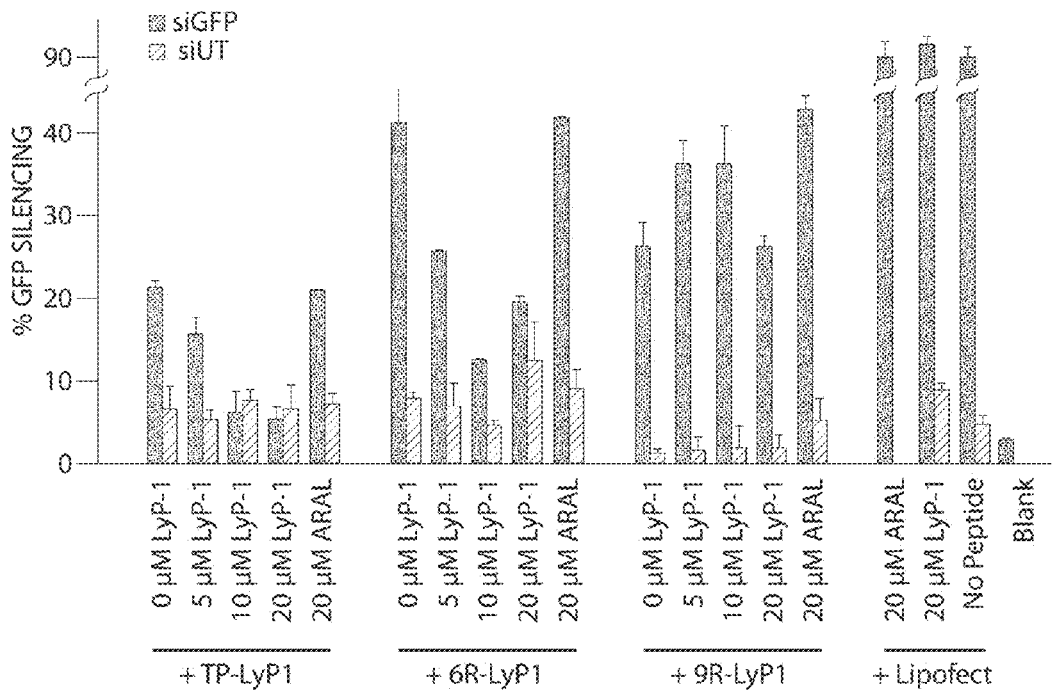
In FIG. 2F GFP silencing was re-examined in HeLa cells treated with siRNA delivered by three different tandem peptides: TP-LyP1, 6R-LyP1, and 9R-LyP1, in the presence of either free LyP-1 peptide at concentrations from 5 to 20 μM or a control peptide (ARAL, 20 μM). Transfection by lipofectamine was used as a positive control.
Figure 2G:
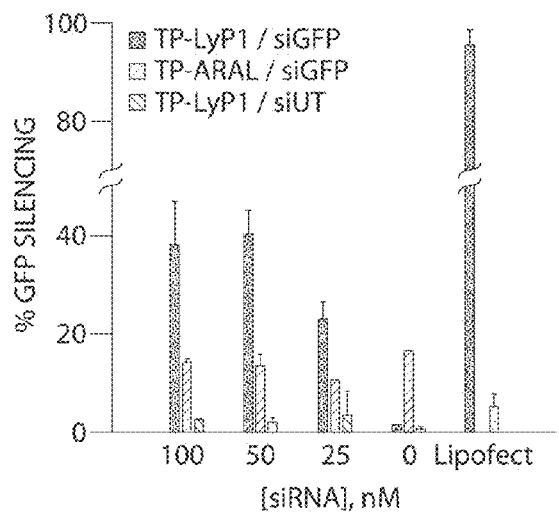
FIG. 2G shows the normalized siRNA knockdown of GFP by TP-LyP1 carrying siRNA against GFP (black bars), siRNA against an irrelevant sequence (siUT, dashed bars), or by TP-ARAL carrying GFP siRNA (gray bars). Mean values were normalized to percent of untreated control. Error bars indicate±s.e.m.
Figure 2H:
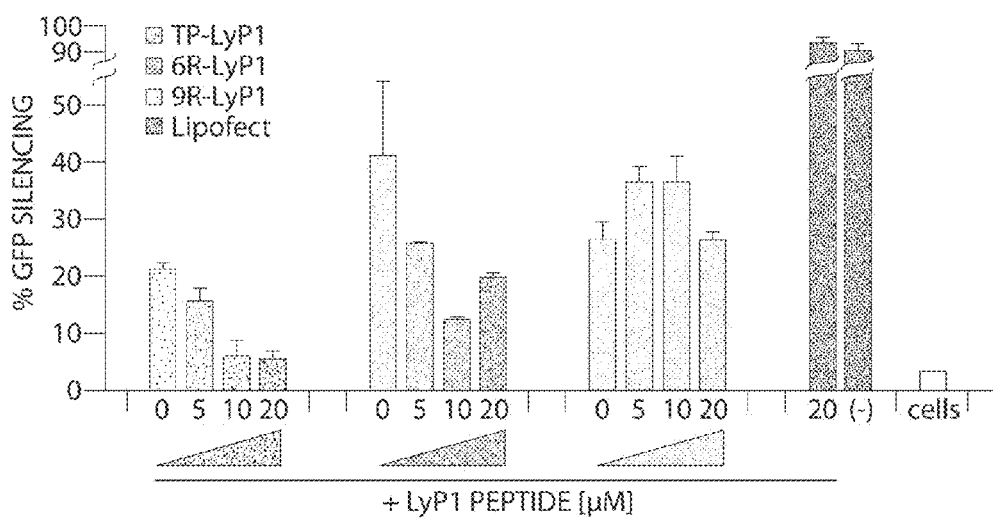
In FIG. 2H GFP silencing was re-examined in HeLa cells treated with siRNA to delivered using three different tandem peptide candidates: TP-LyP1, 6R-LyP1, and 9R-LyP1, in the presence of free LyP-1 peptide (5 to 20 μM). Transfection by lipofectamine (black) was used as a positive control.
Figure 2I:
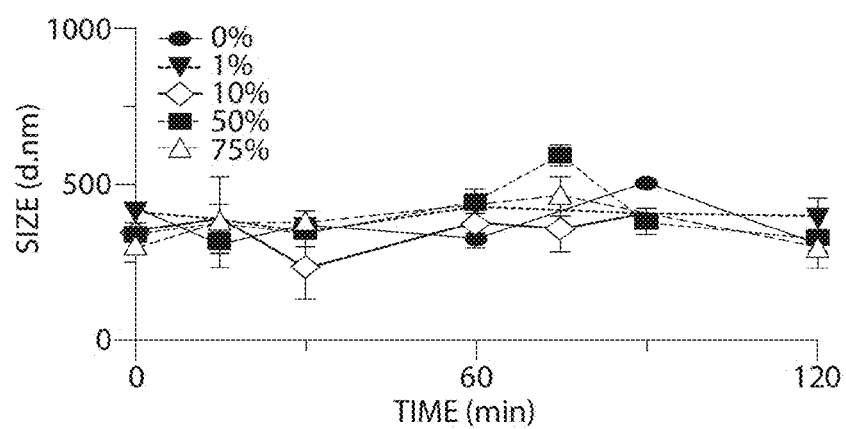
FIG. 2I shows dynamic light scattering to measure the size of nanocomplexes in various concentrations of murine serum at 37 C over time.
Figure 2J:
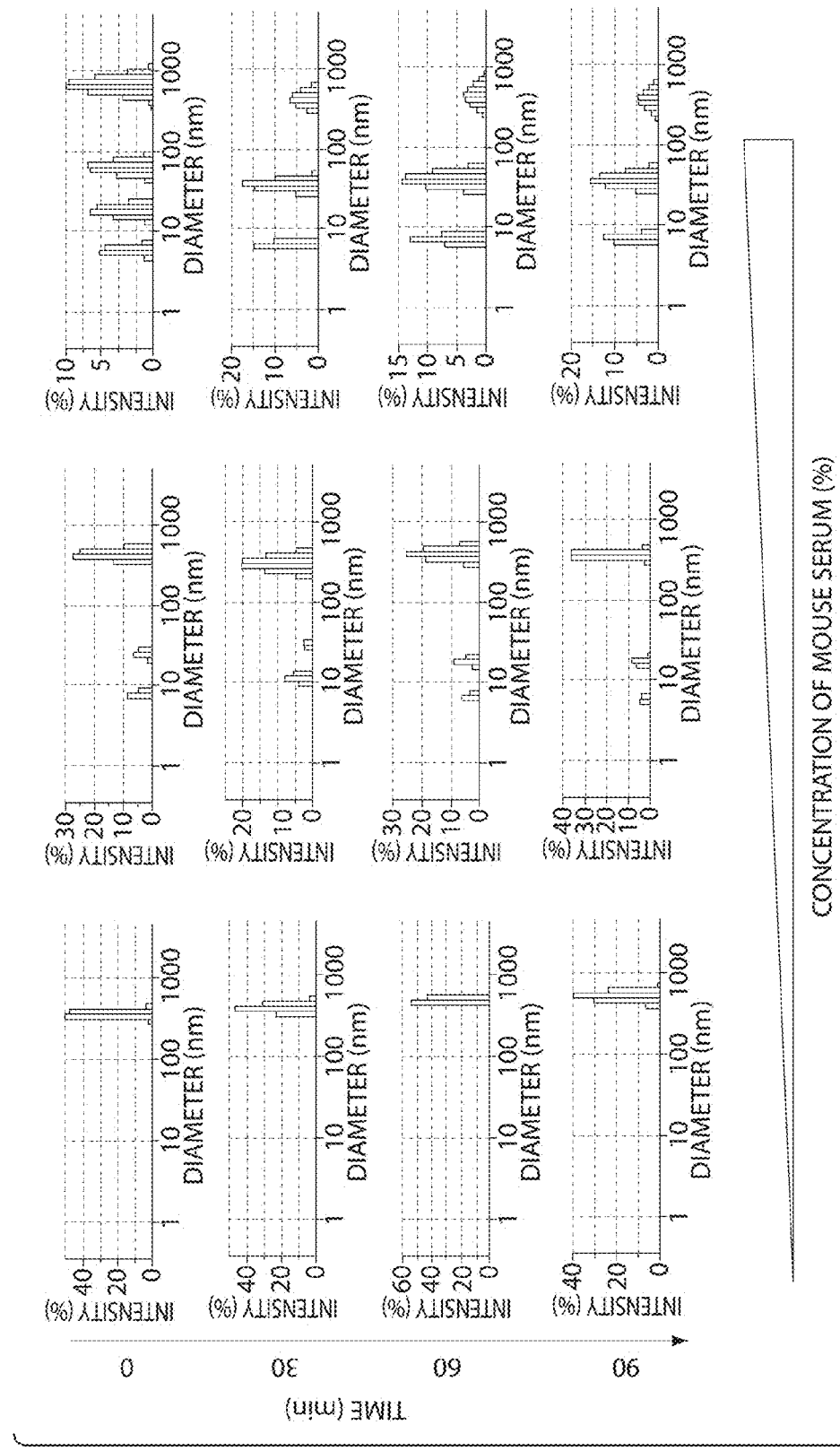
FIG. 2J shows size histograms of data from 2I.

It is suspected that the excess of free peptide required for inhibition is due to the presence of multiple copies of LyP-1 on each tandem peptide/siRNA complex, thereby improving avidity through polyvalent binding [Montet, X., Funovics, M., Montet-Abou, K., Weissleder, R. & Josephson, L. Multivalent effects of RGD peptides obtained by nanoparticle display. *J Med Chem* 49, 6087-6093, (2006)]. Addition of a control peptide had no effect on GFP knockdown. In contrast, LyP-1 did not inhibit functional siGFP delivery by 9R-LyP1, suggesting this tandem carrier did not transduce in a p32-specific manner. This is likely due to the excess number of cationic Arginine's in the cell penetrating domain that could have interfered with the targeting specificity of the homing domain. Controls showed that an unrelated siRNA did not affect GFP expression (FIGS. 2F and 2G), the untargeted tandem peptide (TP-ARAL) was unable to transduce HeLa cells (FIGS. 2F and 2G), and the addition of free LyP-1 or control peptide did not interfere with lipofectamine delivery, which is not p32 receptor-specific (FIG. 2F).

Taken together, these results illustrate that tandem peptides 6R- and TP-LyP1 enable p32-specific and efficient delivery of siRNA in vitro.

Example 5

Figure 3A:
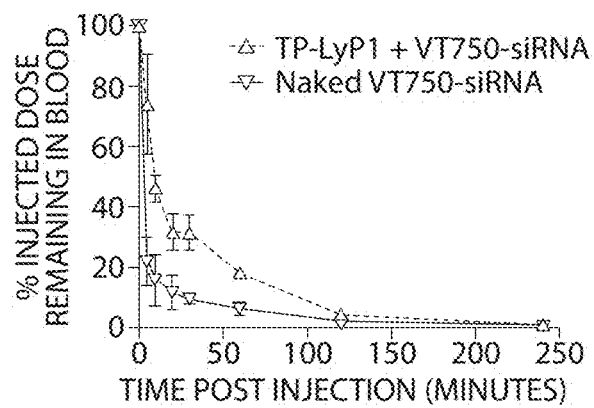
FIG. 3A demonstrates that peptide-bound siRNA has greater circulation time in vivo compared with naked siRNA upon intravenous administration in mice. Error bars indicate s.d. (n=3)
Figure 3B:
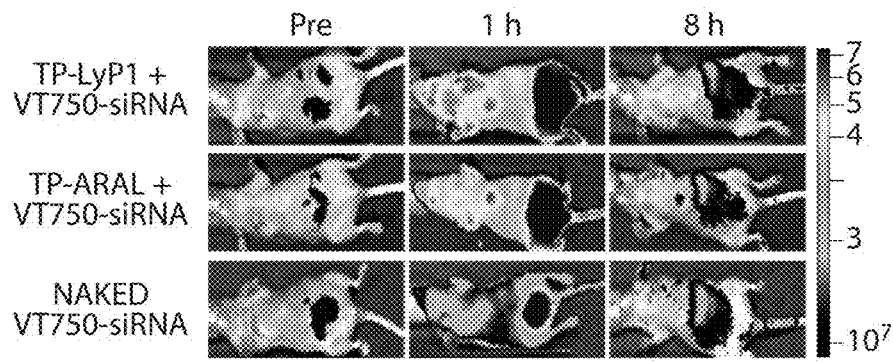
FIG. 3B shows whole-animal live imaging at multiple time points after intravenous administration of near-infrared fluorophore (VivoTag-750) labeled siRNA bound to either TP-LyP1 or TP-ARAL, or naked siRNA (5 nmols). Arrows indicate bladder uptake.
Figure 3C:
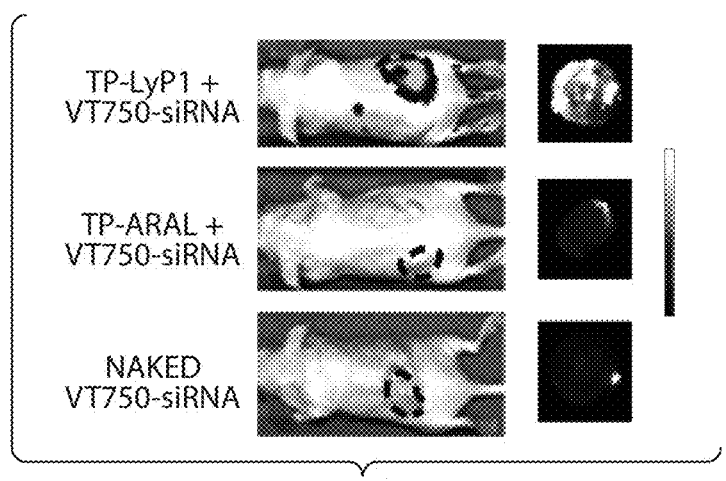
FIG. 3C shows representative fluorescence images of mice bearing bilateral MDA-MB-435 tumor xenografts (left) and tumor explants (right) after intravenous injection of VivoTag-750-labeled siRNA complexed to targeted tandem peptide or untargeted control peptide, or naked siRNA (5 nmols fluorophore per mouse). Note strong fluorescence signal is observed only in the mice that received TP-LyP1/siRNA, indicating significant homing and accumulation of the targeted peptide/siRNA.
Figure 3D:
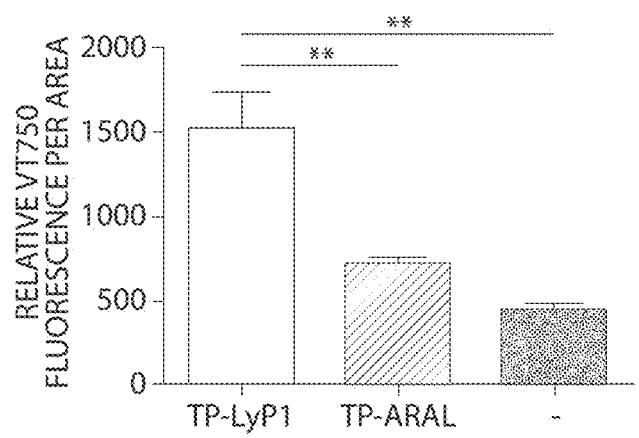
FIG. 3D shows fluorescence intensity from VivoTag-750 labeled siRNA in tumor explants from c. Error bars indicate s.d. (n=3); asterisks, P=0.0093. The tissues were collected from the mice 8 h after injection; fluorescence images use 800 nm channel on Li-COR.
Figure 3E:
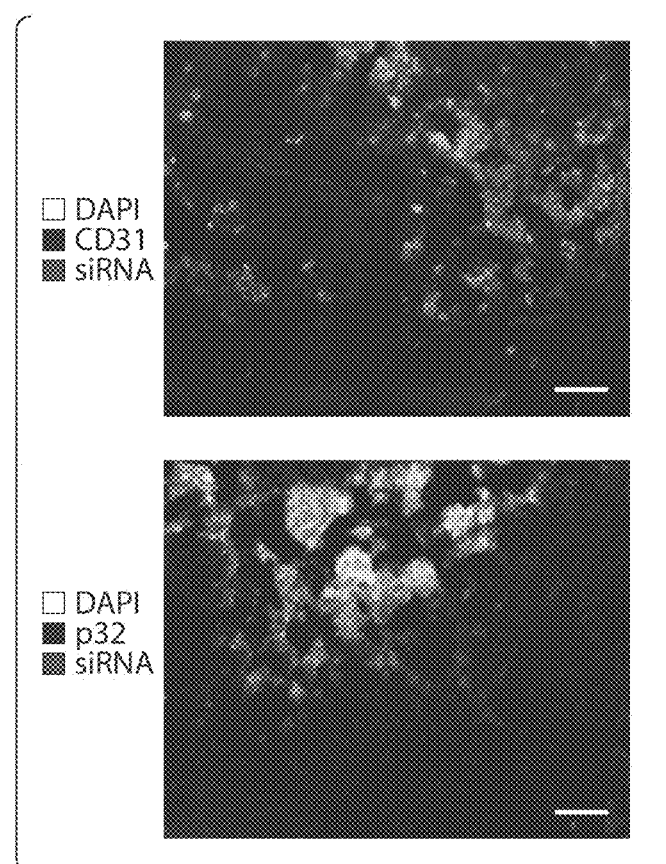
FIG. 3E shows the Histological analysis of siRNA distribution in MDA-MB-435 tumor sections (VivoTag-750-labeled siRNA, CD31 (top) and p32 (bottom) DAPI counterstain). Scale bar is 50 μm.

The behavior (e.g., in vivo homing) of tandem peptide/siRNA complexes was evaluated after systemic administration in mice to target specific tumor cells. Near-infrared fluorochrome-labeled (VivoTag 750) siRNAs were mixed with TP-LyP1, while siRNA mixed with untargeted tandem peptides and naked siRNAs were used as negative controls. After i.v administration to immunodeficient mice bearing subcutaneous MDA-MB-435 tumor xenografts, a significant fraction of naked siRNAs was rapidly removed via renal clearance as indicated by bladder accumulation of fluorescent siRNA, likely owing to their small size (FIGS. 3A and 3B). By contrast, siRNAs complexed to tandem peptides were renally cleared more slowly over time presumably due to gradual disintegration of the nanocomplexes in circulation. After clearance from circulation (8 h), the entire mouse and individual explanted organs and tumors were fluorescently imaged (FIGS. 3C and 3D). Biodistribution studies are consistent with whole-body fluorescence imaging data (FIGS. 11A-E). In some cases, over three-fold increase in the tumor fluorescence of targeted TPNs compared to peptides with control homing domains was observed (FIGS. 11 and 12E). Therefore, a marked increase in the tumor homing of actively targeted siRNA was found, with over three-fold increase in accumulation above untargeted nanocomplexes, and three-fold improvement compared to naked siRNA (FIG. 3D). Histologically, accumulation of near-infrared fluorescent dye was observed in the interstitium of dissected tumors only in mice that received TP-LyP1 targeted siRNA. Vascular staining with anti-CD31 antibodies and tumor cell staining with anti-p32 antibodies (FIG. 3E) showed that siRNA targeted by TP-LyP1 have extravasated from the vasculature, penetrated into the interstitial space of the tumor, and bound to p32-expressing tumor cells. This pattern of distribution was consistent with previously reported LyP-1 peptide and LyP-1 targeted nanoparticle homing [Laakkonen, P., Porkka, K., Hoffman, J. A. & Ruoslahti, E. A tumor-homing peptide with a targeting specificity related to lymphatic vessels. *Nat Med* 8, 751-755, (2002); and Park, J. H. et al. Cooperative nanomaterial system to sensitize, target, and treat tumors. *Proc Natl Acad Sci USA* 107, 981-986, (2010)]. Untargeted or naked siRNAs were not delivered into the tumor (data not shown). Similar results in p32-specific tumor targeting were also obtained with 6R-LyP1 targeted siRNA and by injecting TP-LyP1/siRNA complexes intraperitoneally, suggesting suitability for multiple routes of administration for clinical use (FIG. 12).

Histological characterization on the time course of penetration showed an initial intravascular distribution and subsequent extravasation into the interstitium of OVCAR-8 tumors, likely due to the penetration motif (R/KXXR/K) ((SEQ ID NO: 4) (FIG. 12F). The fraction of targeted nanocomplexes that were sequestered beyond the intravascular space was significantly higher than that of untargeted controls (FIG. 12G). TPNs also co-localized with p32-positive tumor cells (FIG. 11). This pattern of distribution was consistent with previously reported LyP1 peptide, Lyp1 phage and LyP1 targeted nanoparticle homing No fluorescence signal was detected from tumor sections for the untargeted or naked siRNAs (data not shown). Similar results in tumor targeting were also obtained by intraperitoneal injections and with 6R-LyP1/siRNA (FIG. 12).

Example 6

Figure 3F:
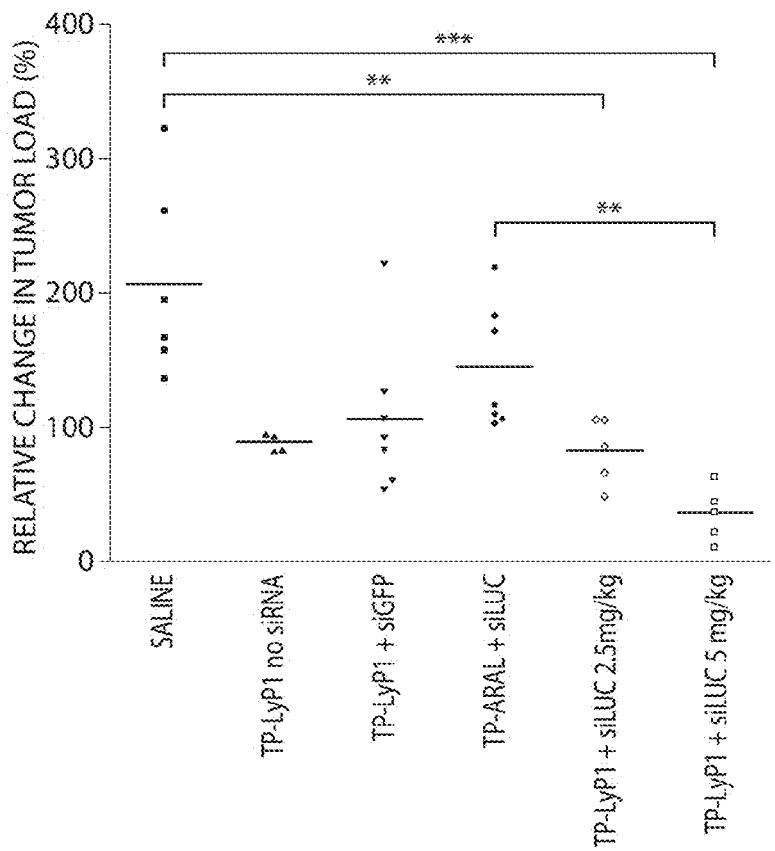
In FIG. 3F mice bearing disseminated intraperitoneal luciferase expressing MDA-MB-435 tumors were injected intraperitoneally with targeted tandem peptide complexed to siRNA against luciferase. The amount of gene silencing was measured by optical bioluminescence imaging 48 h after injection. Statistical analyses were performed with ANOVA and Bonferroni post-test for pair-wise comparisons. Horizontal lines, mean values. (n=4-6); (P<0.01), *(P<0.001)
Figure 3G:
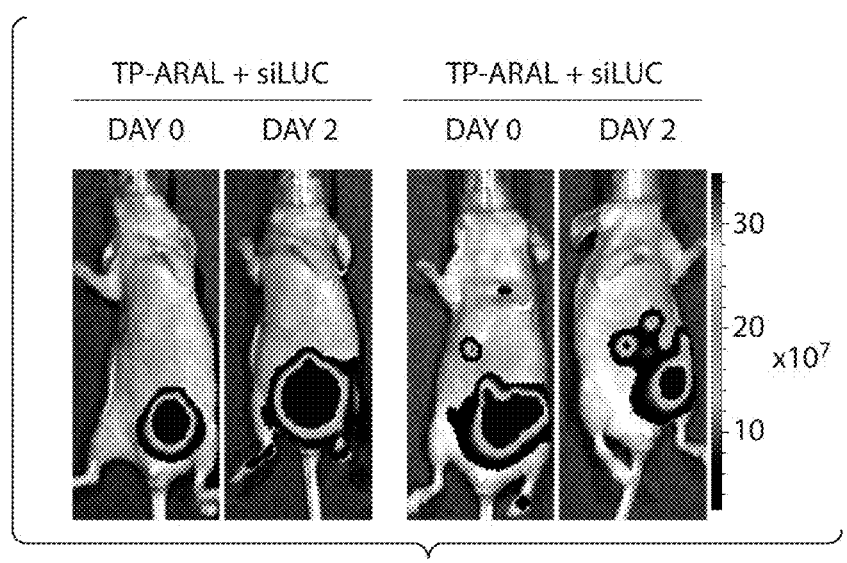
FIG. 3G, shows representative bioluminescence images of luciferase activity of mice from before and after siRNA treatment.

To test tumor cell-specific gene silencing, an intraperitoneal MDA-MB-435 xenograft mouse model was established. Total metastatic tumor burden was assessed via bioluminescent imaging of luciferase expression. Cohorts of mice with established tumors were treated with luciferase siRNA bound to TP-LyP1 (5 mg/kg). A significant decrease in tumor bioluminescence was observed 2 days after treatment with TP-LyP1 complexed to siRNA against luciferase (5 mg/kg) whereas all other tumors, including those treated with TP-ARAL/luciferase siRNA, did not show any decrease in tumor load (FIGS. 3F and 3G). The gene silencing effect gradually decreased over a 4-day period (FIG. 13), which agrees with reported duration of RNAi after intraperitoneal administration.

Example 7

Figure 4A:
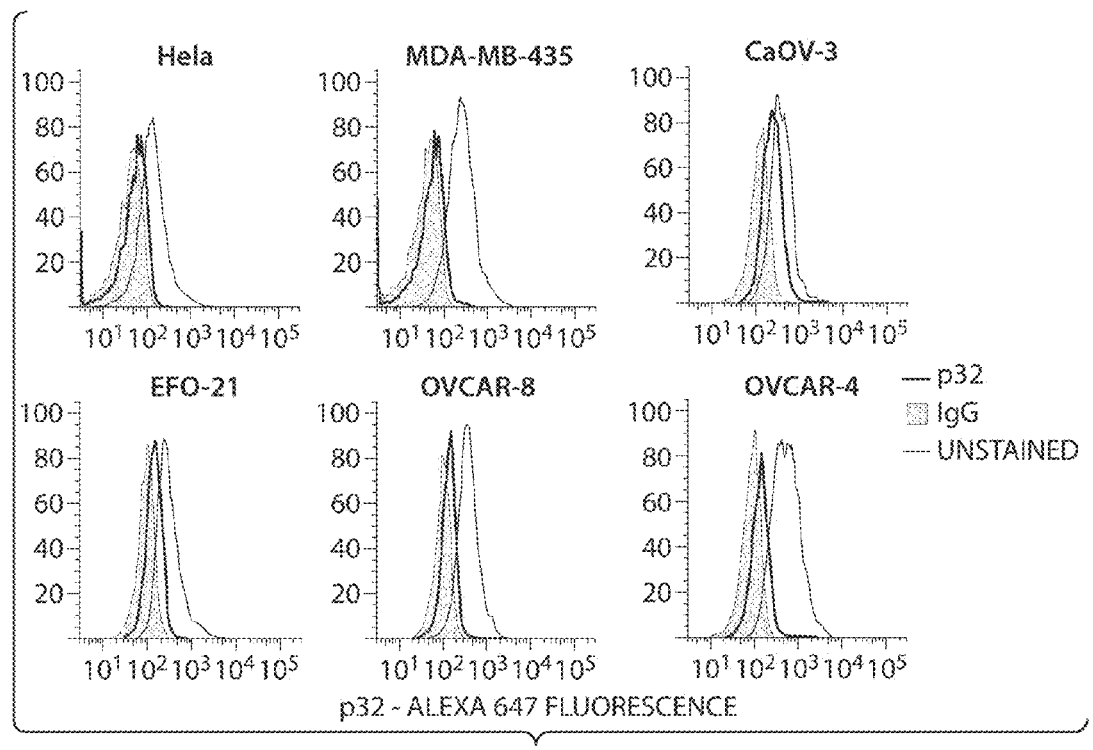
FIG. 4A shows flow cytometry analysis of p32 cell surface receptor levels in human tumor cell lines using polyclonal anti-full-length/$NH_2$-terminal p32 or IgG isotype control (Error bars indicate s.d.)
Figure 4B:
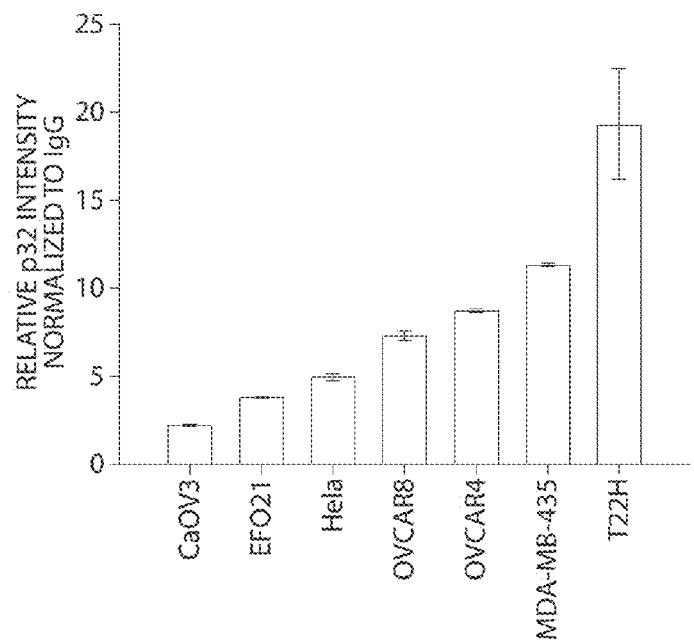
FIG. 4B shows the relative p32 intensity in six (6) different human cancer cell lines derived from: ovarian cancer (CaOV3, EFO21, OVCAR-8, and OVCAR-4), cervical cancer (HeLa), breast cancer (MDA-MB-435), and a mouse ovarian cancer cell line (T22H)
Figure 4C:
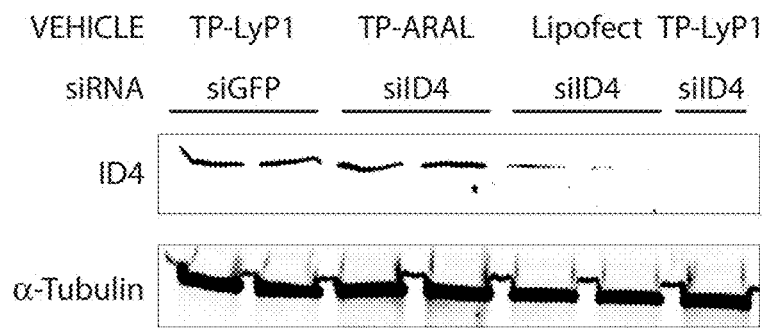
FIG. 4C is western blot demonstrating knockdown of ID4 in OVCAR-8 ovarian cancer cells treated with TP-LyP1/siRNA nanocomplexes. Lipofectamine was used as a positive control. Untargeted peptide or irrelevant siRNA were used as negative controls.
Figure 4D:
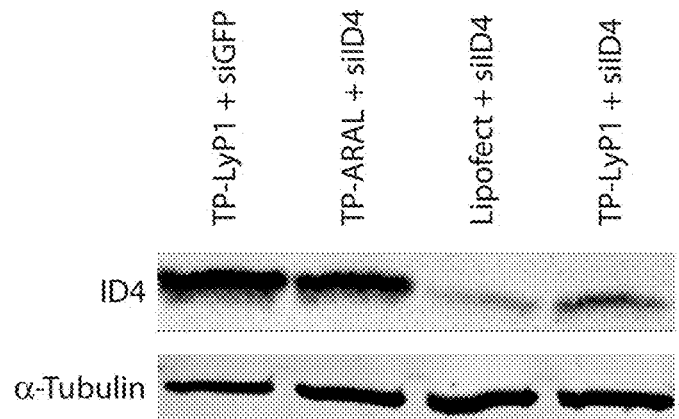
FIG. 4D, ID4 shows the protein levels in OVCAR-4 cells treated with TP-LyP1/siRNA complexes.
Figure 4E:
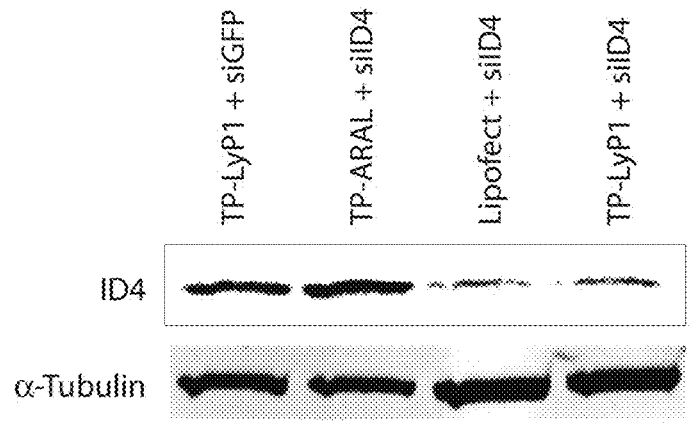
FIG. 4E is a western blot analysis of knockdown of ID4 in EFO-21 ovarian cancer cells.
Figure 4F:
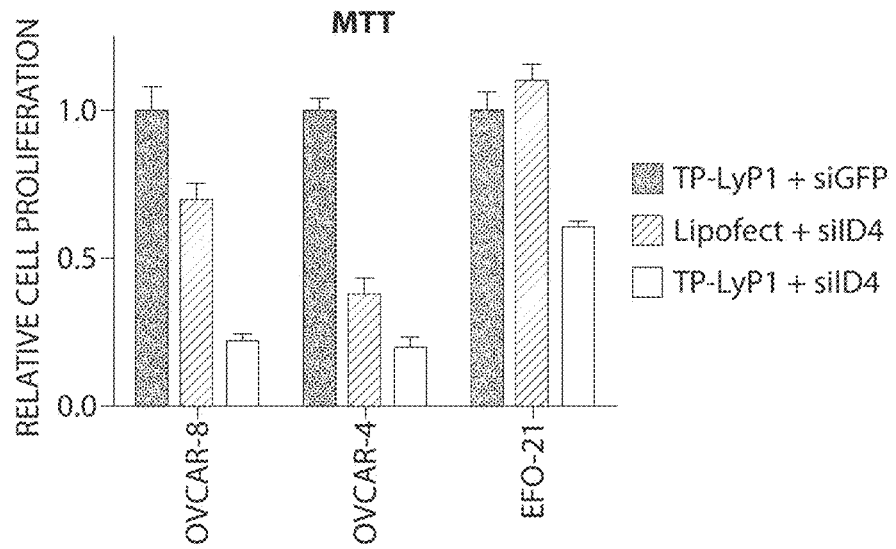
FIG. 4F shows a MTT (3-(4,5-Dimethylthiazol-2-yl)-2,5-diphenyltetrazolium bromide) assay showing decreased mitocondrial reductase activity in all 3 ovarian cancer cell lines treated with TP-LyP1/ID4 siRNA (white bars) compared to treatment with GFP siRNA (black bars) or lipofectamine/siID4 (gray bars)
Figure 4G:
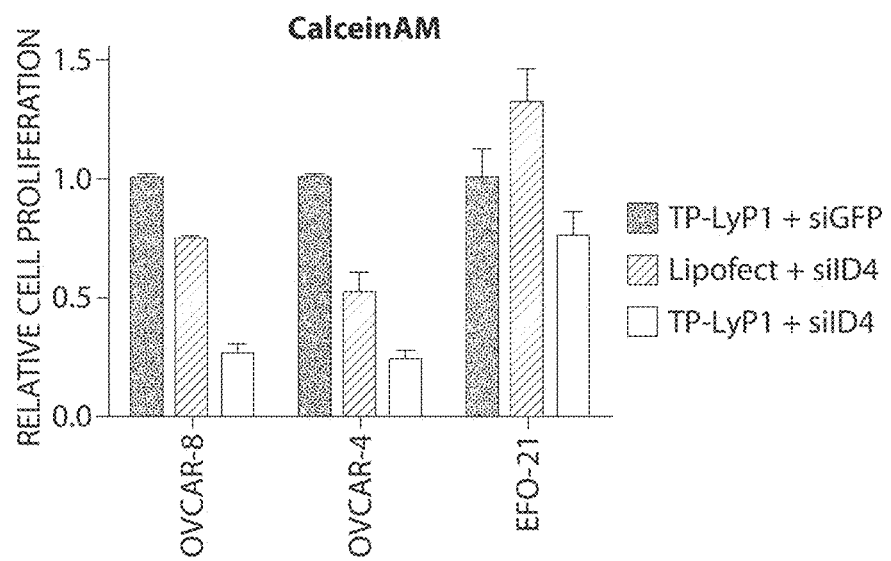
FIG. 4G shows cytotoxicity measured by calcein-AM assay demonstrating reduced intracellular esterase activity in TP-LyP1/siID4 treated cells.
Figure 4H:
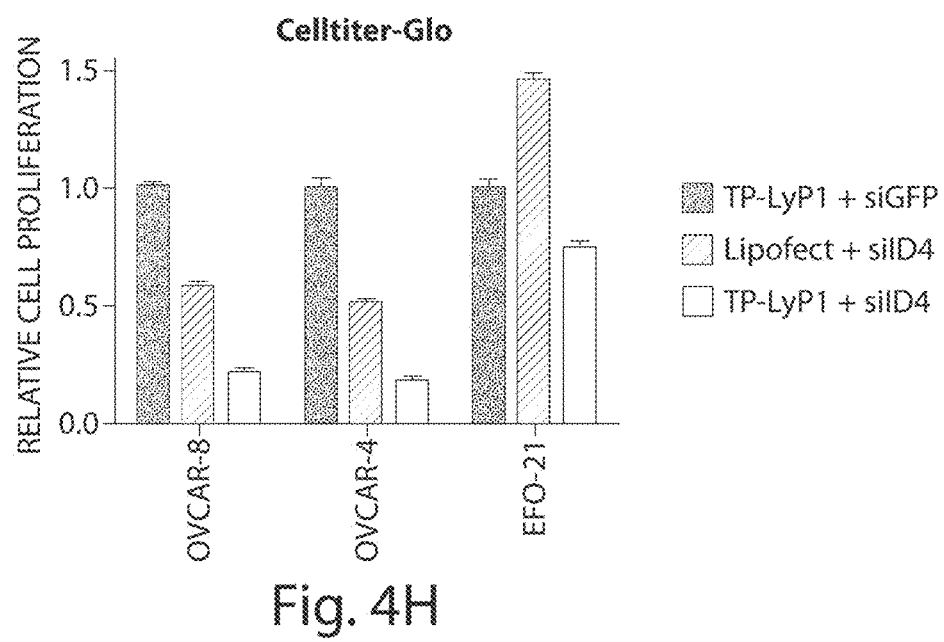
FIG. 4H shows Celltiter-Glo assay measuring cellular ATP content. Error bars indicate s.d.

Ovarian cancer is the most lethal gynaecologic malignancy in the United States and five-year survival for patients with advanced disease is poor [Jemal, A. et al. Cancer statistics, 2009. *CA Cancer J Clin* 59, 225-249, (2009); and Polverino, G. et al. Survival and prognostic factors of women with advanced ovarian cancer and complete response after a carboplatin-paclitaxel chemotherapy. *Gynecol Oncol* 99, 343-347, (2005)]. Standard treatments suffer from drawbacks including acute toxicity and emergence of drug resistance [Memarzadeh, S. & Berek, J. S. Advances in the management of epithelial ovarian cancer. *J Reprod Med* 46, 621-629; discussion 629-630, (2001)]. In some embodiments, novel therapies such as delivery of siRNA against essential ovarian oncogenes may be beneficial. The in vitro targeted siRNA delivery against ID4, a putative ovarian cancer-specific oncogene, was evaluated. A collection of ovarian cancer cell lines that harbour 6p amplifications and whose proliferation depend on ID4 signalling was surveyed for their p32 status (FIGS. 4A-B and 14). Of 4 cell lines examined, p32 was expressed on the surface in three (OVCAR-8, OVCAR-4, and EFO-21). To determine whether cell proliferation was perturbed when ID4 was depleted, the response to p32-targeted, tandem peptide delivery of siRNA against ID4 was evaluated in these cells (FIGS. 4C-E). Cells treated with TP-LyP1/siID4 showed significant reduction in ID4 levels (up to 90% in OVCAR-8, and up to 80% in OVCAR-4 and EFO-21), whereas cells treated with TP-ARAL/siID4 did not, suggesting knockdown is p32-specific (FIG. 15). Suppression of ID4 induced substantial cell toxicity in all three cell lines. This toxicity was quantified by a reduction in mitochondrial reductase activity (FIG. 4F), intracellular esterase activity (FIG. 4G), and intracellular ATP content (FIG. 4H). The sensitivity of OVCAR-8 cells to p32-targeted ID4 RNAi is likely secondary to induction of apoptosis, as increased Annexin-V staining was observed in TP-LyP1/siID4 treated cells by FACS analysis. The significant reduction of ID4 protein in cells treated with TP-LyP1/siID4, led to substantial reduction in cell viability and increased apoptotic cell death (FIGS. 15E and 15F). In contrast, the level of cells entering S-phase was unchanged between treatment and control groups (FIG. 15C).

Example 8

After ID4 signalling was shown to be required for proliferation of human ovarian cancer cells that also express p32, the effect of targeted silencing of ID4 on tumor to progression was evaluated in two different mouse models.

An intraperitoneal OVCAR-8 xenograft mouse model was evaluated. Orthotopic OVCAR-8 tumors were established and metastatic dissemination was confirmed 3 weeks later. TPNs were injected i.p. every 3 d. (FIG. 5K). Regression was observed for tumors that received TP-LyP1/siID4, whereas control cohorts continued to grow uninhibited and develop hemorrhagic ascites, which may have attenuated tumor bioluminescence resulting in an underestimation of tumor burden (FIGS. 5A-B). After 40 d, macroscopic examination revealed disseminated tumors in control cohorts but no visible tumor lesions in 4 out of 5 TP-LyP1/siID4 treated mice. Histological analysis of the remnant tumor showed significant reduction in ID4 levels and increased apoptosis in the tumor parenchyma (FIGS. 5C-E). Interestingly, the level of p32 in the siID4 treated tumors was higher than that in the controls (FIG. 16). Since the surface expression of p32 is known to increase under stress, this may represent a pathway for enhanced uptake of targeted nanocomplexes upon repeated exposures. TP-LyP1/siID4 also extended the tumor-free median survival (FIG. 5F).

In more detail, after tumor establishment as verified by increase in whole-animal luciferase activity, mice were injected i.p. with ID4 targeted siRNA complexed with TP-LyP1 (5 mg/kg). Control animal groups received saline, ID4 siRNA bound to untargeted TP-ARAL, or TP-LyP1 complexed to irrelevant GFP siRNA (FIG. 5A). The treatment was repeated twice weekly for two weeks, after which the dose is tapered down to once weekly. Knockdown of ID4 in p32-expressing tumor cells in vivo significantly suppressed tumor progression and improved overall survival compared to controls. Within 3 weeks after the initiation of treatment, all the TP-LyP1-targeted, siID4 treated tumors showed little progression from baseline, whereas all other groups, including those received the same tandem peptide but complexed to a scrambled siRNA, continued to grow and metastasize uninhibited (FIG. 5B) Immuno-staining of tumor sections harvested on day 40 for ID4 protein showed significant reduction in ID4 levels in the treated mice but not in any of the controls (FIGS. 5C and 5E). The levels of p32 protein were not significantly altered (FIGS. 5C and 16). TUNEL staining of tumor sections for apoptosis showed that a majority of tumor cells in the treated mice were apoptotic compared to negligible amounts in the control mice (FIG. 5D). By 40 days, 4 out of 5 TP-LyP1/siID4 treated mice showed complete tumor regression, as no sign of tumor burden was detectable by in vivo luciferase imaging (FIG. 5F). In contrast, mice in the control groups developed ascites by week 4 due to large tumor loads and had to be euthanized. This significant improvement in survival suggested that tandem peptide mediated functional delivery of ID4 siRNA can suppress the growth and metastasis of ovarian tumors.

Separately, it was observed that intravenous injections of TP-LyP1/siID4 nanocomplexes into subcutaneous OVCAR-4 tumors every 3 d resulted in 80-90% reduction in tumor burden and significantly extended survival. By contrast, nanocomplexes carrying an unrelated siRNA or TP-LyP1 carrier alone had no effect (FIGS. 5G-J). The versatility of TPNs for direct target comparison was demonstrated by treating tumors with nanocomplexes carrying siRNA against claudin-3 (CLDN3), a recently reported potential ovarian siRNA target. TP-LyP1/siCLDN3 injections showed significant but less dramatic growth suppression compared to TP-LyP1/siID4. More importantly, tumor growth remained halted in siID4-treated cohorts for 30 d after the cessation of siRNA treatment.

Example 9

Therapeutic effects of RNAi may be confounded by non-sequence specific innate immune responses mediated by toll-like receptors. However, the tandem peptide/siRNA nanocomplexes were found to be non-immunostimulatory. To confirm that the therapeutic effects are not attributed to non-specific activation of innate immune responses, serum levels were measured for interferon alpha (IFN-α), TNF-α, and IL-6 in immunocompetent mice after administration of TP-LyP1/siID4. These cytokines were not induced in siID4 treated animals compared to mice that received a known immunostimulatory siRNA complexed to TP-LyP1 [Judge, A. D. et al. Sequence-dependent stimulation of the mammalian innate immune response by synthetic siRNA. *Nat Biotechnol* 23, 457-462, (2005)], suggesting the therapeutic benefit was indeed specific to RNAi (FIG. 17). Treatment did not negatively affect animal weight, and no macroscopic or histological signs of organ toxicity were observed (e.g., after treatment with TP-LyP1/siID4 for 40 days as shown in FIG. 18).

Example 10

Lyp-1 was replaced with iRGD and was found to penetrate tumor parenchyma in a to time-dependent manner (data not shown).

REFERENCES

1 Jain, R. K. Delivery of molecular and cellular medicine to solid tumors. *J Control Release* 53, 49-67, (1998).
2 Jain, R. K. Delivery of molecular and cellular medicine to solid tumors. *Adv Drug Deliv Rev* 46, 149-168, (2001).
3 Ruoslahti, E. Drug targeting to specific vascular sites. *Drug Discov Today* 7, 1138-1143, (2002).
4 Ruoslahti, E. Specialization of tumour vasculature. *Nat Rev Cancer* 2, 83-90, (2002).
5 Jain, R. K. Delivery of molecular and cellular medicine to solid tumors. *J Control Release* 53, 49-67, (1998); Satchi-Fainaro, R. et al. Targeting angiogenesis with a conjugate of HPMA copolymer and TNP-470. *Nat Med* 10, 255-261, (2004).
6 Whitehead, K. A., Langer, R. & Anderson, D. G. Knocking down barriers: advances in siRNA delivery. *Nat Rev Drug Discov* 8, 129-138, (2009).
7 Akerman, M. E., Chan, W. C., Laakkonen, P., Bhatia, S. N. & Ruoslahti, E. Nanocrystal targeting in vivo. *Proc Natl Acad Sci USA* 99, 12617-12621, (2002).

8 Pasqualini, R. & Ruoslahti, E. Organ targeting in vivo using phage display peptide libraries. *Nature* 380, 364-366, (1996).
9 Comprehensive genomic characterization defines human glioblastoma genes and core pathways. *Nature* 455, 1061-1068, (2008).
10 Elbashir, S. M. et al. Duplexes of 21-nucleotide RNAs mediate RNA interference in cultured mammalian cells. *Nature* 411, 494-498, (2001).
11 Fire, A. et al. Potent and specific genetic interference by double-stranded RNA in *Caenorhabditis elegans*. *Nature* 391, 806-811, (1998).
12 Hopkins, A. L. & Groom, C. R. The druggable genome. *Nat Rev Drug Discov* 1, 727-730, (2002).
13 Soutschek, J. et al. Therapeutic silencing of an endogenous gene by systemic administration of modified siRNAs. *Nature* 432, 173-178, (2004).
14 Wolfrum, C. et al. Mechanisms and optimization of in vivo delivery of lipophilic siRNAs. *Nat Biotechnol* 25, 1149-1157, (2007).
15 Akinc, A. et al. A combinatorial library of lipid-like materials for delivery of RNAi therapeutics. *Nat Biotechnol* 26, 561-569, (2008).
16 Davis, M. E. et al. Evidence of RNAi in humans from systemically administered siRNA via targeted nanoparticles. *Nature,* 464, 1067-1070, (2010).
17 Eguchi, A. et al. Efficient siRNA delivery into primary cells by a peptide transduction domain-dsRNA binding domain fusion protein. *Nat Biotechnol* 27, 567-571, (2009).
18 Kumar, P. et al. T cell-specific siRNA delivery suppresses HIV-1 infection in humanized mice. *Cell* 134, 577-586, (2008).
19 Kumar, P. et al. Transvascular delivery of small interfering RNA to the central nervous system. *Nature* 448, 39-43, (2007).
20 Karnoub, A. E. et al. Mesenchymal stem cells within tumour stroma promote breast cancer metastasis. *Nature* 449, 557-563, (2007).
21 Laakkonen, P., Porkka, K., Hoffman, J. A. & Ruoslahti, E. A tumor-homing peptide with a targeting specificity related to lymphatic vessels. *Nat Med* 8, 751-755, (2002).
22 Fogal, V., Zhang, L., Krajewski, S. & Ruoslahti, E. Mitochondrial/cell-surface protein p32/gC1qR as a molecular target in tumor cells and tumor stroma. *Cancer Res* 68, 7210-7218, (2008).
23 Veldhoen, S., Laufer, S. D., Trampe, A. & Restle, T. Cellular delivery of small interfering RNA by a non-covalently attached cell-penetrating peptide: quantitative analysis of uptake and biological effect. *Nucleic Acids Res* 34, 6561-6573, (2006).
24 Montet, X., Funovics, M., Montet-Abou, K., Weissleder, R. & Josephson, L. Multivalent effects of RGD peptides obtained by nanoparticle display. *J Med Chem* 49, 6087-6093, (2006).
25 Park, J. H. et al. Cooperative nanomaterial system to sensitize, target, and treat tumors. *Proc Natl Acad Sci USA* 107, 981-986, (2010).
26 Jemal, A. et al. Cancer statistics, 2009. *CA Cancer J Clin* 59, 225-249, (2009).
27 Polverino, G. et al. Survival and prognostic factors of women with advanced ovarian cancer and complete response after a carboplatin-paclitaxel chemotherapy. *Gynecol Oncol* 99, 343-347, (2005).
28 Memarzadeh, S. & Berek, J. S. Advances in the management of epithelial ovarian cancer. *J Reprod Med* 46, 621-629; discussion 629-630, (2001).
29 Judge, A. D. et al. Sequence-dependent stimulation of the mammalian innate immune response by synthetic siRNA. *Nat Biotechnol* 23, 457-462, (2005).
30 Fogal, V. et al. Mitochondrial p32 protein is a critical regulator of tumor metabolism via maintenance of oxidative phosphorylation. *Mol Cell Biol* 30, 1303-1318, (2010).
31 Henke, E. et al. Peptide-conjugated antisense oligonucleotides for targeted inhibition of a transcriptional regulator in vivo. Nat Biotechnol 26, 91-100, (2008).
32 Song, E. et al. Antibody mediated in vivo delivery of small interfering RNAs via cell-surface receptors. Nat Biotechnol 23, 709-717, (2005).
33 Sugahara, K. N. et al. Tissue-penetrating delivery of compounds and nanoparticles into tumors. Cancer Cell 16, 510-520, (2009).
34 Sugahara, K. N. et al. Coadministration of a Tumor-Penetrating Peptide Enhances the Efficacy of Cancer Drugs. Science, (2010).
35 Teesalu, T., Sugahara, K. N., Kotamraju, V. R. & Ruoslahti, E. C-end rule peptides mediate neuropilin-1-dependent cell, vascular, and tissue penetration. Proc Natl Acad Sci USA 106, 16157-16162, (2009).
36 Wadia, J. S., Stan, R. V. & Dowdy, S. F. Transducible TAT-HA fusogenic peptide enhances escape of TAT-fusion proteins after lipid raft macropinocytosis. Nat Med 10, 310-315, (2004).
37 Luo, B. et al. Highly parallel identification of essential genes in cancer cells. Proc. Natl Acad. Sci. USA 105, 20380-20385, (2008).
38 TCGA-Network. In press.
39 Sieben, N. L. et al. In ovarian neoplasms, BRAF, but not KRAS, mutations are restricted to low-grade serous tumours. J Pathol 202, 336-340, (2004).
40 Singer, G. et al. Mutations in BRAF and KRAS characterize the development of low-grade ovarian serous carcinoma. J Natl Cancer Inst 95, 484-486, (2003).
41 Singer, G., Kurman, R. J., Chang, H. W., Cho, S. K. & Shih Ie, M. Diverse tumorigenic pathways in ovarian serous carcinoma. Am J Pathol 160, 1223-1228, (2002).
42 Sheng, Q. et al. An activated ErbB3/NRG1 autocrine loop supports in vivo proliferation in ovarian cancer cells. Cancer Cell 17, 298-310, (2010).
43 Lin, H. K. et al. Skp2 targeting suppresses tumorigenesis by Arf-p53-independent cellular senescence. Nature 464, 374-379, (2010).
44 Chen, Y. B., Jiang, C. T., Zhang, G. Q., Wang, J. S. & Pang, D. Increased expression of hyaluronic acid binding protein 1 is correlated with poor prognosis in patients with breast cancer. J Surg Oncol 100, 382-386, (2009).
45 Rubinstein, D. B. et al. Receptor for the globular heads of C1q (gC1q-R, p33, hyaluronan-binding protein) is preferentially expressed by adenocarcinoma cells. Int J Cancer 110, 741-750, (2004).
46 Maurer-Stroh, S. & Eisenhaber, F. Myristoylation of viral and bacterial proteins. Trends Microbiol 12, 178-185, (2004).
47 Karmali, P. P. et al. Targeting of albumin-embedded paclitaxel nanoparticles to tumors. Nanomedicine 5, 73-82, (2009).
48 Laakkonen, P. et al. Antitumor activity of a homing peptide that targets tumor lymphatics and tumor cells. Proc Natl Acad Sci USA 101, 9381-9386, (2004).
49 Liu, J. et al. A genetically defined model for human ovarian cancer. Cancer Res. 64, 1655-1663, (2004).
50 Hamad, N. M. et al. Distinct requirements for Ras oncogenesis in human versus mouse cells. Genes Dev 16, 2045-2057, (2002).

51 Rangarajan, A., Hong, S. J., Gifford, A. & Weinberg, R. A. Species- and cell type-specific requirements for cellular transformation. Cancer Cell 6, 171-183, (2004).
52 Boehm, J. S., Hession, M. T., Bulmer, S. E. & Hahn, W. C. Transformation of human and murine fibroblasts without viral oncoproteins. Mol Cell Biol 25, 6464-6474, (2005).
53 Boehm, J. S. et al. Integrative genomic approaches identify IKBKE as a breast cancer oncogene. Cell 129, 1065-1079, (2007).
54 de Candia, P., Benera, R. & Solit, D. B. A role for Id proteins in mammary gland physiology and tumorigenesis. Adv Cancer Res 92, 81-94, (2004).
55 Desprez, P. Y., Sumida, T. & Coppe, J. P. Helix-loop-helix proteins in mammary gland development and breast cancer. J Mammary Gland Biol Neoplasia 8, 225-239, (2003).
56 Iavarone, A. & Lasorella, A. Id proteins in neural cancer. Cancer Lett 204, 189-196, (2004).
57 Norton, J. D. ID helix-loop-helix proteins in cell growth, differentiation and tumorigenesis. J Cell Sci 113 (Pt 22), 3897-3905, (2000).
58 Perk, J., Iavarone, A. & Benezra, R. Id family of helix-loop-helix proteins in cancer. Nature Rev. Cancer 5, 603-614, (2005).
59 Sikder, H. A., Devlin, M. K., Dunlap, S., Ryu, B. & Alani, R. M. Id proteins in cell growth and tumorigenesis. Cancer Cell 3, 525-530, (2003).
60 Wu, Q. et al. Transcriptional regulation during p21WAF1/CIP1-induced apoptosis in human ovarian cancer cells. J. Biol. Chem. 277, 36329-36337, (2002).
61 Prabhu, S., Ignatova, A., Park, S. T. & Sun, X. H. Regulation of the expression of cyclin-dependent kinase inhibitor p21 by E2A and Id proteins. Mol. Cell Biol. 17, 5888-5896, (1997).
62 Ciarrocchi, A. et al. Id1 restrains p21 expression to control endothelial progenitor cell formation. PLoS One 2, e1338, (2007).
63 Hess, J. L. et al. c-Myb is an essential downstream target for homeobox-mediated transformation of hematopoietic cells. Blood 108, 297-304, (2006).
64 Cheng, W., Liu, J., Yoshida, H., Rosen, D. & Naora, H. Lineage infidelity of epithelial ovarian cancers is controlled by HOX genes that specify regional identity in the reproductive tract. Nature Med. 11, 531-537, (2005).
65 Takeda, A., Goolsby, C. & Yaseen, N. R. NUP98-HOXA9 induces long-term proliferation and blocks differentiation of primary human CD34+ hematopoietic cells. Cancer Res. 66, 6628-6637, (2006).
66 Faber, J. et al. HOXA9 is required for survival in human MLL-rearranged acute leukemias. Blood 113, 2375-2385, (2009).
67 Huang, Y. H. et al. Claudin-3 gene silencing with siRNA suppresses ovarian tumor growth and metastasis. Proc Natl Acad Sci USA 106, 3426-3430, (2009).
68 Marques, J. T. & Williams, B. R. Activation of the mammalian immune system by siRNAs. Nat Biotechnol 23, 1399-1405, (2005).
69 Bartlett, D. W., Su, H., Hildebrandt, I. J., Weber, W. A. & Davis, M E Impact of tumor-specific targeting on the biodistribution and efficacy of siRNA nanoparticles measured by multimodality in vivo imaging. Proc Natl Acad Sci USA 104, 15549-15554, (2007).
70 MacDiarmid, J. A. et al. Sequential treatment of drug-resistant tumors with targeted minicells containing siRNA or a cytotoxic drug. Nat Biotechnol 27, 643-651, (2009).
71 Muratovska, A. & Eccles, M. R. Conjugate for efficient delivery of short interfering RNA (siRNA) into mammalian cells. FEBS Lett 558, 63-68, (2004).
72 Beroukhim, R. et al. The landscape of somatic copy-number alteration across human cancers. Nature 463, 899-905, (2010).
73 Mermel, C. H., Getz, G. & Meyerson, M. Submitted.
74 Subramanian, A. et al. Gene set enrichment analysis: a knowledge-based approach for interpreting genome-wide expression profiles. Proc. Natl Acad. Sci. USA 102, 15545-15550, (2005).
75. Ruoslahti E, Bhatia S N, Sailor M J. Targeting of drugs and nanoparticles to tumors. J Cell Biol. 2010 Mar. 22; 188(6):759-68. Epub 2010 Mar. 15.

---

What is claimed is:

1. A composition comprising:
   a polypeptide comprising a first homing domain and a second cell-penetrating domain, wherein the second cell-penetrating domain is N-terminal to the first homing domain and the N-terminus of the polypeptide is modified with a lipophilic group, and
   a nucleic acid, wherein the nucleic acid is non-covalently associated with the second cell-penetrating domain, and wherein the second cell-penetrating domain has two or more basic amino acids, and wherein the number of basic amino acids within the second cell penetrating domain is below a threshold level of amino acids above which the polypeptide targets cells non-specifically.

2. The composition of claim 1, wherein the nucleic acid is an siRNA, and wherein the polypeptide assembles into a light-scattering complex upon complexation with the siRNA molecule.

3. The composition of claim 2, wherein the complex is not immunostimulatory.

4. The composition of claim 2, wherein the average diameter of the complex is between 10-1000 nm, 50-800 nm, 100-700 nm, or 200-600 nm.

5. The composition of claim 2, wherein the complex is renally excreted.

6. The composition of claim 2, wherein the number of basic amino acids within the second cell penetrating domain is less than 8, less than 7, less than 6, less than 5, or less than 4.

7. The composition of claim 2, wherein the charge ratio between the nucleic acid and the second cell-penetrating domain is approximately 2-3:1.

8. The composition of claim 1, wherein the first homing domain is a cyclic homing peptide.

9. The composition of claim 1, wherein the homing domain has tumor penetration properties.

10. The composition of claim 9, wherein the homing domain comprises a penetration motif R/KXXR/K, wherein R is arginine, K is lysine and X is any amino acid.

11. The composition of claim 8, wherein the cyclic homing peptide is Lyp1 or iRGD.

12. The composition of claim 1, wherein the second cell-penetrating domain is 6R or transportan (TP).

13. The composition of claim 1, wherein the lipophilic group is myristic acid.

14. A polypeptide comprising:
   a first homing domain, and
   a second domain comprising a nucleic acid binding motif wherein the second domain is N-terminal to the first homing domain, and wherein the second domain has less than 25% basic amino acids, has protein transduction function, and is non-covalently associated with a nucleic acid and,
   wherein a saturated C12-C18 fatty acid is attached to the N-terminus of the second domain.

15. A complex comprising the polypeptide of claim 14 wherein the nucleic acid is associated with the polypeptide with dissociation constant in the range of 1-100 nM, or 1-10 nM.

16. The polypeptide of claim 14,
    wherein the first homing domain facilitates destabilization of a cell membrane or the membrane of a cell organelle and allows entry into cytosol.

17. The polypeptide of claim 14, wherein the polypeptide is a non self-assembling polypeptide that assembles with identical polypeptides into light-scattering complexes upon complexation with siRNA molecules.

18. The polypeptide of claim 14, wherein upon complexation with nucleic acid molecules and other identical polypeptides, the polypeptides display the first homing domains in a multivalent fashion, thereby increasing binding affinity.

19. The polypeptide of claim 14, wherein the polypeptide is renally excreted.

20. The composition of claim 2, wherein the second domain comprises at least 10% basic amino acids.

21. The composition of claim 2, wherein the second domain comprises at least 2-4 basic amino acids.

22. The polypeptide of claim 14, wherein the nucleic acid binding motif is about 10-50 or about 10, 20, 30 or 40 amino acids long.

23. The polypeptide of claim 14, wherein the first homing domain binds a cell-type specific cell-surface moiety.

24. The polypeptide of claim 14, wherein the first homing domain comprises an antibody, antigen, ligand, receptor, cytokine, lymphokine, hormone, growth factor or fragment thereof.

25. The composition of claim 2, wherein the lipophilic group is a saturated fatty acid.

26. The composition of claim 2, wherein the first homing domain comprises Lyp-1.

27. The composition of claim 2, wherein the second domain is selected from the group consisting of: transportan, viral protein-22 (VP-22) and penetratin or a portion or a modified variant thereof.

28. The composition of claim 2, wherein the two domains are connected by a synthetic or peptide linker.

29. A method of delivering a nucleic acid, the method comprising:
   administering to a subject a nucleic acid in association with a polypeptide of claim 14.

30. The method of claim 29, wherein the nucleic acid is administered in conjunction with one or more iRGD peptides.

31. The polypeptide of claim 14, wherein the nucleic acid binding motif is a siRNA binding motif.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial sequence
<220> FEATURE:
<223> OTHER INFORMATION: Control domain

<400> SEQUENCE: 1

Ala Arg Ala Leu Pro Ser Gln Arg Ser Arg
1               5                   10

<210> SEQ ID NO 2
<211> LENGTH: 9
<212> TYPE: PRT
<213> ORGANISM: Artificial sequence
<220> FEATURE:
<223> OTHER INFORMATION: Lyp 1 tumor penetrating peptide

<400> SEQUENCE: 2

Cys Gly Asn Lys Arg Thr Arg Gly Cys
1               5
```

```
<210> SEQ ID NO 3
<211> LENGTH: 9
<212> TYPE: PRT
<213> ORGANISM: Artificial sequence
<220> FEATURE:
<223> OTHER INFORMATION: iRGD tumor penetrating peptide

<400> SEQUENCE: 3

Cys Arg Gly Asp Lys Gly Pro Asp Cys
1               5

<210> SEQ ID NO 4
<211> LENGTH: 4
<212> TYPE: PRT
<213> ORGANISM: Artificial sequence
<220> FEATURE:
<223> OTHER INFORMATION: tumor penetrating motif
<220> FEATURE:
<221> NAME/KEY: MISC_FEATURE
<222> LOCATION: (1)..(1)
<223> OTHER INFORMATION: X can be Arg or Lys
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X can be Arg or Lys

<400> SEQUENCE: 4

Xaa Xaa Xaa Xaa
1

<210> SEQ ID NO 5
<211> LENGTH: 9
<212> TYPE: PRT
<213> ORGANISM: Artificial sequence
<220> FEATURE:
<223> OTHER INFORMATION: Homing domain

<400> SEQUENCE: 5

Cys Asp Cys Arg Gly Asp Cys Phe Cys
1               5

<210> SEQ ID NO 6
<211> LENGTH: 5
<212> TYPE: PRT
<213> ORGANISM: Artificial sequence
<220> FEATURE:
<223> OTHER INFORMATION: Homing domain

<400> SEQUENCE: 6

Cys Asn Gly Arg Cys
1               5

<210> SEQ ID NO 7
<211> LENGTH: 10
<212> TYPE: PRT
<213> ORGANISM: Artificial sequence
<220> FEATURE:
<223> OTHER INFORMATION: Homing domain

<400> SEQUENCE: 7

Cys Thr Thr His Trp Gly Phe Thr Leu Cys
1               5                   10

<210> SEQ ID NO 8
<211> LENGTH: 5
```

-continued

<212> TYPE: PRT
<213> ORGANISM: Artificial sequence
<220> FEATURE:
<223> OTHER INFORMATION: Homing domain

<400> SEQUENCE: 8

Cys Gly Lys Arg Lys
1               5

<210> SEQ ID NO 9
<211> LENGTH: 5
<212> TYPE: PRT
<213> ORGANISM: Artificial sequence
<220> FEATURE:
<223> OTHER INFORMATION: Homing domain

<400> SEQUENCE: 9

Cys Asp Leu Thr Arg
1               5

<210> SEQ ID NO 10
<211> LENGTH: 9
<212> TYPE: PRT
<213> ORGANISM: Artificial sequence
<220> FEATURE:
<223> OTHER INFORMATION: Homing domain

<400> SEQUENCE: 10

Cys Arg Glu Ala Gly Arg Lys Ala Cys
1               5

<210> SEQ ID NO 11
<211> LENGTH: 8
<212> TYPE: PRT
<213> ORGANISM: Artificial sequence
<220> FEATURE:
<223> OTHER INFORMATION: Homing domain

<400> SEQUENCE: 11

Cys Ala Gly Arg Arg Ser Ala Tyr
1               5

<210> SEQ ID NO 12
<211> LENGTH: 19
<212> TYPE: RNA
<213> ORGANISM: Artificial sequence
<220> FEATURE:
<223> OTHER INFORMATION: siRNA for GFP

<400> SEQUENCE: 12
ggcuacgucc aggagcgca                                          19

<210> SEQ ID NO 13
<211> LENGTH: 19
<212> TYPE: RNA
<213> ORGANISM: Artificial sequence
<220> FEATURE:
<223> OTHER INFORMATION: siRNA for LUC

<400> SEQUENCE: 13
cuuacgcuga guacuucga                                          19

<210> SEQ ID NO 14
<211> LENGTH: 19
<212> TYPE: RNA
<213> ORGANISM: Artificial sequence
<220> FEATURE:

<223> OTHER INFORMATION: siRNA for Bgal-728

<400> SEQUENCE: 14
cuacacaaau cagcgauuu                                                     19

<210> SEQ ID NO 15
<211> LENGTH: 19
<212> TYPE: RNA
<213> ORGANISM: Artificial sequence
<220> FEATURE:
<223> OTHER INFORMATION: siRNA for ID4_568

<400> SEQUENCE: 15
gauaugaacg acugcuaua                                                     19

<210> SEQ ID NO 16
<211> LENGTH: 19
<212> TYPE: RNA
<213> ORGANISM: Artificial sequence
<220> FEATURE:
<223> OTHER INFORMATION: siRNA for ID4_621

<400> SEQUENCE: 16
caacaagaaa gucagcaaa                                                     19

<210> SEQ ID NO 17
<211> LENGTH: 21
<212> TYPE: RNA
<213> ORGANISM: Artificial sequence
<220> FEATURE:
<223> OTHER INFORMATION: siRNA for ID4_564

<400> SEQUENCE: 17
gugcgauaug aacgacugcu a                                                  21

<210> SEQ ID NO 18
<211> LENGTH: 21
<212> TYPE: RNA
<213> ORGANISM: Artificial sequence
<220> FEATURE:
<223> OTHER INFORMATION: siRNA for ID4_1195

<400> SEQUENCE: 18
ccgacuuuag aagccuacuu u                                                  21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ccgagccagg agcactagag                                                    20

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
cttggaatga cgaatgaaaa cg                                                 22

```
<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 21
tgctttgtgt tttgtcgaga ctc                                              23

<210> SEQ ID NO 22
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 22
caaccctacc cctgccaac                                                   19

<210> SEQ ID NO 23
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 23
tatgtgaacg cgcttttag ca                                                22

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
ttgtataagc ccggaacggt c                                                21

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
gagtggagcg cgcatgaag                                                   19

<210> SEQ ID NO 26
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 26
ggtgactgtc ccacgcttga c                                                21

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide
```

```
<400> SEQUENCE: 27
cctgttcgac agtcagccg                                            19

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cgaccaaatc cgttgactcc                                           20

<210> SEQ ID NO 29
<211> LENGTH: 27
<212> TYPE: PRT
<213> ORGANISM: Artificial sequence
<220> FEATURE:
<223> OTHER INFORMATION: Transportan protein transduction domain

<400> SEQUENCE: 29

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```